US007148349B2

(12) United States Patent
Reddy et al.

(10) Patent No.: US 7,148,349 B2
(45) Date of Patent: Dec. 12, 2006

(54) CYCLIC PHOSPHATE DIESTERS OF 1,3-PROPANE-1-ARYL DIOLS AND THEIR USE IN PREPARING PRODRUGS

(75) Inventors: K. Raja Reddy, San Diego, CA (US); William Craigo, San Diego, CA (US); Zhili Sun, San Diego, CA (US); Serge Boyer, San Diego, CA (US); Bheemarao G. Ugarkar, Escondido, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 0 days.

(21) Appl. No.: 10/698,924

(22) Filed: Oct. 31, 2003

(65) Prior Publication Data

US 2004/0192651 A1 Sep. 30, 2004

Related U.S. Application Data

(60) Provisional application No. 60/423,259, filed on Oct. 31, 2002, provisional application No. 60/423,211, filed on Oct. 31, 2002.

(51) Int. Cl.
*C07D 239/02* (2006.01)
*C07D 487/06* (2006.01)
*C07C 9/02* (2006.01)

(52) U.S. Cl. .................. 544/256; 544/318; 558/83
(58) Field of Classification Search ............... 544/256, 544/318; 558/83
See application file for complete search history.

(56) References Cited

U.S. PATENT DOCUMENTS

| | | | |
|---|---|---|---|
| 3,018,302 A | 1/1962 | Bielefeld et al. |
| 3,116,282 A | 12/1963 | Hunter |
| 3,328,388 A | 6/1967 | Shen et al. |
| 4,440,740 A | 4/1984 | Fix et al. |
| 4,537,772 A | 8/1985 | Alexander et al. |
| 4,692,441 A | 9/1987 | Alexander et al. |
| 4,729,989 A | 3/1988 | Alexander et al. |
| 4,731,360 A | 3/1988 | Alexander et al. |
| 4,749,694 A | 6/1988 | Fix et al. |
| 4,822,773 A | 4/1989 | Alexander et al. |
| 4,835,138 A | 5/1989 | Alexander et al. |
| 4,847,298 A | 7/1989 | Alexander et al. |
| 4,952,740 A | 8/1990 | Juge et al. |
| 4,963,525 A | 10/1990 | Alexander et al. |
| 4,963,556 A | 10/1990 | Alexander et al. |
| 4,973,579 A | 11/1990 | Alexander et al. |
| 5,077,280 A | 12/1991 | Sommadossi et al. |
| 5,118,672 A | 6/1992 | Schinazi et al. |
| 5,159,067 A | 10/1992 | Schinazi et al. |
| 5,464,748 A | 11/1995 | Sommadossi et al. |
| 5,567,689 A | 10/1996 | Sommadossi et al. |
| 5,599,686 A | 2/1997 | DeFeo-Jones et al. |
| 5,658,889 A | 8/1997 | Gruber et al. |
| 5,663,159 A | 9/1997 | Starrett, Jr. et al. |
| 5,723,449 A | 3/1998 | Sommadossi et al. |
| 5,750,493 A | 5/1998 | Sommadossi et al. |
| 5,866,679 A | 2/1999 | DeFeo-Jones et al. |
| 5,948,750 A | 9/1999 | Garsky et al. |
| 5,990,093 A | 11/1999 | Schinazi et al. |
| 6,054,587 A | 4/2000 | Reddy et al. |
| 6,110,903 A | 8/2000 | Kasibhatla et al. |
| 6,130,504 A | 10/2000 | Nakayama et al. |
| 6,143,864 A | 11/2000 | DeFeo-Jones et al. |
| 6,177,404 B1 | 1/2001 | DeFeo-Jones et al. |
| 6,194,390 B1 | 2/2001 | Lori et al. |
| 6,245,749 B1 | 6/2001 | Schinazi et al. |
| 6,284,748 B1 | 9/2001 | Dang et al. |
| 6,294,672 B1 | 9/2001 | Reddy et al. |
| 6,312,662 B1 | 11/2001 | Erion |
| 6,391,305 B1 | 5/2002 | Feng et al. |
| 6,395,716 B1 | 5/2002 | Gosselin et al. |
| 6,399,782 B1 | 6/2002 | Kasibhatla et al. |
| 6,407,077 B1 | 6/2002 | Gosselin et al. |
| 6,444,652 B1 | 9/2002 | Gosselin et al. |
| 6,458,773 B1 | 10/2002 | Gosselin et al. |
| 6,486,204 B1 | 11/2002 | Waldstreicher et al. |
| 6,489,476 B1 | 12/2002 | Dang et al. |

(Continued)

FOREIGN PATENT DOCUMENTS

EP 0180276 A1 5/1986

(Continued)

OTHER PUBLICATIONS

Aleksiuk et al., *J. Chem. Soc. Chem. comm.* (1)11, (1993).

(Continued)

*Primary Examiner*—Taofiq Solola
(74) *Attorney, Agent, or Firm*—Sterne, Kessler, Goldstein & Fox P.L.L.C.

(57) ABSTRACT

Compounds of Formula I, their preparation and synthetic intermediates, and their use in the synthesis of prodrugs:

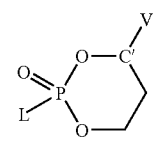

Formula I wherein:
V and L are trans relative to one another;
V is selected from group consisting of carbocyclic aryl, substituted carbocyclic aryl, heteroaryl, and substituted heteroaryl; and
L is a leaving group selected from the group consisting of halogen, alkyl sulfonate, aryloxy optionally substituted with 1–2 substituents, N-containing heteroaryl, and N-hydroxy-nitrogen containing heteroaryl;
and salts thereof.

80 Claims, No Drawings

U.S. PATENT DOCUMENTS

| | | |
|---|---|---|
| 6,525,033 B1 | 2/2003 | Schinazi et al. |
| 6,545,007 B1 | 4/2003 | Sommadossi et al. |
| 6,566,344 B1 | 5/2003 | Gosselin et al. |
| 6,569,837 B1 | 5/2003 | Gosselin et al. |
| 6,596,700 B1 | 7/2003 | Sommadossi et al. |
| 6,602,664 B1 | 8/2003 | Schinazi et al. |
| 6,635,636 B1 | 10/2003 | Artico et al. |
| 6,752,981 B1 | 6/2004 | Erion et al. |
| 6,946,115 B1 | 9/2005 | Erion et al. |
| 2001/0041713 A1 | 11/2001 | Waldstreicher et al. |
| 2002/0115596 A1 | 8/2002 | Gosselin et al. |
| 2002/0120130 A1 | 8/2002 | Gosselin et al. |
| 2002/0147160 A1 | 10/2002 | Bhat et al. |
| 2002/0193415 A1 | 12/2002 | LaColla et al. |
| 2003/0050229 A1 | 3/2003 | LaColla et al. |
| 2003/0060400 A1 | 3/2003 | LaColla et al. |
| 2003/0083306 A1 | 5/2003 | Imbach et al. |
| 2003/0225277 A1 | 12/2003 | Kopcho et al. |
| 2003/0229225 A1 | 12/2003 | Reddy et al. |
| 2003/0232760 A1 | 12/2003 | Garsky et al. |
| 2004/0006002 A1 | 1/2004 | Sommadossi et al. |
| 2004/0006007 A1 | 1/2004 | Grosselin et al. |
| 2004/0092476 A1 | 5/2004 | Erion et al. |
| 2005/0101776 A1 | 5/2005 | Gosselin et al. |
| 2005/0288240 A1 | 12/2005 | Erion et al. |

FOREIGN PATENT DOCUMENTS

| | | |
|---|---|---|
| EP | 0338372 A2 | 10/1989 |
| EP | 0353692 B1 | 10/1995 |
| EP | 0161955 A1 | 11/1995 |
| EP | 0481214 B1 | 6/1998 |
| GB | 2266525 A | 11/1993 |
| GB | 2266527 A | 3/1999 |
| NL | 6511420 | 3/1966 |
| WO | WO 91/19721 A1 | 12/1991 |
| WO | WO 95/07287 A1 | 6/1995 |
| WO | WO 96/01267 A1 | 1/1996 |
| WO | WO 97/03679 A1 | 2/1997 |
| WO | WO 97/49717 A1 | 12/1997 |
| WO | 99/45016 * | 9/1999 |
| WO | WO 00/03998 A1 | 1/2000 |
| WO | WO 00/009531 A2 | 2/2000 |
| WO | WO 00/52015 A2 | 9/2000 |
| WO | WO 01/090121 A2 | 11/2001 |
| WO | WO 01/92282 A2 | 12/2001 |
| WO | WO 02/083126 A1 | 10/2002 |
| WO | WO 03/026589 A2 | 4/2003 |
| WO | WO 03/026675 A1 | 4/2003 |
| WO | WO 04/002422 A2 | 1/2004 |
| WO | WO 04/002999 A2 | 1/2004 |
| WO | WO 04/0003000 A2 | 1/2004 |

OTHER PUBLICATIONS

Attansi et al., *Phosphorus Sulfur* 35(1-2), 63 (1988).
Ayral-Kaloustain et al., *Carbohydr. Res.* 187 (1991).
Bhatia et al., *Tetrahedron Lett.* 28(3), 271 (1987).
Bijsterbosch et al., *Antimicrob Agents Chemother.* May, 42(5): 1146-50 (1998).
Chu et al., *J. Het. Chem.* 22:1033 (1985).
Coppi et al. *J. Org. Chem.* 53:911 (1988).
Dyatkina et al., *Tetrahedron Lett.* 35(13), 1961 (1994).
Ferroni et al., *J. Org. Chem.* 64(13), 4943 (1999).
Gao, et al., *J. Org. Chem.* 53:4081 (1980).
Greene, T.W., *Protective Groups in Organic Chemistry*, John Wiley & Sons, New York (1999). (Outline only).
Gorenstein et al., *J. Am. Chem. Soc* 5077 (1980).
Gish et al., *J. Med. Chem.* 14, 1159 (1971).
Hadvary et al., *Helv. Chim. Acta* 69(8), 1862 (1986).
Hanaoka et al., *Heterocycles* 23(11), 2927 (1985).
Harada et al, *Tetrahedron Lett.* 28:4843 (1987).
Hayakawa et al., *Tetrahedron Lett.* 28(20), 2259 (1987).
Hoefler et al., *Tetrahedron* 56(11), 1485 (2000).
Hulst et al., *Tetrahedron Lett.* 1339 (1993).
Jacobsen, E.N. et al., *Comprehensive Asymmetric Catalysis* (1999). (Outlines only).
Li et al., *Tetrahedron Lett.* 6615 (2001).
March, J. *Advanced Organic Chemistry*, McGraw Hill Book Company, New York, (1977 edition) pp. 251-259.
Meek et al., *J. Am, Chem Soc.* 110(7), 2317 (1988).
Merckling et al., *Tetrahedron Lett.* 2217 (1996).
Mosbo et al., *J. Org. Chem.* 42, 1549 (1977).
Mukaiyama, *Org. React.* 28:203 (1982).
Noyori, R. et al., *Asymmetric Catalysis on Organic Synthesis* (1994) (List of content only).
Postel et al., *J. Carbohyd. Chem.* 19(2), 171 (2000).
Ramachandran et al., *Tetrahedron Lett.* 38:761 (1997).
Rathore et al., *Indian J. Chem B.* 32(10), 1066 (1993).
Roodsari et al., *J. Org. Chem.* 64(21), 7727 (1999).
Sakamoto et al., Tetrahedron Lett. 33:6845 (1992).
Stromberg et al., *J. Nucleot.* 6(5), 815 (1987).
Takaku et al., *Chem. Lett.* (5) 699 (1986).
Torneiro et al., *J. Org. Chem.* 62(18), 6344 (1997).
Turner et al., *J. Org. Chem.* 54:4229 (1989).
Turner et al., *J Org. Chem.* 55:4744 (1990).
Vankayalapati et al., *J. Chem. Soc. Perk T 1* 14, 2187 (2000).
Yamamoto et al., *Tetrahedron Lett.* 37: 1871 (1981).
Edmunson, R.S., "Cyclic Organophosphorous Compounds. Part 23. Configurational Assignments in the 4-Phenyl-1,3,2λ-dioxaphosphorinane Series, X-Ray Molecular Structure of cis-2-Benzylamino-4-phenyl-1,3,2-dioxaphosphorinane 2-Oxide" *J. Chem. Research* (S), 1989, pp. 122-123.
Alexander, P., et al., "Preparation of 9-(2-Phosphonomethoxyethyl) Adenine Esters as Potential Prodrugs," *Collect. Czech. Chem. Commun.* 59:1853-1869. Czech Academy of Sciences, Institute of Organic Chemistry and Biochemistry (1994).
Amin, D., et al., "1-Hydroxy-3-(methylpentylamino)-propylidene-1, 1-bisphosphonic Acid as a Potent Inhibitor of Squalene Synthase," *Arzneim.-Forsch/Drug Res.* 46:759-792, Blackwell Publishing, Inc. (1996).
Arner, E.S.J. and Eriksson, S., "Mammalian Deoxyribonucleoside Kinases," *Pharmacol. Ther.* 67:155-186, Elsevier Science Ltd. (1995).
Atiq, O., et al., "Treatment of Unresectable Primary Liver Cancer with Intrahepatic Fluorodeoxyuridine and Mitomycin C Through an Implantable Pump," *Cancer* 69:920-924, John Wiley and Sons, Inc. (1992).
Auberson, Y. et al., "N-Phosphonoalkyl-5-Aminomethylquinoxaline-2,3-Diones: In Vivo Active AMPA and NMDA-(Glycine) Antagonists," *Bioorg. Med. Chem. Lett.* 9:249-254, Elsevier Science Ltd. (1999).
Balthazor, T. and Grabiak, R.C., "Nickel-Catalyzed Arbuzov Reaction: Mechanistic Observations,"*J. Org. Chem.* 45:5425-5426, American Chemical Society (1980).
Beaucage, S.L. and Iyer, R.P., "The Synthesis of Modified Oligonucleotides by the Phosphoramidite Approach and Their Applications," *Tetrahedron* 49:6123-6194, Pergamon Press Ltd. (1993).
Bespalov, A., et al., "Prolongation of morphine analgesia by competitive NMDA receptor antagonist D-CPPene (SDZ EAA 494) in rats," *Eur. J. Pharmacol.* 351:299-305, Elsevier Science B.V. (1998).
Bird, J., et al., "Synthesis of Novel N-Phosphonoalkyl Dipeptide Inhibitors of Human Collagenase," *J. Med. Chem.* 37:158-169, American Chemical Society (1994).
Borch, R.F. and Millard, J.A., "The Mechanism of Activation of 4-Hydroxycyclophosphamide," *J. Med. Chem.* 30:427-431, American Chemical Society (1987).
Brill, T. and Landon, S.J., "Arbuzov-like Dealkylation Reactions of Transition-Metal-Phosphite Complexes," *Chem. Rev.* 84:577-585, American Chemical Society (1984).
Campagne, J.-M., et al., "Synthesis of Mixed Phosphate Diester Analogues of Dipeptides using BOP or PyBOP Reagents," *Tetrahedron Lett.* 34:6743-6744, Pergamon Press Ltd. (1993).

Campbell, D.A., "The Synthesis of Phosphonate Esters, an Extension of the Mitsunobu Reation," *J. Org. Chem.* 57:6331-6335, American Chemical Society (1992).

Casara, P., et al., "Synthesis of Acid Stable 5'-O-Fluoromethyl Phosphonates of Nucleosides. Evaluation as Inhibitors of Reverse Transcriptase." *Bioorg. Med. Chem. Lett.* 2:145-148, Pergamon Press plc (1992).

Casteel, D, and Peri, S.P., "Steric and Electronic Effects in the Aryl Phosphate to Arylphosphonate Rearrangement, " *Synthesis* (9):691-693, Georg Thieme Verlag KG (1991).

Chen, L. and Waxman, D.J., "Intratumoral Activation and Enhanced Chemotherapeutic Effect of Oxazaphosphorines following Cytochrome P-450 Gene Transfer: Development of a Combined Chemotherapy/Cancer Gene Therapy Strategy," *Cancer Res.* 55:581-589, The American Association for Cancer Research (1995).

Chen, L., et al., "Sensitization of Human Breast Cancer Cells to Cyclophosphamide and Ifosfamide by Transfer of a Liver Cytochrome P450 Gene," *Cancer Res.* 56:1331-1340, The American Association for Cancer Research (1996).

Cooper, D.B., et al., "Use of Carbohydrate Derivatives for Studies of Phosphorus Stereo-chemistry. Part II. Synthesis and Configurational Assignments of 1,-3,2-Oxathiaphosphrinan-2-ones and 1,3,2-Dioxaphosphorinan-2-thiones," *J. Chem. Soc. Perkin I* 3/2422:1049-1052, Royal Society of Chemistry (1974).

Dearfield, K., et al., "Analysis of the genotoxicity of nine acrylate/methacrylate compounds in L5178Y mouse lymphoma cells, " *Mutagenesis* 4:381-393, Oxford University Press (1989).

De Clercq, E., et al., "A novel selective broad-spectrum anti-DNA virus agent," *Nature* 323:464-467, Nature Publishing Group (1986).

De Lombaert, S., et al., "Pharmacological Profile of a Non-Peptidic Dual Inhibitor of Neutral Endopeptidase 24.11 and Endothelin-Converting Enzyme," *Biochem. Biophys. Res. Commun.* 204:407-412, Academic Press, Inc. (1994).

De Lombaert, S., et al., "N-Phosphonomethyl Dipeptides and Their Phosphonate Prodrugs, a New Generation of Neutral Endopeptidase (NEP, EC 3.4.24.11) Inhibitors," *J. Med. Chem.* 37:498-511, American Chemical Society (1994).

Desos, P., et al., "Structure-Activity Relationships in a Series of 2(1*H*)-Quinolones Bearing Different Acidic Function in the 3-Position: 6,7-Dichloro-2(1*H*)-oxoquinoline-3-phosphonic Acid, a New Potent and Selective AMPA/Kainate Antagonist with Neuroprotective Properties," *J. Med. Chem.* 39:197-206, American Chemical Society (1996).

De Waziers, et al., "Cytochrome P450 Isoenzymes, Epoxide Hydrolase and Glutathione Transferases in Rat and Human Hepatic and Extrahepatic Tissues," *J. Pharm. Exp. Ther.* 253:387-394, American Society for Pharmacology and Experimental Therapeutics (1990).

Dickson, J.K., et al., "Orally Active Squalene Synthase Inhibitors: Bis((acyloxy)alkyl) Prodrugs of the α-Phosphonosulfonic Acid Moiety," *J. Med. Chem.* 39:661-664, American Chemical Society (1996).

Enriquez, P., et al., "Conjugation of Adenine Arabinoside 5'-Monophosphate to Arabinogalactan: Synthesis, Characterization, and Antiviral Activity," *Bioconjugate Chem.* 6:195-202, American Chemical Society (1995).

Erion, M., et al., "Design, Synthesis, and Characterization of a Series of Cytochrome $P_{450}$ 3A-Activated Prodrugs (HepDirect Prodrugs) Useful for Targeting Phosph(on)ate-Based Drugs to the Liver, " *J. Am. Chem. Soc.* 126:5154-5163, American Chemical Society (Apr. 2004).

Erion, M., et al., "HepDirect™ Prodrugs: A Novel Strategy for Targeting Drugs to the Liver," *Hepatology* 36:301A, AASLD Abstract No. 551, John Wiley & Sons, Inc. (Oct. 2002).

Erion, M., et al., "Liver-Targeted Drug Delivery Using HepDirect Prodrugs" *J. Pharmacol. Exper. Ther.* 312:554-560, American Society for Pharmacology and Experimental Therapeutics (Feb. 2005).

Erion, M., "Liver-Targeted Nucleoside Prodrugs," presented at the *Gordon Research Conference: Purines, Pyrimidines and Related Substances*, Newport, RI, 38 pages (Jun.-Jul 2003).

Farquhar, D., et al., "Biologically-Cleavable Phosphate Protective Groups: 4-Acyloxy-1,3,2-Dioxaphosphorinanes as Neutral Latent Precursors of Dianionic Phosphates," *Tetrahedron Lett.* 36:655-658, Elsevier Science Ltd. (1995).

Farquhar, D., et al., "Biologically Reversible Phosphate-Protective Groups," *J. Pharm. Sci.* 72: 324-325, American Chemical Society (1983).

Farquhar, D., et al., "Synthesis and Antitumor Evaluation of Bis[(pivaloyloxy) methyl] 2'-Deoxy-5-fluorouridine 5'-Monophosphate (FdUMP): A Strategy to Introduce Nucleotides into Cells," *J. Med. Chem.* 37:3902-3909, American Chemical Society (1994).

Farquhar, D., et al., Synthesis and Biological Evaluation of 9- [5'-(2-Oxo-1,3,2-oxazaphosphorinan-2-yl)β -D-arabinosyl]adenine and 9-[5'-(2-Oxo-1,3,2-dioxaphosphorinan-2-yl)-β-D-arabinosyl]adenine: Potential Neutral Precursors of 9-[β-D-Arabinofuranosyl]adenine 5'-Monophosphate, *J. Med. Chem.* 28:1358-1361, American Chemical Society (1985).

Farquhar, D., et al., "5'-4-(Pivaloyloxy)-1,3,2-dioxaphosphorinan-2-yl-2'-deoxy-5-fluorouridine: A Membrane-Permeating Prodrug of 5-Fluoro-2'-deoxyuridylic Acid (FdUMP)," *J. Med. Chem.* 38, 488-495, American Chemical Society (1995).

Farquhar, D., et al., "Synthesis and Biological Evaluation of Neutral Derivatives of 5-Fluoro-2'- deoxyuridine 5'-Phosphate," *J. Med. Chem.* 26:1153-1158, American Chemical Society (1983).

Fiume, L., et al., "Inhibition of Hepatitis B Virus Replication by Vidarabine Monophosphate Conjugated with Lactosaminated Serum Albumin," *The Lancet* 2:13-15, The Lancet Publishing Group (1988).

Freed, J.J., et al. "Evidence for Acyloxymethyl Esters of Pyrimidine, 5'-Deoxyribonucleotides as Extracellular Sources of Active 5'-Deoxyribonucleotides in Cultured Cells," *Biochem. Pharm.* 38:3193-3198, Elsevier Inc. (1989).

Friis, G.J. and Bundgaard, H., "Prodrugs of phosphates and phosphonates: Novel lipophilic α-acyloxyalkyl ester derivatives of phosphate- or phosphonate containing drugs masking the negative charges of these groups," *Eur. J. Pharm. Sci.* 4:49-59, Elsevier Science B.V. (1996).

Fujii, A., et al., "Ruthenium(II)-Catalyzed Asymmetric Transfer Hydrogenation of Ketones Using A Formic Acid-Triethylamine Mixture," *J. Am. Chem. Soc.* 118:2521-2522, American Chemical Society (1996).

Guida, W.C., et al., "Structure-Based Design of Inhibitors of Purine Nucleoside Phosphorylase. 4. A. Study of Phosphate Mimics," *J. Med. Chem.* 37:1109-1114, American Chemical Society (1994).

He, K., et al., "Inactivation of Cytochrome P450 3A4 by Bergamottin, A Component of Grapefruit Juice," *Chem. Res. Toxicol.* 11:252-259, American Chemical Society (1998).

Hessler, "An Efficient Synthesis of 1-β -D-Arabinofuranosylcytosine," *J. Org. Chem.* 41:1828-1831 (1976).

Hillers, S., et al., "Analogs of pyrimidinemono-and polynucleotides. VI. Phosphates of 1-(1,4-dihydroxy-2-pentyl)thymine and 1-(1,3-dihydroxy-2-propyl) uracil," *Chemical Abstracts* 89(17), Chemical Abstracts Service (1978).

Hirayama, N., et al., "Structure and conformation of a novel inhibitor of angiotensin I converting enzyme—a tripeptide containing phosphonic acid," *Int. J. Pept. Protein Res.* 38:20-24 Blackwell Publishing (1991).

Hunston, R., et al., "Synthesis and Biological Properties of Some Cyclic Phosphotriesters Derived from 2'-Deoxy-5-fluorouridine," *J. Med. Chem.* 27:440-444, American Chemical Society (1984).

Keenan, R., et al., "Pathology Reevaluation of the Kociba et al. (1978) Bioassay of 2,3,7,8-TCDD: Implications for Risk Assessment," *J. Tox. Envir. Health* 34:279-296 , Hemisphere Publishing Corporation (1991).

Kelley, J.L., et al., "[[(Guaninylalkyl)phosphinico]methyl]phosphonic Acids. Multisubstrate Analogue Inhibitors of Human Erythrocyte Purine Nucleoside Phosphorylase," *J. Med. Chem.* 38:1005-1014, American Chemical Society (1995).

Khamnei, S. and Torrence, P.F., "Neighboring Group Catalysis in the Design of Nucleotide Prodrugs," *J. Med. Chem. 39*: 4109-4115, American Chemical Society (1996).

Khorana, H.G., et al., "Cyclic Phosphates. III. Some General Observations on the Formation of Properties of Five-,Six- and Seven-membered Cyclic Phosphate Esters," J. Am. Chem. Soc. 79:430-436, American Chemical Society (1957).

Korba, B.A., et al., "Liver-Targeted Antiviral Nucleosides: Enhanced Antiviral Activity of Phosphatidyl-Dideoxyguanosine Versus Dideoxyguanosine in Woodchuck Hepatitis Virus Infection *In Vivo,*" *Hepatology* 23:958-963, John Wiley & Sons, Inc. (1996).

Kryuchkov, A.A., et al., "Influence of Solvent on the Strength of Cyclic Oxygen-Containing Phosphorus Acids," *Bull. Acad. Sci. USSR, A translation of Izvestiya Akademii Nauk SSSR, Ser. Khim.* 36:1145-11148, Consultants Bureau (1987).

Lefebvre, I., et al., "Mononucleoside Phosphotriester Derivatives with S-Acyl-2-thioethyl Bioreversible Phosphate-Protecting Groups: Intracellular Delivery of 3'Azido-2',3'-dideoxythymidine 5'Monophosphate," *J. Med. Chem.* 38:3941-3950, American Chemical Society (1995).

Lok, A.S.F., et al., "Neurotoxicity associated with adenine arabinoside monophosphate in the treatment of chronic hepatitis B virus infection," *J. Antimicrob. Chemotherap.* 14:93-99, Oxford University Press (1984).

Lu, X. and Zhu, J., "Palladium-Catalyzed Reaction of Aryl Polyfluoroalkanesulfonates with O,O-Dialkyl Phosphonates," *Synthesis (8)*:726-727, Georg Thieme Verlag (1987).

Ludeman, S.M., et al., "Synthesis and Antitumor Activity of Cyclophosphamide Analogues. 4. Preparation Kinetic Studies, and Anticancer Screening of "Phenylketophosphamide" and Similar Compounds Related to the Cyclophosphamide Metabolite Aldophosphamide," *J. Med. Chem. 29*:716-727, American Chemical Society (1986).

MacKenna, D., et al., "MB07133: A HepDirect™ Prodrug of Cytarabine Monophosphate for Use in Hepatocellular Carcinoma," *Heptaology 38(Suppl. 1)*:411A, AASLD Abstract No. 524, John Wiley & Sons, Inc. (Oct. 2003).

McGuigan, C., et al., "Intracellular Delivery of Bioactive AZT Nucleotides by Aryl Phosphate Derivatives of AZT," *J. Med. Chem.* 36:1048-1052, American Chemical Society (1993).

McGuigan, C., et al., "Kinase Bypass: A New Strategy for Anti-HIV Drug Design," *Bioorg. Med. Chem. Lett.* 3:1207-1210, Pergamon Press Ltd. (1993).

Meier, C., et al., "Cyclic Saligenyl Phosphotriesters of 2',3'-Dideoxy-2', 3'-didehydrothymidine (d4T)—A New Pro-Nucleotide Approach -" *Bioorg. Med. Chem. Lett.* 7:99-104, Elsevier Science Ltd.(1997).

Meijer, D.K.F. and van der Sluijs, P., "Covalent and Noncovalent Protein Binding of Drugs: Implications for Hepatic Clearance, Storage, and Cell-Specific Drug Delivery," *Pharm. Res.* 6:105-118, Plenum Publishing Corporation (1989).

Melvin, L.S., "An Efficient Synthesis of 2-Hydroxyphenylphosphonates" *Tetrahedron Lett.* 22:3375-3376, Pergamon press Ltd. (1981).

Meyer, R., et al., "2'-O-Acyl-6-thioinosine Cyclic 3', 5'-Phosphates as Prodrugs of Thioinosinic Acid," *J. Med. Chem.* 22:811-815, American Chemical Society (1979).

Mitchell, A., et al., "Bioreversible Protection for the Phospho Group: Bioactivation of the Di(4-acyloxybenzyl) and Mono(4-acyloxybenzyl) Phosphoesters of Methylphosphonate and Phosphonacetate," *J. Chem. Soc. Perkin Trans. 1*, 2345-2353, Royal Society of Chemistry (1992).

Mitsunobu, O., "The Use of Diethyl Azodicarboxylate and Triphenylphosphine in Synthesis and Transformation of Natural Products," *Synthesis (1)*:1-28, Georg Thieme Verlag (1981).

Montag, A., et al., "The Effect of Dexamethasone Treatment on CYP3A Activity Distribution, the Liver Targeting of MB07133 and CYP3A Activity in a Highly Proliferating State in Rats, " *Hepatology 40(Suppl. 1)*:649A, AASLD Abstract No. 1123, John Wiley & Sons, Inc. (2004).

Moore, M., et al., "Comparison of mutagenicity results for nine compounds evaluated at the *hgprt* locus in the standard and suspension CHO assays," *Mutagenesis* 6:77-85, Oxford University Press (1991).

Murray, G., et al., "Cytochrome P450 CYP3A in human renal cell cancer," *Brit. J. Cancer* 79:1836-1842, Nature Publishing Group (1999).

Murray, G., et al., "Cytochrome P450 Expression is a Common Molecular Event in Soft Tissue Sarcomas,"*J. Pathology 171*:49-52, John Wiley & Sons, Ltd. (1993).

Nakayama, K. and Thompson, W. J., "A Highly Enantioselective Synthesis of Phosphate Triesters,"*J. Am. Chem. Soc. 112*:6936-6942, American Chemical Society (1990).

Neidlein, R., et al., "Mild Preparation of 1-Benzyloxyiminoalkylphosphonic Dichlorides: Application to the Synthesis of Cyclic Phosphonic Deisters and Cyclic Monoester Amides," *Heterocycles 35*:1185-1203, Elsevier Science (1993).

Nifantyev, E.E., et al., "Synthesis and Structure of Some Stable Phospholane-Phospholanes," *Phosphorus, Sulfur and Silicon 113*:1-13, Overseas Publishers Association (1996).

Ogg, M., et al., "A reporter gene assay to assess the molecular mechnisms of xenobiotic-dependent induction of the human CYP3A4 gene *in vitro,* " *Xenobiotica 29*:269-279, Taylor & Francis Ltd. (1999).

Ohashi, K., et al., "Synthesis of Phosphonosphingoglycolipid Found in Marine Snail *Turbo Comutus,*" *Tetrahedron Lett. 29*:1189-1192, Pergamon Press plc (1988).

Petrakis, K. and Nagabhushan, T.L., "Palladium-Catalyzed Substitutions of Triflates Derived from Tyrosine-Containing Peptides and Simpler Hydroxyarenes Forming 4-(Diethoxyphosphinyl)phenylalanines and Diethyl Arylphosphonates," *J. Am. Chem. Soc. 109*:2831-2833, American Chemical Society (1987).

Pitcher, H.R., "Built-in Bypass," *Nature 429*:39, Nature Publishing Group (May 2004).

Predvoditelev, D.A., et al., "Glycero-2-Hydroxymethylene Phosphates," *J. Org. Chem. USSR, A Translation of Zhur. Org. Khim. 13*:1489-1492, Plenum Publishing Corporation (1977).

Predvoditelev, D.A., et al., "Synthesis of Lipids and Their Models on the Basis of Glycerol Alkylene Phosphites. V. Cyclic Phosphatidylglycerol and Phosphatidylhydroxyhomocholine," *J. Org. Chem. USSR, A Translation of Zhur. Org. Khim. 17*:1156-1165, Plenum Publishing Corporation (1981).

Reddy, K.R., et al., "Stereoselective synthesis of nucleoside monophosphate HepDirect™ prodrugs," *Tetrahedron Lett. 46*:4321-4324, Elsevier Ltd. (2005).

Reddy, M.R., et al., "Development of a Quantum Mechanics-Based Free-Energy Perturbation Method: Use in the Calculation of Relative Solvation Free Energies," *J. Am. Chem. Soc. 126*:6224-6225, American Chemical Society (published online Apr. 2004).

Redmore, D., "Phosphorus Derivatives of Nitrogen Heterocycles. 2. Pyridinophosphonic Acid Derivatives," *J. Org. Chem. 35*:4114-4117, American Chemical Socirty (1970).

Ruiz Van Haperen, V.W.T., et al., "Induction of Resistance to 2'-2'-Difluorodeoxycytidine in the Human Ovarian Cancer Cell Line A2780," *Semin. Oncol. 22 (Suppl. 11)*:35-41, W.B. Saunders Company (1995).

Shaw, J.-P. and Cundy, K.C., "Biological Screens of PMEA Prodrugs," *Pharm. Res. 10*: S-294, Kluwer Academic Publishers B.V., Abstract No. PDD 7480 (1993).

Shen, T.Y., et al., "Nucleosides I. A New Synthesis of 1-β-D-Arabinofuranosyl Pyrimidine Nucleosides," *J. Org. Chem.* 30:835-838, American Chemical Society (1965).

Shih, Y.-E., et al., "Preparation and Structures of 2-Dimethylamino-4-phenyl-1,3,2-dioxaphosphorinane-2-oxides," *Bull. Inst. Chem. Acad. Sin. 41*:9-16, Academica Sinica, Nankang, Taipei, Taiwan (1994).

Shirai, R. et al., "Asymmetric Synthesis of Antimitotic Combretadioxolane with Potent Antitumor Activity Against Multi-Drug Resistant Cells," *Bioorg. Med. Chem. Lett.* 8:1997-2000, Elsevier Science Ltd. (1998).

Starrett, Jr., et al., "Synthesis, Oral Bioavailability Determination, and *in Vitro* Evaluation of Prodrugs of the Antiviral Agent 9-[2-

(Phosphonomethoxy)ethyl]adenine (PMEA)," *J. Med. Chem.* 37:1857-1864, American Chemical Society (1994).

Thomson, W., et al., "Synthesis, Bioactivation and Anti-HIV Activity of the Bis(4-acyloxybenzyl) and Mono(4-acyloxybenzyl) Esters of the 5'-monophosphate of AZT," *J. Chem. Soc. Perk. Trans. 1*, 1239-1245 Royal Society of Chemistry (1993).

Valentine, Jr., D., "Preparation of the Enantiomers of Compounds Containing Chiral Phosphorus Centers," *Asymmetric Synthesis* 4:263-312, Academic Press, Inc. (1984).

Venook, A., "Treatment of Hepatocellular Carcinoma: Too Many Options?, " *J. Clin. Oncol. 12*: 1323-1334, American Society of Clinical Oncology (1994).

Vo-Quang, Y., et al., "(1-Amino-2-propenyl)phosphonic Acid, an Inhibitor of Alanine Reacemase and D-Alanine: D-Alanine Ligase," *J. Med. Chem. 29*: 579-581, American Chemical Society (1986).

Wagner A., et al., "Direct Conversion of Tetrahydropyranylated Alcohols to the Corresponding Bromides," *Tetrahedron Lett. 30*:557-558, Pergamon Press plc (1989).

Wallace, E.M., et al., "Design and Synthesis of Potent, Selective Inhibitors of Endothelin-Converting Enzyme," *J. Med. Chem.* 41:1513-1523, American Chemical Society (1998).

Walsh, E., Et al., "Phenoxymethylphosphonic Acids and Phosphonic Acid Ion-exchange Resins," *Phenoxymethylphosphonic Acid Ion-Exchange Resins* 78:4455-4458, American Chemical Society (1956).

Watkins, P., "Noninvasive tests of CYP3A enzymes," *Pharmacogenetics* 4:171-184, Lippincott Williams & Wilkins (1994).

Weber, G.F. and Waxman, D.J., "Activation of the Anti-cancer Drug Ifosphamide by Rat Liver Microsomal P450 Enzymes," *Biochem. Pharm. 45*:1685-1694, Pergamon Press Ltd. (1993).

Wechter, W.J., et al., "Nucleic Acids, 16. Orally Active Derivatives of ara- Cytidine[1,2]," *J. Med. Chem. 19*:1013-1017, American Chemical Society (1976).

Weibel, M., et al., "Potentiating Effect of {2-[2-[(2-Amino-1,6-Dihydro-6-Oxo-9H-Purin-9-yl)Methyl]-Phenyl] Ethenyl}-Phosphonic Acid (MDL 74,428), A Potent Inhibitor of Purine Nucleoside Phosphorylase, on the Antiretroviral Activities of 2', 3'-Dideoxyinosine Combined to Ribavirin in Mice," *Biochem. Pharmacol. 48*:245-252, Elsevier Science Ltd. (1994).

Wileman, T., et al., "Receptor-mediated endocytosis," *Biochem. J.* 232:1-14, Portland Press (1985).

Yu, L. J., et al., "In vivo Modulation of Alternative Pathways of P-450-Catalyzed Cyclophosphamide Metabolism: Impact on Pharmacokinetics and Antitumor Activity," *J. Pharmacol. Exp. Ther. 288*:928-937, The American Society for Pharmacology and Experimental Therapeuctics (1999).

Zon, G., "Cyclophosphamide Analogues" in *Progress in Medicinal Chemistry*, Ellis, G.P., et al., eds., Elsevier Biomedical Press, Chapter 4, pp. 205-246 (1982).

Zon, G., et al., "NMR Spectroscopic Studies of Intermediary Metabolites of Cyclophosphamide. A Comprehensive Kinetic Analysis of the Interconversion of cis-and trans-4-Hydroxycyclophosphamide with Aldophosphamied and the Conocomitant Partitioning of Aldophosphamide between Irreversible Fragmentation and Reversible Conjugation Pathways." *J. Med. Chem. 27*:466-485, American Chemical Society (1984).

Braess, J. et al. "Oral Cytarabine Ocfostate in Acute Myeloid Leukemia and non-Hodgkins's Lymphoma—Phase I/II Studies and Pharmacokinetics", *Leukemia* 12:1618-1626, Stockton Press (1998).

Chabner B.A., "Cytidine Analogues", in *Cancer Chemotherapy: Principles and Practice*, Lippincott Williams & Wilkins (1990).

Chabner, B.A., et al., "Purification and Properties of Cytidine Deaminase from Normal and Leukemia Granulocytes", *Journal of Clinical Investigation* 53:922-931, American Society for Clinical Investigation (1074).

Cohen, S.S. "The Mechanisms of Lethal Action of Arabinosyl Cytosine (araC) and Arabinosyl Adenine (araA) ", *Cancer* 40:509-518, Wiley (1977).

Grant, S., "Biochemical Modulation of Cytosine Arabinoside", *Pharmac. Ther.* 48:29-44, Pergamon Press plc (1990).

Leach, W.B. et al. "Toxicity Studies in Mice Treated with 1-β-D-Arabinofuranosyl-cytosine (ara-C)", *Cancer Research* 29:529-535, America Association for Cancer Research (1969).

Plunkett, W. et al. "Pharmacologically Directed Ara-C Therapy for Refractory Leukemia", *Seminars in Oncology* 12(2) Supp. 3:20-30, W.B. Saunders (1985).

Rustum, Y.M., et al. "1 β-Arabinofuranosylcytosine in Therapy of Leukemia: Preclinical and Clinincal Overview" *Pharmac. Ther.* 56:307-321, Pergamon Press Ltd. (1992).

Sartillo-Piscil, F., et al., "Fosfato-ésteres ciclicos diastereoisoméricos: 5-bromo-4-fenil-2-fenoxi-2-oxo-1,3,2-dioxafosforinanos, precursores de radicales libres alquilo β-fosfatoxi y generadores de radicales catiónicos en medio no oxidativo," *Rev. Soc. Quim. Mexico* 46:330-334, Journal of the Mexican Chemical Society (Dec. 2002).

English Translation of Saratillo-Piscil, F., et al., "Cyclic diastereoisomeric phosphate esters: 5-bromo-4-phenyl-2-phenoxy-2-oxo-1,3,2-dioxaphosphorinanes, free β-(phosphatoxy) alkyl radical precursors and cation radical generators in non-oxidative medium," *Rev. Soc. Quim. Mexico* 46:330-334, Journal of the Mexican Chemical Society (Dec. 2002).

Shimma, N. et. al., "The Design and Sythesis of a New Tumor-Selective Fluoropyrimidine Carbamate, Capecitabine" *Bioorganic & Medicinal Chemistry* 8:1697-1706, Elsevier Science Ltd. (2000).

Suto, T. et al. "The Effect of YNK-01 (an Oral Prodrug of Cytarabine) on Hepatocellular Carcinoma" *Seminars in Oncology* 24(2) Suppl 6:S6-122-S6-129, W.B. Saunders (1997).

Takaku, H., et al., "Synthesis of Deoxyribooligonucleotides Using Cesium Fluoride by the Phosphotriester Approach," *Nippon Kagaku Kaisha (No. 10)*: 1968-1973, The Chemical Society of Japan, Inc. (1985).

English translation of Takaku, H., et al., "Synthesis of Deoxyribooligonucleotides Using Cesium Fluoride by the Phosphotriester Approach," *Nippon Kagaku Kaisha (No. 10)*: 1968-1973, The Chemical Society of Japan, Inc. (1985).

Thuong, N.-T. and Chabrier, P., "Nouvelle méthode de pré paration de la phosphorylcholine de la phosphorylhomocholine et de leurs dérivés," *Bull. Soc. Chim. France* 1-2:667-671, Masson and Co. (1974).

English translation of Thuong, N.T. and Chabrier, P., "New Method for Preparation of Phosphoryl choline, of phosphoryl homocholine and their derivatives," *Bull. Soc. Chim. France* 1-2:667-671, Masson and Co. (1974).

Yoshida, Y. et al., "Participation of the Peroxisomal β-Oxidation System in the Chain-Shortening of $PCA_{16}$, A Metabolite of the Cytosine Arabinoside Prodrug, YNK01, in Rat Liver" *Biochemical Pharmacology* 39(10): 1505-1512, Pergamon Press plc (1990).

Dialog File 351, Accession No. 11683821, WPI English language abstract of WO 97/49717 (Document FP3 listed on accompanying PTO/SB/08A form). Dec. 31, 1997.

Copy of Office Action for U.S. Patent Appl. No. 10/698,928, Boyer et al., mailed Mar. 13, 2006.

Copy of Office Action for U.S. Appl. No. 11/145/194, Mark D. Erion et al., filed Jun. 3, 2005, mailed Mar. 24, 2006.

\* cited by examiner

CYCLIC PHOSPHATE DIESTERS OF 1,3-PROPANE-1-ARYL DIOLS AND THEIR USE IN PREPARING PRODRUGS

This application claims the benefit of U.S. Provisional Application No. 60/423,259, filed Oct. 31, 2002 and U.S. Provisional Application No. 60/423,211, filed Oct. 31, 2002, which are incorporated by reference herein in their entirety.

FIELD OF THE INVENTION

The present invention is directed towards certain novel cyclic phosphate diesters of 1-aryl-1,3-propane diols, their preparation and synthetic intermediates, and their use in the synthesis of prodrugs. More specifically, the invention relates to the optionally substituted cyclic phosphate diesters of 1-aryl-1,3-propane diols, that have the trans-stereochemistry and their use to synthesize phosphate prodrugs that have the cis-configuration.

BACKGROUND OF THE INVENTION

The following description of the background of the invention is provided to aid in understanding the invention, but is not admitted to be, or to describe, prior art to the invention. All publications are incorporated by reference in their entirety.

Free phosphorus and phosphonic acids and their salts are highly charged at physiological pH and therefore frequently exhibit poor oral bioavailiability, poor cell penetration and limited tissue distribution (e.g. CNS). In addition, these acids are also commonly associated with several other properties that hinder their use as drugs, including short plasma half-life due to rapid renal clearance, as well as toxicities (e.g. renal, gastrointestinal, etc.) (e.g., *Antimicrob Agents Chemother*. May; 42(5): 1146–50 (1998)). Phosphates have an additional limitation in that they are not stable in plasma as well as most tissues since they undergo rapid hydrolysis via the action of phosphatases (e.g. alkaline phosphatase, nucleotidases). Accordingly, phosphate esters are frequently used as a prodrug strategy, especially for water insoluble compounds, since the phosphate group enables high water solubility and thereby enables delivery of the drug parenterally.

Liver cancer is poorly treated with current therapies. In general, liver tumors are resistant to radiotherapy, respond poorly to chemotherapy and are characterized by a high degree of cell heterogeneity.

Hepatitis and liver cancer remain poorly treated with current therapies due to dose-limiting extrahepatic side effects or inadequate delivery of chemotherapeutic agents to the target tissue.

Many nucleosides have been used as oncolytics or antiviral agents. Frequently, these compounds are reported to exhibit low activity due to either poor substrate activity of the corresponding nucleoside with viral kinases or because the viral nucleoside kinase which is required to convert the nucleoside to the monophosphate is down regulated viral resistance. Monophosphates, however, are difficult to deliver to virally-infected cells after oral administration due to their high charge and in the case of the monophosphate instability in plasma. In addition, these compounds often have short half-lives due in most cases to high renal clearance. In some cases, the high renal clearance can lead to nephrotoxicities or be a major limitation in diseases such as diabetes where renal function is often compromised.

Limitations in approaches described above include drug loading capacity, complexity of the manufacture and characterization of the conjugate, and receptor down regulation. Thus, there is still a need for prodrugs of phosphorus containing drugs.

SUMMARY OF THE INVENTION

The present invention is directed towards certain novel cyclic phosphate diesters of 1-aryl-1,3-propane diols, having the trans-stereochemistry, their preparation and synthetic intermediates, and their use in the synthesis of prodrugs.

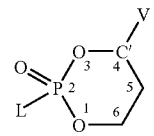

Formula I

Wherein V and L are trans relative to one another;

V is selected from the group consisting of carbocyclic aryl, substituted carbocyclic aryl, heteroaryl, and substituted heteroaryl.

The group L is a leaving group selected from the group consisting of halogen, aryloxy alkyl sulfonates, substituted-aryloxy groups, haloalkoxy, perhaloalkoxy, or N-hydroxy-nitrogen containing-heteroaryl groups.

Compounds of Formula I are either racemic, have the S configuration at carbon C', or have the R configuration at carbon C'.

The present invention provides several methods for the stereoselective synthesis of compounds of Formula I using 1-(V)-1,3-propane diol of Formula A.

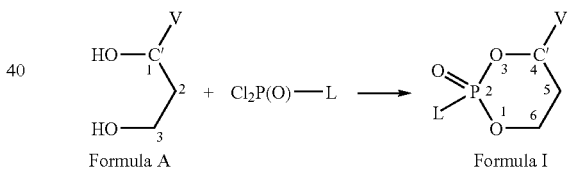

Formula A            Formula I

The present invention also provides novel methods for the use of these trans-phosphorylating reagents for the stereoselective synthesis of cis-phosphate prodrugs of Formula II.

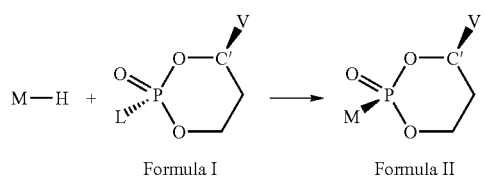

Formula I            Formula II

M is selected from the group that attached to $PO_3^{2-}$, $P_2O_6^{3-}$, or $P_3O_9^{4-}$ is the biologically active agent, and that is attached to the phosphorus in Formula II via an oxygen, sulfur or nitrogen atom;

and pharmaceutically acceptable prodrugs and salts thereof.

Since these compounds have asymmetric centers, the present invention is directed not only to racemic and diastereomeric mixtures of these compounds, but also to individual stereoisomers. The present invention also includes pharmaceutically acceptable and/or useful salts of the compounds of Formula I, including acid addition salts.

DEFINITIONS

In accordance with the present invention and as used herein, the following terms are defined with the following meanings, unless explicitly stated otherwise.

The term "aryl" refers to aromatic groups which have 5–14 ring atoms and at least one ring having a conjugated pi electron system and includes carbocyclic aryl, heterocyclic aryl and biaryl groups, all of which may be optionally substituted. Suitable aryl groups include phenyl and furan-2,5-diyl.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups having from 1 to 4 heteroatoms as ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "N-containing heteroaryl" refers to heteroaryl group with 1 to 3 nitrogens as ring atoms and attached via a carbon atom.

The term "biaryl" represents aryl groups containing more than one aromatic ring including both fused ring systems and aryl groups substituted with other aryl groups. Such groups may be optionally substituted. Suitable biaryl groups include naphthyl and biphenyl.

The term "optionally substituted" or "substituted" includes groups substituted by one to four substituents, independently selected from lower alkyl, lower aryl, lower aralkyl, hydroxy, lower alkoxy, lower aryloxy, perhaloalkoxy, aralkoxy, heteroaryl, heteroaryloxy, heteroaralkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl. "Substituted aryl" and "substituted heteroaryl" preferably refers to aryl and heteroaryl groups substituted with 1–4 substituents. Preferably these substituents are selected from the group consisting of lower alkyl, lower alkoxy, lower perhaloalkyl, halo, hydroxy, and amino.

The term "leaving group" refers to the part of the substrate molecule which when cleaved in a reaction does not contain the phosphorus that was supplied to the bond during the reaction.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, Advanced Organic Chemistry, McGraw Hill Book Company, New York, (1977 edition) pp. 251–259.

The Hammett constant values are generally negative for electron donating groups ($\sigma_p$=–0.66 for $NH_2$) and positive for electron withdrawing groups ($\sigma_p$=0.78 for a nitro group), $\sigma_p$ indicating para substitution. Exemplary electron-withdrawing groups include nitro, ketone, aldehyde, sulfonyl, trifluoromethyl, —CN, chloride, fluoride, and the like.

The term "-aralkyl" refers to an alkylene group substituted with an aryl group. Suitable aralkyl groups include benzyl, picolyl, and the like, and may be optionally substituted. "Heteroarylalkyl" refers to an alkylene group substituted with a heteroaryl group.

The term "-alkylaryl" refers to an aryl group substituted with an alkyl group. "Lower-alkylaryl" refers to such groups where alkyl is lower alkyl.

The term "lower" referred to herein in connection with organic radicals or compounds respectively defines such as with up to and including 10, preferably up to and including 6, and advantageously one to four carbon atoms. Such groups may be straight chain, branched, or cyclic.

The term "alkylamino" refers to —NRR' where R and R' are independently selected from hydrogen or alkyl.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl and aryl.

The term "carboxy esters" refers to —C(O)OR where R is alkyl, aryl, and aralkyl, all optionally substituted.

The term "carboxyl" refers to —C(O)OH.

The term "oxo" refers to =O in an alkyl group.

The term "amino" refers to —NRR' where R and R' are independently selected from hydrogen, alkyl, aryl, aralkyl and alicyclic, all except H are optionally substituted; and R and R' can form a cyclic ring system.

The term "-carboxylamido" refers to —$CONR_2$ where each R is independently hydrogen or alkyl.

The term "halogen" or "halo" refers to —F, —Cl, —Br and —I.

The term "sulphonyl" or "sulfonyl" refers to R—$SO_2$, where R is selected from alkyl, aryl, aralkyl, and alicyclic.

The term "sulphonate" or "sulfonate" refers to R—$SO_2$—O—, where R is selected from alkyl, aryl, aralkyl, and alicyclic.

The term "sulphonic acid" or "sulfonic acid" refers to R—$SO_2$, —OH, where R is selected from alkyl, aryl, aralkyl, and alicyclic.

The term "alkylaminoalkylcarboxy" refers to the group alkyl-NR-alk-C(O)—O— where "alk" is an alkylene group, and R is a H or lower alkyl.

The term "alkyl" refers to saturated aliphatic groups including straight-chain, branched-chain and cyclic groups. Alkyl groups may be optionally substituted. Suitable alkyl groups include methyl, isopropyl, and cyclopropyl.

The term "cyclic alkyl" or "cycloalkyl" refers to alkyl groups that are cyclic of 3 to 10 atoms, more preferably 3 to 6 atoms. Suitable cyclic groups include norbornyl and cyclopropyl. Such groups may be substituted.

The term "heterocyclic" and "heterocyclic alkyl" refer to cyclic groups of 3 to 10 atoms, more preferably 3 to 6 atoms, containing at least one heteroatom, preferably 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spirocyclic groups. Suitable heterocyclic groups include pyrrolidinyl, morpholino, morpholinoethyl, and pyridyl.

The term "alkenyl" refers to unsaturated groups which contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g. it is a V substituent attached to the cyclic phosphate, it is attached at the first carbon.

The term "alkynyl" refers to unsaturated groups which contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g. it is a V substituent attached to the cyclic phosphate, it is attached at the first carbon.

The term "alkylene" refers to a divalent straight-chain, branched-chain or cyclic saturated aliphatic group.

The term "acyloxy" refers to the ester group —O—C(O)R, where R is H, alkyl, alkenyl, alkynyl, aryl, or aralkyl.

The term "aminoalkyl-" refers to the group $NR_2$-alk- wherein "alk" is an alkylene group and R is selected from H, alkyl, aryl, and aralkyl.

The term "alkylaminoalkyl-" refers to the group alkyl-NR-alk- wherein each "alk" is an independently selected alkylene, and R is H or lower alkyl. "Lower alkylaminoalkyl-" refers to groups where each alkylene group is lower alkylene.

The term "arylaminoalkyl-" refers to the group aryl-NR-alk- wherein "alk" is an alkylene group and R is H, alkyl, aryl, and aralkyl. In "lower arylaminoalkyl-", the alkylene group is lower alkylene.

The term "alkylaminoaryl-" refers to the group alkyl-NR-aryl- wherein "aryl" is a divalent group and R is H, alkyl, and aralkyl. In "lower alkylaminoaryl-", the alkylene group is lower alkyl.

The term "alkoxyaryl-" refers to an aryl group substituted with an alkyloxy group. In "lower alkyloxyaryl-", the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "aryloxy-" refers to the group aryl-O—

The term "alkoxy-" or "alkyloxy-" refers to the group alkyl-O—.

The term "alkoxyalkyl-" or "alkyloxyalkyl-" refer to the group alkyl-O-alk- wherein "alk" is an alkylene group. In "lower alkoxyalkyl-", each alkyl and alkylene is lower alkylene.

The terms "alkylthio-" refers to the group alkyl-S—.

The term "alkylthioalkyl-" refers to the group alkyl-S-alk- wherein "alk" is an alkylene group. In "lower alkylthioalkyl-" each alkyl and alkylene is lower alkylene.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The terms "amido" or "carboxamido" refer to $NR_2$—C(O)— and RC(O)—$NR^1$—, where R and $R^1$ include H, alkyl, aryl, and aralkyl. The term does not include urea, —NR—C(O)—NR—.

The term "carboxamidoalkylaryl" and "carboxamidoaryl" refers to an aryl-alk-$NR^1$—C(O), and aryl-$NR^1$—C(O)-alk-, respectively where "alk" is alkylene, $R^1$ and R include H, alkyl, aryl, and aralkyl.

The term "hydroxyalkyl" refers to an alkyl group substituted with one —OH.

The term "haloalkyl" refers to an alkyl group substituted with one halo.

The term "cyano" refers to —C≡N.

The term "nitro" refers to —$NO_2$.

The term "acylalkyl" refers to an alkyl-C(O)-alk-, where "alk" is alkylene.

The term "aminocarboxamidoalkyl-" refers to the group $NR_2$—C(O)—N(R)-alk- wherein R is an alkyl group or H and "alk" is an alkylene group. "Lower aminocarboxamidoalkyl-" refers to such groups wherein "alk" is lower alkylene.

The term "heteroarylalkyl" refers to an alkyl group substituted with a heteroaryl group.

The term "perhalo" refers to groups wherein every C—H bond has been replaced with a C-halo bond on an aliphatic or aryl group. Suitable perhaloalkyl groups include —$CF_3$ and —$CFCl_2$.

The term "guanidino" refers to both —NR—C(=NR)—$NR_2$ as well as —N=C($NR_2$)$_2$ where each R group is independently selected from the group of —H, alkyl, alkenyl, alkynyl, and aryl, all except —H are optionally substituted.

The term "amidino" refers to —C(=NR)—$NR_2$ where each R group is independently selected from the group of —H, alkyl, alkenyl, alkynyl, and aryl, all except —H are optionally substituted.

The term "4-pyridyl", "pyrid-4-yl" and "4-pyridinyl" refer to the following:

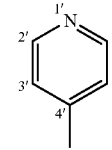

The term "N-hydroxy-nitrogen-containing heteroaryl" refers to a N-containing heteroaryl where a hydroxy group is attached to a nitrogen atom. An example is N-hydroxybenzotriazole.

The term "N-containing heteroaryl solvent" is a heteroaryl group with 1 to 3 nitrogens as ring atoms and a 4<pka<6 and any mixture with non N-containing heteroaryl solvents.

The term "pharmaceutically acceptable salt" includes salts of compounds of Formula I and its prodrugs derived from the combination of a compound of this invention and an organic or inorganic acid or base. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucoronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis[3-hydroxy-2-naphthalenecarboxylic acid], phosphoric acid, polygalacturonic acid, stearic acid, succinic acid, sulfuric acid, sulfosalicylic acid, tannic acid, tartaric acid, terephthalic acid, and p-toluenesulfonic acid.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, R$_2$N—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula I, fall within the scope of the present invention. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. The biologically active compounds include, for example, anticancer agents, antiviral agents, and antibiotic agents.

The term "phosphate" refers to phosphates, thiophosphates, and phosphoramidates which are compounds attached via O, S, or N, respectively, to the phosphorus in —P(O)(OR)(OR), including cyclic forms.

The term "cyclic phosphate" refers to phosphates diesters where —P(O)(OR)(OR) is

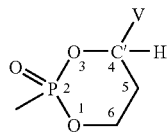

The carbon attached to V must have a C—H bond.

The term "phosphate" refers to compounds attached via C, O, S or N to $PO_3^{2-}$.

The term "phosphate" refers to —O—PO$_3$R$_2$.
The term "thiophosphate" refers to —S—PO$_3$R$_2$.
The term "phosphoramidate" refers to —N—PO$_3$R$_2$.

The term "carbocyclic sugar" refers to sugar analogs that contain a carbon in place of the oxygen normally found in the sugar ring. It includes 5-membered rings such as ribofuranosyl and arabinofuranosyl sugars wherein the ring oxygen is replaced by carbon.

The term "acyclic sugar" refers to sugars that lack a ring, e.g. ribofuranosyl ring. An example is HO—CH$_2$—CH$_2$—O—CH$_2$— in place of the ribofuranosyl ring.

The term "L-nucleoside" refers to enantiomer of the natural β-D-nucleoside analogs.

The term "arabinofuranosyl nucleoside" refers to nucleoside analogs containing an arabinofuranosyl sugar, i.e., where the 2'-hydroxyl of ribofuranosyl sugars is on the opposite face of the sugar ring.

The term "dioxolane sugar" refers to sugars that contain an oxygen atom in place of the 3' carbon of the ribofuranosyl sugar.

The term "fluorinated sugars" refers to sugars that have 1–3 carbon-fluorine atoms.

The term "nucleoside" refers to a purine or pyrimidine base, or analogs thereof, connected to a sugar, including heterocyclic and carbocyclic analogs thereof.

The terms "V and L are trans relative to one another", "trans-configuration", "trans-phosphate", "trans-phosphorylating agent" and "trans-isomer" refer to the formulas I.A and I.B:

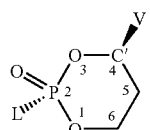

Formula I.A

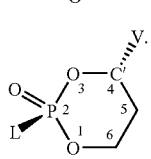

Formula I.B

The terms "V and M are cis relative to one another", "cis-configuration", "cis-prodrug", and "cis-isomer" refer to the formulas II.A and II.B:

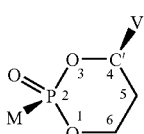

Formula II.A

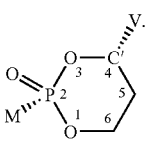

Formula II.B

The terms "S-configuration" or "S-isomer" refers to the absolute configuration S of carbon C'.

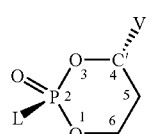

Formula I.B

The terms "R-configuration" or "R-isomer" refers to the absolute configuration R of carbon C'.

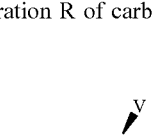

Formula I.A

The term "parent drug" refers to MH for phosphates where M is connected to —P(O)(OR)(OR) via oxygen, sulfur, or nitrogen. For example, AZT can be thought of as a parent drug in the form of MH. In the body AZT is first phosphorylated to AZT-PO₃²⁻ and then further phosphorylated to form AZT-triphosphate, which is the biologically active form. The parent drug form MH only applies when M is attached via N, S, or O.

The term "biologically active drug or agent" refers to the chemical entity that produces the biological effect. In this invention, biologically active agents refers to M—PO$_3^{2-}$, M P$_2$O$_6^{3-}$, or M—P$_3$O$_9^{4-}$ where M can be the same M as in the parent drug or a metabolite.

The term "percent enantiomeric excess (% ee)" refers to optical purity. It is obtained by using the following formula:

$$\frac{[R] - [S]}{[R] + [S]} \times 100 = \%R - \%S$$

where [R] is the amount of the R isomer and [S] is the amount of the S isomer. This formula provides the % ee when R is the dominant isomer.

The term "optical purity" refers to the chemical entity that consists of a single enantiomer.

The term "enantioenriched" or "enantiomerically enriched" refers to a sample of a chiral compound that consists of more of one enantiomer than the other. The extent to which a sample is enantiomerically enriched is quantitated by the enantiomeric ratio or the enantiomeric excess.

The following well-known drugs are referred to in the specification and the claims. Abbreviations and common names are also provided.

araA; 9-β-D-arabinofuranosyladenine (Vidarabine)
AZT; 3'-azido-2',3'-dideoxythymidine (Zidovudine)
d4T; 2',3'-didehydro-3'-deoxythymidine (Stavudine)
ddI; 2',3'-dideoxyinosine (Didanosine)
ddA; 2',3'-dideoxyadenosine
ddC; 2',3'-dideoxycytidine (Zalcitabine)
L-ddC; L-2',3'-dideoxycytidine
L-FddC; L-2',3'-dideoxy-5-fluorocytidine
L-d4C; β-L-2',3'-didehydro-2',3'-dideoxy-cytidine
L-Fd4C; β-L-2',3'-didehydro-2',3'-dideoxy-5-fluorocytidine
3TC; (−)-2',3'-dideoxy-3'-thiacytidine; 2'R,5'S(−)-1-[2-(hydroxymethyl)oxathiolan-5-yl]cytosine (Lamivudine)
1-β-D-ribofuranosyl-1,2,4-triazole-3-carboxamide (Ribavirin)
5-fluoro-2'-deoxyuridine (Floxuridine)
FIAU; 1-(2'-deoxy-2'-fluoro-β-D-arabinofuranosyl)-5-iodouridine
FIAC; 1-(2'-deoxy-2'-fluoro-β-D-arabinofuranosyl)-5-iodocytosine
BHCG; (±)-(1α,2β,3α)-9-[2',3'-bis(hydroxymethyl)cyclobutyl]guanine
L-FMAU; 2'-Fluoro-5-methyl-β-L-arabinofuranosyluracil
BvaraU; 1'-β-D-arabinofuranosyl-E-5-(2-bromovinyl)uracil (Sorivudine)
E-5-(2-bromovinyl)-2'-deoxyuridine
TFT; Trifluorothymidine
5-propynyl-1-arabinofuranosyluracil (Zonavir)
CDG; carbocyclic 2'-deoxyguanosine
DAPD; (−)-β-D-2,6-diaminopurine dioxolane
FDOC; (−)-β-D-5-fluoro-1-[2'-(hydroxymethyl)-1',3'-dioxolane]cytosine
d4C; -2',3'-didehydro-2',3'-dideoxy-cytidine
DXG; dioxolane guanosine
FEAU; 2'-deoxy-2'-fluoro-1'-β-D-arabinofuranosyl-5-ethyluracil
FLG; 2',3'-dideoxy-3'-fluoroguanosine
FLT; 3'-deoxy-3'-fluorothymidine
FTC; (−)-cis-5-fluoro-1-[2'-(hydroxymethyl)-1',3'-oxathiolan-5'-yl]cytosine
L-dT; β-L-2'-deoxythymidine (NV-02B)
L-dC; β-L-2'-deoxycytosine, valine prodrug derivatives of β-L-2'-deoxycytosine
5-yl-carbocyclic 2'-deoxyguanosine (BMS200,475).
Oxetanocin A; 9-(2'-deoxy-2'-hydroxymethyl-β-D-erythro-oxetanosyl)adenine
Oxetanocin G; 9-(2'-deoxy-2'-hydroxymethyl-β-D-erythro-oxetanosyl)guanine
Cyclobut A; (+/−)-9-[(1'-β,2'-α,3'-β)-2',3'-bis(hydroxymethyl)-1'-cyclobutyl]adenine
Cyclobut G; (+/−)-9-[(1'-β,2'-α,3'-β)-2,3-bis(hydroxymethyl)-1-cyclobutyl]guanine (Lobucavir)
dFdC; 2',2'-difluoro-2'-deoxycytidine (Gemcitabine)
araC; arabinofuranosylcytosine (Cytarabine)
bromodeoxyuridine
IDU; 5-iodo-2'-deoxyuridine (Idoxuridine)
CdA; 2-chloro-2'-deoxyadenosine (Cladribine)
FaraA; 2-fluoroarabinofuranosyladenosine (Fludarabine)
Coformycin
2'-deoxycoformycin
araT; 1-β-D-arabinofuranoside thymidine
ddAPR: 2,6-diaminopurine-2',3'-dideoxyriboside
9-(arabinofuranosyl)-2,6-diaminopurine
9-(2'-deoxyribofuranosyl)-2,6-diaminopurine
9-(2'-deoxy-2'-fluororibofuranosyl)-2,6-diaminopurine
9-(arabinofuranosyl)guanine
9-(2'-deoxyribofuranosyl)guanine
9-(2'-deoxy-2'-fluororibofuranosyl)guanine
FMdC; (E)-2'-deoxy-2'(fluoromethylene)cytidine
DMDC; 2'-deoxy-2'-methyledene-cytidine
4'-thio-araC; 4'-thio-arabinofuranosyl-cytidine
5,6 dihydro-5-azacytidine
5-azacytidine
5-aza-2'-deoxycytidine
AICAR; 5-aminoimidazole-4-carboxamido-1-ribofuranosyl
NK-84-0218 nucleoside analogue
AM365, acylic guanosine nucleoside analogue
MCC478, nucleoside analogue
ICN 2001, nucleoside analogue
Fluor L and D nucleosides, nucleoside analogue
Famciclovir, 2-[2-(2-amino-9H-purin-9-yl)ethyl]-1,3-propanediol diacetate
ACV; 9-(2'-hydroxyethoxylmethyl)guanine (Acyclovir)
GCV; 9-(1',3'-dihydroxy-2'-propoxymethyl)guanine (gancyclovir)
9-(4'-hydroxy-3'-hydroxymethylbut-1'-yl)guanine (Penciclovir)
(R)-9-(3',4'-dihydroxybutyl)guanine (Buciclovir)
[1-(4'-hydroxy-1',2'-butadienyl)cytosine] (Cytallene)
2'-β-methyl-ribofuranosyl nucleoside of Formula III:

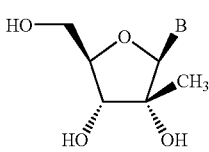

Formula III

Wherein B is selected from the group consisting of

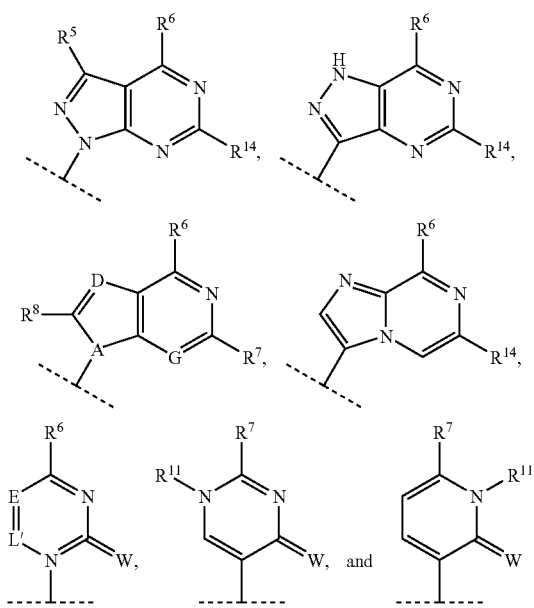

wherein:

A, G, and L' are each independently CH or N;

D is N, CH, C—CN, C—NO$_2$, C—C$_{1-3}$ alkyl, C—NHCONH$_2$, C—CONR$^{11}$R$^{11}$, C—CSNR$^{11}$R$^{11}$, C—COOR$^{11}$, C—C(=NH)NH$_2$, C-hydroxy, C—C$_{1-3}$ alkoxy, C-amino, C—C$_{1-4}$ alkylamino, C-di(C$_{1-4}$ alkyl)amino, C-halogen, C-(1,3-oxazol-2-yl), C-(1,3-thiazol-2-yl), or C-(imidazol-2-yl); wherein alkyl is unsubstituted or substituted with one to three groups independently selected from halogen, amino, hydroxy, carboxy, and C$_{1-3}$ alkoxy;

E is N or CR$^5$;

W is O or S;

R$^5$ is H, C$_{1-6}$ alkyl, C$_{2-6}$ alkenyl, C$_{2-6}$ alkynyl, C$_{1-4}$ alkylamino, CF$_3$, or halogen;

R$^6$ is H, OH, SH, NH$_2$, C$_{1-4}$ alkylamino, di(C$_{1-4}$ alkyl) amino, C$_{3-6}$ cycloalkylamino, halogen, C$_{1-4}$ alkyl, C$_{1-4}$ alkoxy, or CF$_3$;

R$^7$ is H, amino, C$_{1-4}$ alkylamino, C$_{3-6}$ cycloalkylamino, or di(C$_{1-4}$ alkyl)amino;

R$^8$ is H, halogen, CN, carboxy, C$_{1-4}$ alkyloxycarbonyl, N$_3$, amino, C$_{1-4}$ alkylamino, di(C$_{1-4}$ alkyl)amino, hydroxy, C$_{1-6}$ alkoxy, C$_{1-6}$ alkylthio, C$_{1-6}$ alkylsulfonyl, or (C$_{1-4}$ alkyl)$_{0-2}$ aminomethyl;

R$^{11}$ is H or C$_{1-6}$ alkyl;

R$^{14}$ is H, CF$_3$, C$_{1-4}$ alkyl, amino, C$_{1-4}$ alkylamino, C$_{3-6}$ cycloalkylamino, or di(C$_{1-4}$ alkyl)amino.

DETAILED DESCRIPTION OF THE INVENTION

The present invention is directed towards certain novel cyclic phosphate diesters of 1,3-propane-1-aryl diols having the trans-stereochemistry, their preparation and synthetic intermediates, and their use in the synthesis of prodrugs.

I. In One Aspect, Compounds of Formula I are Preferred

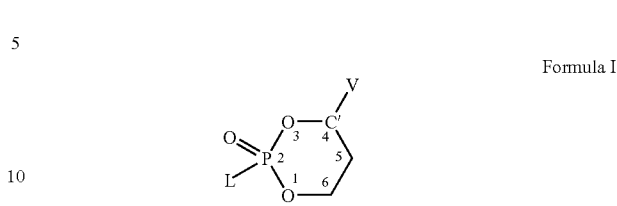

Formula I

V is selected from the group consisting of carbocyclic aryl, substituted carbocyclic aryl, heteroaryl, and substituted heteroaryl. In one aspect carbocyclic aryl and substituted carbocyclic aryl groups include phenyl and phenyl substituted with 1–4 substituents. In another aspect heteroaryl groups include monocyclic heteroaryl groups with 0–2 substituents. In another aspect, heteroaryl groups are 4-pyridyl, 3-pyridyl and 2-pyridyl. In another aspect carbocyclic groups are 3-chlorophenyl, 3-bromophenyl and 3,5-dichlorophenyl.

The group L is a leaving group selected from the group consisting of halogen, aryloxy, alkyl sulfonates, substituted-aryloxy groups, haloalkoxy, perhaloalkoxy, N-containing heteroaryl, and N-hydroxy-nitrogen containing-heteroaryl groups. In one aspect, leaving groups are halogen, aryl sulfonates and aryloxy groups substituted by 1 to 3 electron-withdrawing groups. In another aspect, leaving groups are halogens such as chloro or bromo, arylsulfonates such as 8-quinolylsulfonate or 2,4,6-trimethylphenylsulfonate and substituted-aryloxy groups such as chlorophenoxy, dichlorophenoxy or nitrophenoxy. In another aspect, leaving groups are 4-chlorophenoxy, 3,5-dichlorophenoxy, 4-nitrophenoxy, and 2,4-dichlorophenoxy.

In another aspect, V and L are trans relative to one another;

V is selected from the group consisting of carbocyclic aryl, substituted carbocyclic aryl, heteroaryl, and substituted heteroaryl. In one aspect carbocyclic aryl and substituted carbocyclic aryl groups include phenyl and phenyl substituted with 1–4 substituents. In another aspect heteroaryl groups include monocyclic heteroaryl groups with 0–2 substituents. In another aspect, heteroaryl groups are 4-pyridyl, 3-pyridyl and 2-pyridyl. In another aspect carbocyclic groups are 3-chlorophenyl, 3-bromophenyl and 3,5-dichlorophenyl.

The group L is a leaving group selected from the group consisting of halogen, aryloxy, alkyl sulfonates, substituted-aryloxy groups, haloalkoxy, perhaloalkoxy, N-containing heteroaryl, and N-hydroxy-nitrogen containing-heteroaryl groups. In one aspect, leaving groups are halogen, aryl sulfonates and aryloxy groups substituted by 1 to 3 electron-withdrawing groups. In another aspect, leaving groups are halogens such as chloro or bromo, arylsulfonates such as 8-quinolylsulfonate or 2,4,6-trimethylphenylsulfonate and substituted-aryloxy groups such as chlorophenoxy, dichlorophenoxy or nitrophenoxy. In another aspect, leaving groups are 4-chlorophenoxy, 3,5-dichlorophenoxy, 4-nitrophenoxy, and 2,4-dichlorophenoxy.

In another aspect, V and L are cis relative to one another;

V is selected from the group consisting of carbocyclic aryl, substituted carbocyclic aryl, heteroaryl, and substituted heteroaryl. In one aspect carbocyclic aryl and substituted carbocyclic aryl groups include phenyl and phenyl substituted with 1–4 substituents. In another aspect heteroaryl groups include monocyclic heteroaryl groups with 0–2 substituents. In another aspect, heteroaryl groups are 4-pyridyl, 3-pyridyl and 2-pyridyl. In another aspect carbocyclic groups are 3-chlorophenyl, 3-bromophenyl and 3,5-dichlorophenyl.

The group L is a leaving group selected from the group consisting of halogen, aryloxy, alkyl sulfonates, substituted-aryloxy groups, haloalkoxy, perhaloalkoxy, N-containing heteroaryl, and N-hydroxy-nitrogen containing-heteroaryl groups. In one aspect, leaving groups are halogen, aryl sulfonates and aryloxy groups substituted by 1 to 3 electron-withdrawing groups. In another aspect, leaving groups are halogens such as chloro or bromo, arylsulfonates such as 8-quinolylsulfonate or 2,4,6-trimethylphenylsulfonate and substituted-aryloxy groups such as chlorophenoxy, dichlorophenoxy or nitrophenoxy. In another aspect, leaving groups are 4-chlorophenoxy, 3,5-dichlorophenoxy, 4-nitrophenoxy, and 2,4-dichlorophenoxy.

Compounds of Formula I are either racemic, have the S configuration or the R configuration at carbon C'. In one aspect, compounds have an optical purity >95% ee with the S or R configuration at carbon C'.

II. Synthesis of Phosphorylating Agents

II.1 Synthesis of 1-(aryl)-Propane-1,3-Diols:

A variety of synthetic methods are known to prepare 1,3-diols. These suitable methods are divided into two types as following: 1) synthesis of racemic 1-(aryl)-propane-1,3-diol; 2) synthesis of enantioenriched 1-(aryl)-propane-1,3-diol.

II.1.1 Synthesis of Racemic 1-(aryl)-Propane-1,3-Diol:

1,3-Dihydroxy compounds can be synthesized by several well known methods from the literature. Substituted aromatic aldehydes are utilized to synthesize racemic 1-(aryl) propane-1,3-diol via addition of lithium enolate of alkyl acetate followed by ester reduction (path A) (Turner, *J. Org. Chem.* 55:4744 (1990)). Alternatively, aryl Grignard additions to 1-hydroxy propan-3-al also give 1-(arylsubstituted) propane-1,3-diols (path B). This method will enable conversion of various substituted aryl halides to 1-(arylsubstituted)-1,3-propane diols (Coppi, et al., *J. Org. Chem.* 53:911 (1988)). Aryl halides can also be used to synthesize 1-substituted propane diols by Heck coupling of 1,3-diox-4-ene followed by reduction and hydrolysis (Sakamoto, et al., *Tetrahedron Lett.* 33:6845 (1992)). Pyridyl, quinoline, isoquinoline propan-3-ol derivatives can be oxygenated to 1-substituted-1,3-diols by N-oxide formation followed by rearrangement in acetic anhydride conditions (path C) (Yamamoto, et al., *Tetrahedron* 37:1871 (1981)). A variety of aromatic aldehydes can also be converted to 1-substituted-1,3-diols by vinyl Grignard addition followed by hydroboration reaction (path D).

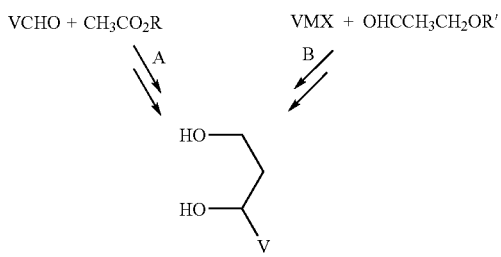

VCHO + CH$_3$CO$_2$R     VMX + OHCCH$_3$CH$_2$OR'

VCHO + CH$_2$=CHMX     VCH$_2$CH$_2$CH$_2$OH

V = Aryl, R = Alkyl, R' = benzyl, M = Mg or Li, X = Halide or null

II.1.2 Synthesis of Enantioenriched 1-(aryl)-Propane-1,3-Diol:

A variety of known methods for separation of secondary alcohols via chemical or enzymatic agents may be utilized for preparation of diol enantiomers (Harada, et al., *Tetrahedron Lett.* 28:4843 (1987)). Transition metal catalyzed hydrogenation of substituted 3-aryl-3-oxo propionic acids or esters is an efficient method to prepare R or S-isomers of beta hydroxy acids or esters in high enantiomeric purity (*Comprehensive Asymmetric Catalysis*, Jacobsen, E. N., Pfaltz, A., Yamamoto, H. (Eds), Springer, (1999); *Asymmetric Catalysis in organic Synthesis*, Noyori, R., John Wiley, (1994)). These beta hydroxy acid or ester products can be further reduced to give required 1-(aryl)-propane-1,3-diols in high ee. (path A). The β-keto acid or ester substrates for high pressure hydrogenation or hydrogen transfer reactions may be prepared by a variety of methods such as condensation of acetophenone with dimethylcarbonate in the presence of a base (Chu, et al., *J. Het Chem.* 22:1033 (1985)), by ester condensation (Turner, et al., *J. Org. Chem.* 54:4229 (1989)) or from aryl halides (Kobayashi, et al., *Tetrahedron Lett.* 27:4745 (1986)). Alternatively, 1,3-diols of high enantiomeric purity can be obtained by enantioselective borane reduction of β-hydroxyethyl aryl ketone derivatives or β-keto acid derivatives (path B) (Ramachandran, et al., *Tetrahedron Lett.* 38:761 (1997)). In another method, commercially available cinnamyl alcohols may be converted to epoxy alcohols under catalytic asymmetric epoxidation conditions. These epoxy alcohols are reduced by Red-Al to result in 1,3-diols with high ee's (path C) (Gao, et al., *J. Org. Chem.* 53:4081 (1980)). Enantioselective aldol condensation is another well described method for synthesis of 1,3-oxygenated functionality with high ee's starting from aromatic aldehydes. (path D) (Mukaiyama, *Org. React.* 28:203 (1982)).

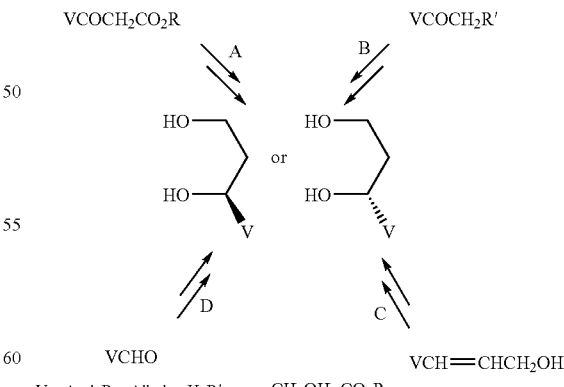

V = Aryl, R = Alkyl or H, R' = —CH$_2$OH, CO$_2$R

II.2 Synthesis of Phosphorylating Reagent

The general synthesis of the phosphorylating reagent is accomplished by reacting 1-aryl-3-propane diols with phosphorodichloridate of formula Cl$_2$P(O)-L. Phosphorodichloridate where L is aryloxy are synthesized by reacting substituted-phenols with phosphorusoxychloride (Rathore et al., *Indian J. Chem B* 32(10), 1066(1993)).

The enantioenriched activated phosphorylating agent is synthesized by phosphorylation of an enantioenriched 1-(V)-1,3-propane diol with phosphorodichloridates of formula L-P(O)Cl$_2$ in the presence of a base (Ferroni et al., *J. Org. Chem.* 64(13), 4943 (1999)). In one aspect, orders of addition include the addition of a solution of the diol and the base to a solution of the phosphorodichloridate in the chosen solvent. In another aspect, a solution of the diol and the base, and another solution containing the phosphorodichloridate in the same solvent or a different solvent, are added simultaneously to a chosen solvent. In another aspect, a solution of the diol is added to a solution of the phosphorus reagent followed by the addition of the base. Typical solvents for the phosphorylation of the diol are polar aprotic solvents that have low reactivity with phosphorodichloridates and solubilize the diol or the phosphorodichloridate. In one aspect, solvents to run the phosphorylation reaction are dichloromethane, THF, acetonitrile, pyridine, ,tetraalkylureas, trialkyl phosphates or hexaalkylphosphoramides. In another aspect, the solvents are dichloromethane, THF, acetonitrile, pyridine, DMPU, DMEU, tetramethyl urea, trimethyl phosphate, hexamethylphosphoramide. The reaction temperature is kept low, especially during the initial phase of the reaction, which is exothermic, so as to preserve the integrity of the reagents.

In one aspect, temperatures are below room temperature within −20° C. to 10° C. In one aspect, the exotherm is under control, the reaction temperature is brought slowly to room temperature to complete the formation of the phosphate reagent. In another aspect, the temperature is kept the same until completion of the reaction to preserve the integrity of the reagent. Due to the stereogenic nature of the phosphorus atom, reaction of the phosphorodichloridate with the diol under the reaction conditions described above gives a mixture of cis and trans isomers, slightly favoring the cis-isomer. Typical cis/trans ratios range from 50/50 to 60/40. The cis and trans isomers are separated by a combination of column chromatography and/or crystallization.

In one aspect of this invention, we found that when the isolated cis-isomer of the 4-nitrophenoxy phosphorylating agent was heated with a salt of 4-nitrophenol, >85% of the phosphorylating reagent isolated was the trans-isomer. In another aspect of this invention we found that when the isolated mixture of cis and trans isomers of the 4-nitrophenoxy phosphorylating reagent was heated with a salt of 4-nitrophenol, in the same solvent used for the phosphorylation step or another solvent, >85% of the phosphorylating reagent isolated was the trans-isomer. Furthermore, it was found that no prior isolation of the mixture was necessary to achieve the enrichment. As such, addition of the salt of the phenol-leaving group to the crude reaction mixture in which the aryloxy phosphorylating agent of the diol was generated accomplished the enrichment in the trans-isomer of Formula I, in the same ratio obtained when performing the enrichment on the isolated mixture of phosphorylating reagents. Similarly, when an equimolar mixture of cis and trans phosphorochloridate of compounds of Formula I was heated, only the trans isomer could be isolated. The phenoxide salt is generated by reacting the corresponding phenol with a base, preferably trialkylamines, nitrogen-containing heterocycles or sodium. In one aspect, bases are triethylamine, diisopropylethylamine, pyridine, DABCO, DBU, sodium hydride or an alkali metal. In another aspect, bases are triethylamine, DBU or the sodium salt of the phenoxide. The enrichment step can be run at room temperature but is generally heated to decrease reaction times, preferably in the range of 40° C. to 70° C. While the conversion of the aryloxy phosphorylating reagent requires the addition of the salt of the corresponding phenoxide, the conversion of phosphorochloridates of the enantioenriched diol do not necessitate the additional use of soluble chloride salts as the formation of the phosphorochloridate itself with the preferred bases generates two equivalents of chloride ion. In one aspect, upon completion of the phosphorylation of the diol, the reaction mixture is then heated, preferably in the range of 40° C. to 70° C., to completely convert the cis isomer into the trans isomer. In another aspect the temperature is kept the same as the one used for the addition of the reagents.

For the preparation of enantioenriched phosphorylating reagents from enantioenriched diols, preservation of the chirality at carbon C' in compounds of Formula I is critical. While for most enantioenriched diols epimerization of carbon C' was minimal, decrease in ee was observed with a few diols using the previously described reaction conditions. Especially troublesome were 1-(N-containing-heteroaryl)-1,3-propane diols where the initial ee of 98% for the diol was reduced to <85% in the isolated trans-phosphorylating reagent. In one aspect of this invention, it was discovered that the use of N-containing heteroaryl solvents maintained the ee of the trans-phosphorylating reagent above 95%. In one aspect, N-containing heteroaryl solvents are optionally substituted pyridines, quinolines, and pyrazines. In another aspect, N-containing heteroaryl solvents are optionally substituted pyridines. In another aspect, the N-containing heteroaryl solvent is pyridine. In an other aspect of the invention, it was discovered that formation of the salt of the 1-(N-containing-heteroaryl)-1,3-propane diol prior to addition of the phosphorodichloridate or phosphorusoxychloride and subsequent addition of the base helped prevent epimerization of the C' carbon without requiring the use of a N-containing heteroaryl solvents. In one aspect, salts of 1-(N-containing-heteroaryl)-1,3-propane diol are salts made by reacting 1-(N-containing-heteroaryl)-1,3-propane diol with an organic or mineral acid with a pka<2. In another aspect, salts are made with mineral acids with pka<1. In another aspect, salts are the hydrochloride and hydrobromide salts. The cis and trans isomers are separated by a combination of column chromatography and/or crystallization. However, it was found that after running the enrichment step, the isolation of the trans-isomer was greatly simplified yielding phosphorylating reagent of great purity, >95% trans-isomer and ee >95%. In one aspect the trans-phosphorylating reagent is isolated. In another aspect, the phsophorylating reagent is kept in solution and used for the phosphorylation of nucleosides without purification. The relative configuration of the phosphorus atom is determined by comparison of the $^{31}$P NMR spectra. The chemical shift of the equatorial phosphoryloxy moiety (trans-isomer) is more upfield than the one of the axial isomer (cis-isomer) (Verkade, et al., *J. Org. Chem.* 42, 1549 (1977)).

III. Use of the Phosphorylating Agents to Prepare Prodrugs

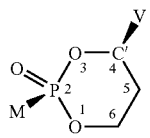

Formula II.A

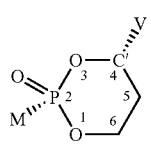

Formula II.B

The invention is also directed towards the use of the phosphorylating agents of Formula I for the synthesis of compounds of Formula II that are efficiently converted to the corresponding phosphate-containing compounds by P450 enzymes found in large amounts in the liver and other tissues containing these specific enzymes. As such the present invention is extremely useful in synthesizing cis-prodrugs of compounds effective in treating liver diseases or diseases where the liver is responsible for the overproduction of the biochemical end product such as glucose, cholesterol, fatty acids, and triglycerides. Such diseases include viral and parasitic infections, liver cancer, liver fibrosis, diabetes, hyperlipidemia, and obesity. In addition, the liver specificity of the prodrugs should also prove useful in the delivery of diagnostic agents to the liver.

In one aspect, the invention is directed towards the use of the phosphorylating agent for the synthesis of cis-prodrugs of the monophosphate of nucleosides and nucleoside analogs. Although the nucleoside or nucleoside analog can be attached to the phosphorus atom of the prodrug moiety through an oxygen, a nitrogen or a sulfur atom, in another aspect, the compound is attached to the phosphorus through an oxygen atom. In one aspect, the nucleoside or nucleoside analog is attached to the phosphorus atom of the prodrug moiety through a primary hydroxyl group. In another aspect, the prodrug moiety is attached to the 5'-hydroxyl of nucleoside or nucleoside analog.

In general it is preferred that M is attached via an oxygen in a primary hydroxyl group. In one aspect, MH is araA; AZT; d4T; ddI; ddA; ddC; L-ddC; L-FddC; L-d4C; L-Fd4C; 3TC; ribavirin; 5-fluoro-2'-deoxyuridine; FIAU; FIAC; BHCG; L-FMAU; BvaraU; E-5-(2-bromovinyl)-2'-deoxyuridine; TFT; 5-propynyl-1'-arabinofuranosyluracil; CDG; DAPD; FDOC; d4C; DXG; FEAU; FLG; FTC; L-dC; L-dT; 5-yl-carbocyclic-2'-deoxyguanosine; oxetanocin A; oxetanocin G; Cyclobut A; Cyclobut G; dFdC; araC; bromodeoxyuridine; IDU; CdA; FaraA; Coformycin; 2'-deoxycoformycin; araT; tiazofurin; ddAPR; 9-(arabinofuranosyl)-2,6-diaminopurine; 9-(2'-deoxyribofuranosyl)-2,6-diaminopurine; 9-(2'-deoxy-2'-fluororibofuranosyl)-2,6-diaminopurine; 9-(arabinofuranosyl)guanine; 9-(2'-deoxyribofuranosyl)guanine; 9-(2'-deoxy-2'-fluororibofuranosyl)guanine; FMDC; DMDC; 4'-thio-araC; 5,6 dihydro-5-azacytidine; 5-azacytidine; 5-aza-2'-deoxycytidine; AICAR; NK-84-0218; AM365; MCC478; ICN 2001; Fluor L and D nucleosides; Famciclovir; ACV; GCV; pen ciclovir; (R)-9-(3',4'-dihydroxybutyl)guanine, cytallene or 2'-β-methyl-ribofuranosyl nucleosides of Formula III:

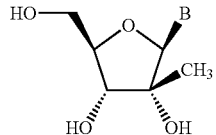

Formula III

Wherein B is selected from the group consisting of

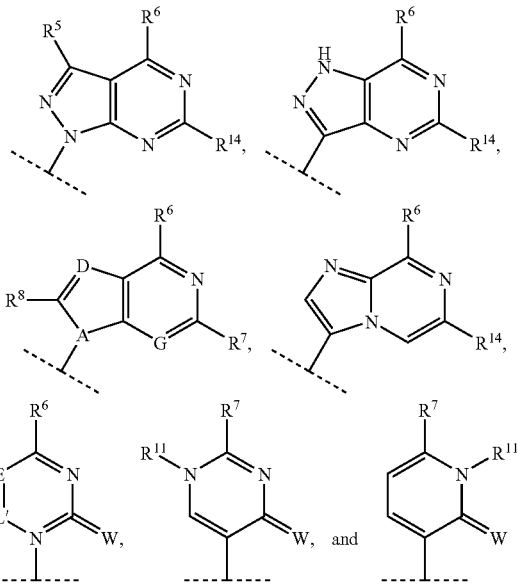

wherein:
A, G, and L' are each independently CH or N;
D is N, CH, C—CN, C—NO$_2$, C—C$_{1-3}$ alkyl, C—NH-CONH$_2$, C—CONR$^{11}$R$^{11}$, C—CSNR$^{11}$R$^{11}$, C—COOR$^{11}$, C—C(=NH)NH$_2$, C-hydroxy, C—C$_{1-3}$ alkoxy, C-amino, C—C$_{1-4}$ alkylamino, C-di(C$_{1-4}$ alkyl)amino, C-halogen, C-(1,3oxazol-2-yl), C-(1,3-thiazol-2-yl), or C-(imidazol-2-yl); wherein alkyl is unsubstituted or substituted with one to three groups independently selected from halogen, amino, hydroxy, carboxy, and C$_{1-3}$ alkoxy; E is N or CR$^5$;
W is O or S;
R$^5$ is H, C$_{1-6}$ alkyl, C$_{2-6}$ alkenyl, C$_{2-6}$ alkynyl, C$_{1-4}$ alkylamino, CF$_3$, or halogen;
R$^6$ is H, OH, SH, NH$_2$, C$_{1-4}$ alkylamino, di(C$_{1-4}$ alkyl) amino, C$_{3-6}$ cycloalkylamino, halogen, C$_{1-4}$ alkyl, C$_{1-4}$ alkoxy, or CF$_3$;
R$^7$ is H, amino, C$_{1-4}$ alkylamino, C$_{3-6}$ cycloalkylamino, or di(C$_{1-4}$ alkyl)amino;
R$^8$ is H, halogen, CN, carboxy, C$_{1-4}$ alkyloxycarbonyl, N$_3$, amino, C$_{1-4}$ alkylamino, di(C$_{1-4}$ alkyl)amino, hydroxy, C$_{1-6}$ alkoxy, C$_{1-6}$ alkylthio, C$_{1-6}$ alkylsulfonyl, or (C$_{1-4}$ alkyl)$_{0-2}$ aminomethyl;
R$^{11}$ is H or C$_{1-6}$ alkyl;
R$^{14}$ is H, CF$_3$, C$_{1-4}$ alkyl, amino, C$_{1-4}$ alkylamino, C$_{3-6}$ cycloalkylamino, or di(C$_{1-4}$ alkyl)amino.

In one aspect, compounds of Formula II are compounds wherein M is a nucleoside attached to the phosphorus atom via an oxygen atom that is in a primary hydroxyl group on a furanosyl group. In one aspect, such compounds include araA; AZT; d4T; ddI; ddA; ddC; L-ddC; L-FddC; L-d4C; L-Fd4C; 3TC; ribavirin; 5-fluoro-2'-deoxyuridine; FIAU; FIAC; BHCG; L-FMAU; BvaraU; E-5-(2-bromovinyl)-2'-deoxyuridine; TFT; 5-propynyl-1'-arabinofuranosyluracil; CDG; DAPD; FDOC; d4C; DXG; FEAU; FLG; FTC; L-dC; L-dT; 5-yl-carbocyclic-2'-deoxyguanosine; Oxetanocin A; Oxetanocin G; Cyclobut A; Cyclobut G; dFdC; araC; 5-bromodeoxyuridine; IDU; CdA; FaraA; Coformycin; 2'-deoxycoformycin; araT; tiazofurin; ddAPR; 9-(arabinofuranosyl)-2,6-diaminopurine; 9-(2'-deoxyribofuranosyl)-2,6-diaminopurine; 9-(2'-deoxy-2'-fluororibofuranosyl)-2,6-diaminopurine; 9-(arabinofuranosyl)guanine; 9-(2'-deoxyribofuranosyl)guanine; 9-(2'-deoxy-2'-fluororibofuranosyl)guanine; FMDC; DMDC; 4'-thio-araC; 5,6 dihydro-5-azacytidine; 5-azacytidine; 5-aza-2'-deoxycytidine; AICAR; NK-84-0218; AM365; MCC478; ICN 2001; Fluor L and D nucleosides, Famciclovir or 2'-β-methylribofuranosyl nucleosides of Formula III:

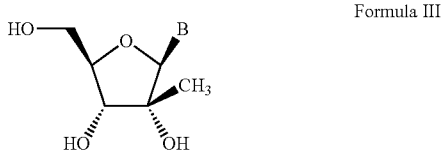

Formula III

Wherein B is selected from the group consisting of

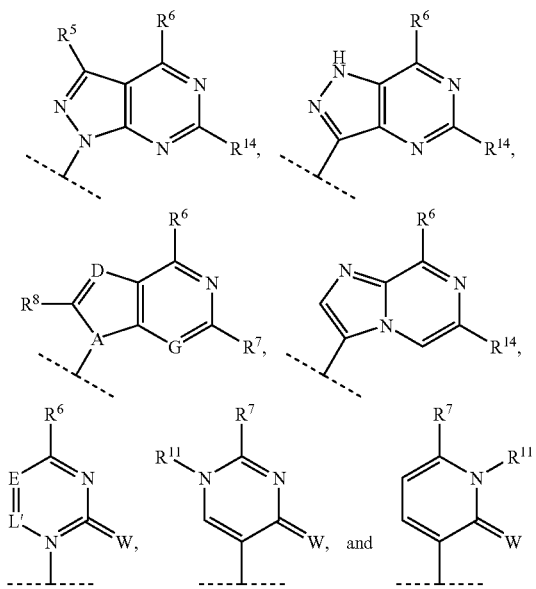

wherein:

A, G, and L' are each independently CH or N;

D is N, CH, C—CN, C—NO$_2$, C—C$_{1-3}$ alkyl, C—NH-CONH$_2$, C—CONR$^{11}$R$^{11}$, C—CSNR$^{11}$R$^{11}$, C—COOR$^{11}$, C—C(=NH)NH$_2$, C-hydroxy, C—C$_{1-3}$ alkoxy, C-amino, C—C$_{1-4}$ alkylamino, C-di(C$_{1-4}$ alkyl)amino, C-halogen, C-(1,3oxazol-2-yl), C-(1,3-thiazol-2-yl), or C-(imidazol-2-yl); wherein alkyl is unsubstituted or substituted with one to three groups independently selected from halogen, amino, hydroxy, carboxy, and C$_{1-3}$ alkoxy; E is N or CR$^5$;

W is O or S;

R$^5$ is H, C$_{1-6}$ alkyl, C$_{2-6}$ alkenyl, C$_{2-6}$ alkynyl, C$_{1-4}$ alkylamino, CF$_3$, or halogen;

R$^6$ is H, OH, SH, NH$_2$, C$_{1-4}$ alkylamino, di(C$_{1-4}$ alkyl) amino, C$_{3-6}$ cycloalkylamino, halogen, C$_{1-4}$ alkyl, C$_{1-4}$ alkoxy, or CF$_3$;

R$^{14}$ is H, CF$_3$, C$_{1-4}$ alkyl, amino, C$_{1-4}$ alkylamino, C$_{3-6}$ cycloalkylamino, or di(C$_{1-4}$ alkyl)amino;

R$^7$ is H, amino, C$_{1-4}$ alkylamino, C$_{3-6}$ cycloalkylamino, or di(C$_{1-4}$ alkyl)amino;

R$^{11}$ is H or C$_{1-6}$ alkyl;

R$^8$ is H, halogen, CN, carboxy, C$_{1-4}$ alkyloxycarbonyl, N$_3$, amino, C$_{1-4}$ alkylamino, di(C$_{1-4}$ alkyl)amino, hydroxy, C$_{1-6}$ alkoxy, C$_{1-6}$ alkylthio, C$_{1-6}$ alkylsulfonyl, or (C$_{1-4}$ alkyl)$_{0-2}$ aminomethyl.

In another aspect, M is attached via an oxygen in a hydroxyl group on an acyclic sugar. In another aspect, MH includes ACV, GCV, penciclovir, and (R)-9-(3',4'-dihydroxybutyl)guanine or cytallene.

III.1 Phosphorylation of Protected Nucleosides

For the synthesis of cis-prodrugs of Formula II, the prodrug moiety can be introduced at different stages of the synthesis. Most often the cyclic phosphates are introduced at a later stage, because of the general sensitivity of these groups to various reaction conditions. The synthesis can also proceed through using a protected or unprotected nucleoside or nucleoside analog depending on the reactivity of the functional groups present in the compound. Single stereoisomers of the cis-prodrugs can either be made by separation of the diastereoisomers/enantiomers by a combination of column chromatography and/or crystallization, or by enantiospecific synthesis using enantioenriched activated phosphate intermediates.

The general procedure for the phosphorylation of protected nucleosides is accomplished by reacting a suitably protected nucleoside with a base and reacting the alkoxide generated with the phosphorylating reagent. The protected nucleoside can be prepared by one skilled in the art using one of the many procedures described for the protection of nucleosides (Greene T. W., Protective Groups in Organic Chemistry, John Wiley & Sons, New York (1999)). The nucleoside is protected in such a way as to expose the hydroxyl group on which to add the phosphate group while protecting all the remaining hydroxyls and other functional groups on the nucleoside that may interfere with the phosphorylation step or lead to regioisomers. In one aspect, the protecting groups selected are resistant to strong bases, e.g., ethers, silyl ethers and ketals. In one aspect, the protecting groups are optionally substituted MOM ethers, MEM ethers, trialkylsilyl ethers and symmetrical ketals. In another aspect, the protecting groups are t-butyldimethylsilyl ether and isopropylidene. Further protection entails masking of the amino group of the base moiety, if present, so as to eliminate any acidic protons. In one aspect the selected N-protecting groups are selected from the groups of dialkyl formamidines, mono and dialkyl imines, mono and diaryl imines. In one aspect, the N-protecting groups are selected from the groups of dialkyl formamidines and mono-alkyl imine and mono aryl imine. In one aspect the mono-alkyl imine is benzylimine and the mono-aryl imine is phenylimine. In another aspect, the N-protecting group is a symmetrical dialkyl formamidine selected from the group of dimethyl formamidine and diethyl formamidine.

Generation of the alkoxide of the exposed hydroxyl group on the suitably protected nucleoside is accomplished with a base in an aprotic solvent that is not base sensitive such as THF, dialkyl and cylic formamides, ether, toluene and mixtures of those solvents. In one aspect, the solvents are DMF, DMA, DEF, N-methylpyrrolidine, THF, and mixture of those solvents.

Many different bases have been used for the phosphorylation of nucleosides and non-nucleoside compounds with cyclic and acyclic phosphorylating agents. For example trialkylamines such as triethylamine (Roodsari et al., *J. Org. Chem.* 64(21), 7727 (1999)) or diisopropylethylamine (Meek et al., *J. Am. Chem. Soc.* 110(7), 2317 (1988)); nitrogen containing heterocyclic amines such as pyridine (Hoefler et al., *Tetrahedron* 56(11), 1485 (2000)), N-methylimidazole (Vankayalapati et al., *J. Chem. Soc. Perk T* 1 14, 2187(2000)), 1,2,4-triazole (Takaku et al., *Chem. Lett.* (5), 699 (1986)) or imidazole (Dyatkina et al., *Tetrahedron Lett.* 35(13), 1961 (1994)); organometallic bases such as potassium t-butoxide (Postel et al., *J. Carbohyd. Chem.* 19(2), 171 (2000)), butyllithium (Tomeiro et al., *J. Org. Chem.* 62(18), 6344 (1977)), t-butylmagnesium chloride (Hayakawa et al., *Tetrahedron Lett.* 28(20), 2259 (1987)) or LDA (Aleksiuk et al., *J. Chem. Soc. Chem. Comm.* (1), 11 (1993)); inorganic bases such as cesium fluoride (Takaku et al., *Nippon Kagaku Kaishi* (10), 1968 (1985)), sodium hydride (Hanaoka et al., *Heterocycles* 23(11), 2927 (1985)), sodium iodide (Stromberg et al., *J. Nucleos. Nucleot.* 6(5), 815 (1987)), iodine (Stromberg et al., *J. Nucleos. Nucleot.* 6(5), 815 (1987)) or sodium hydroxide (Attanasi et al., *Phosphorus Sulfur* 35(1–2), 63 (1988)); metal such as copper (Bhatia et al., *Tetrahedron Lett.* 28(3), 271 (1987)). However, no reaction or racemization at the phosphorus stereogenic center was observed when coupling of phosphorylating reagent of Formula I was attempted using the previously described procedures. Especially, no reaction was observed with bases previously used with substituted cyclic phosphorylating agent to give the corresponding cyclic phosphate in high yield such as sodium hydride (Thuong et al., *Bull. Soc. Chim. Fr.* 667 (1974)), pyridine (Ayral-Kaloustian et al., *Carbohydr. Res.* 187(1991)), butyl-lithium (Hulst et al., *Tetrahedron Lett.* 1339 (1993)), DBU (Merckling et al., *Tetrahedron Lett.* 2217 (1996)), triethylamine (Hadvary et al., *Helv. Chim. Acta*, 1986, 69(8), 1862), N-methylimidazole (Li et al., *Tetrahedron Lett.* 6615 (2001)) or sodium methoxide (Gorenstein et al., *J. Am. Chem. Soc.* 5077 (1980)). In one aspect of this invention, it was found that the use of Grignard reagents promoted phosphorylation with minimal epimerization of the phosphorus center. In one aspect, Grignard reagents are alkyl and aryl Grignards. In another aspect, the Grignard reagents are t-butyl magnesium halides and phenyl magnesium halides. In another aspect, the Grignard reagents are t-butylmagnesium chloride and phenylmagnesium chloride.

In another aspect of the invention magnesium alkoxides are used to generate the magnesium 5'-alkoxide of the nucleoside. In one aspect magnesium alkoxides are selected from the group of $Mg(O-t-Bu)_2$, and $Mg(O-iPr)_2$.

In another aspect of this invention, Lewis acids can be added to the solution of the alkoxide, made with one of the bases previously described, to either exchange the carbocation of the alkoxide and/or modulate the reactivity of the formed alkoxide with the phosphorylating agent. Examples of Lewis acids include alkali salts, rare earth salts or transition metal salts. In one aspect, Lewis acids are magnesium salts, calcium salts, cesium salts, aluminum salts or cerium salts. In another aspect, Lewis acids are magnesium chloride, magnesium bromide and magnesium iodide.

In one aspect, the reaction conditions for the synthesis of compounds of Formula II encompass first the generation of the alkoxide with a Grignard reagent or, one of the other bases followed by addition of magnesium salts, second the addition of the phosphorylating reagent of Formula I to the solution of the nucleoside, either in solution, generally in the same solvent but not necessarily, or directly as a solid. In another aspect, the solution of the alkoxide is added to the solution of the phosphorylating reagent. In one aspect, temperatures for the generation of the alkoxide with a base are chosen from the range of −78° C. to 40° C. In one aspect, the temperatures are chosen from the range of −20° C. to 25° C. In another aspect, temperatures for the phosphorylation step are chosen from the range of −10° C. to 70° C. In another aspect, the temperatures are chosen from the range of 10° C. to 40° C.

The protected prodrugs generated as described above are then subjected to a deprotection step to remove all the protecting groups using one of the many methods known to those skilled in the art (Greene T. W., Protective Groups in Organic Chemistry, John Wiley & Sons, New York (1999)) and that are compatible with the stability of the phosphate prodrug. In one aspect, deprotection reagents include fluoride salts to remove silyl protecting groups, mineral or organic acids to remove acid labile protecting groups such as silyl and/or ketals and N-protecting groups, if present. In another aspect, reagents are TBAF, hydrochloric acid solutions and aqueous TFA solutions. Isolation and purification of the final prodrugs, as well as all intermediates, is accomplished by a combination of column chromatography and/or crystallization.

One aspect of the present invention provides methods to synthesize single isomers of compounds of Formula II. Due to the presence of a stereogenic center at the carbon where V is attached on the cyclic phosphate reagent, this carbon atom can have two distinct orientations, namely R or S. As such the trans-phosphate reagent can exist as either the S-trans or R-trans configuration and these two reagents are enantiomers. Therefore, an equal mixture of the R-trans and S-trans is a racemic mixture. In addition, because most nucleosides are chiral, phosphorylation of these nucleosides with a racemic trans-phosphate reagent will generate a mixture of two diastereomeric cis-prodrugs while phosphorylation of an achiral nucleoside analog (e.g., ACV) will generate a racemic mixture of cis-prodrugs. These compounds can be separated by a combination of column chromatography and/or crystallization. Alternatively, phosphorylation of the alkoxide of the nucleoside with an enantioenriched trans-phosphate reagent generates an enantioenriched cis-prodrug. As such reaction of the C'-S-trans-phosphate reagent generates the C'-S-cis-prodrug of the nucleoside while reaction with the C'-R-trans-phosphate reagent generates the C'-R-cis-prodrug.

In another aspect, depending on the rate of epimerization of the cis-phosphate reagent to the trans-phosphate reagent compared to the rate of reaction of the nucleoside with the trans-phosphate reagent, it was discovered that a cis-phosphorylating reagent still gives the cis-prodrug of a nucleoside. In that aspect, the cis-phosphorylating reagent epimerizes to the trans-phosphate reagent with the traces of the leaving group generated by the formation of small amounts of the prodrug. The nucleoside then reacts with the trans-phosphate reagent being generated in-situ giving the cis-prodrug. In another aspect, the nucleoside is reacted with a crude mixture of phosphorylating reagent to generate the cis-prodrug. In one aspect, the crude mixture of the phosphorylating reagent has been enriched in the trans-isomer. In another aspect the phosphorylating reagent is used without the enrichment step.

III.2 Phosphorylation of Unprotected Nucleosides

Alternatively, the prodrug of the nucleoside can be synthesized without prior protection of the nucleoside using reaction conditions that selectively phosphorylate primary hydroxyl groups. Selective 5'-acylation of nucleosides such as araC with acyl chlorides is well established (Gish et al., *J. Med. Chem.* 14, 1159 (1971)). However, because phosphorylating agents are considered to be more reactive, they presumably would give rise to less regioselectivity and lower yields, as well as reaction with the solvent used in the reaction (DMF). In one aspect of the invention, we found that reaction of a phosphorylating agent of Formula I with an unprotected nucleoside generated the 5'-cis-phosphate prodrug of the nucleoside in high yield, regioselectivity and stereoselectivity. In one aspect the isolated phosphorylating is added to a solution of the nucleoside. In another aspect the nucleoside is added to a solution of the phosphorylating reagent. Due to the poor solubility of unprotected nucleosides in common solvents and the potential reactivity of the solvent with the phosphorylating reagent, solvents with strong dielectric constants that have low reactivity with the phosphorylating reagent are necessary. Examples of such solvents are tetraalkylureas, trialkyl phosphates, or hexaalkylphosphoramides. In one aspect, the solvents are DMPU, tetramethyl urea, DMEU, trimethyl phosphate or hexamethylphosphoramide. Temperatures for the prodrug formation range from −20° C. to 40° C. depending on the stability of the reagents. In one aspect, the temperature for the phosphorylation of the nucleoside is kept between −10° C. and 10° C. In another aspect the temperature is kept between 0° C. and room temperature.

EXAMPLES

The compounds used in this invention and their preparation can be understood further by the examples, which illustrate some of the processes by which these compounds are prepared. These examples should not however be construed as specifically limiting the invention and variations of the compounds, now known or later developed, are considered to fall within the scope of the present invention as hereinafter claimed.

Compounds of Formula I-II are prepared according to the literature procedures with modifications and additions well understood by those skilled in the art. The TLC conditions given are utilizing plates of Analtech UNIPLATE, silica gel GHLF, scored 10×20 cm, 250 micron.

SYNTHESIS OF RACEMIC 1-(ARYL)PROPANE-1,3-DIOLS

Example 1

Preparation of 1-(2'-Furanyl)Propane-1,3-Diol via Grignard Addition and Hydroboration To a solution of 2-furaldehyde (3 g, 31.2 mmol) in THF (60 mL) was added 1 M vinyl magnesium bromide in THF (34 mL) at 0° C. After stirring for an hour, a solution of 1 M $BH_3$ THF complex in THF was added. The reaction was quenched with 3N NaOH (20 mL) and 30% hydrogen peroxide (10 mL) at 0° C. The organic fraction was separated and concentrated. The crude product was chromatographed by eluting with 5% methanol-dichloromethane to give 1-(2'-furyl)propane-1,3-diol (1 g, 22%).

Example 2

Preparation of 1-(2'-Pyridyl)Propane-1,3-Diol via Benzylic Oxidation

Step A: (*J. Org. Chem.* 22:589 (1957))

To a solution of 3-(2'-pyridyl)propane-1-ol (10 g, 72.9 mmol) in acetic acid (75 mL) was added 30% hydrogen peroxide slowly. The reaction mixture was heated to 80° C. for 16 h. The reaction was concentrated under vacuum and the residue was dissolved in acetic anhydride (100 mL) and heated at 110° C. overnight. Acetic anhydride was evaporated upon completion of the reaction. Chromatography of the mixture by eluting with methanol-methylene chloride (1:9) resulted in 10.5 g (60%) of pure diacetate.

Step B:

To a solution of diacetate (5 g, 21.1 mmol) in methanol-water (3:1, 40 mL) was added potassium carbonate (14.6 g, 105.5 mmol). After stirring for 3 h at room temperature, the reaction mixture was concentrated. The residue was chromatographed by eluting with methanol-methylene chloride (1:9) to give 2.2 g (68%) of crystalline diol.

Example 3

Preparation Of 1-(Aryl)-Propane-1,3-Diol from Propane-1,3-Diol via Grignard Addition Step A: (*J. Org. Chem.* 53:911 (1988))

To a solution of oxalyl chloride (5.7 mL, 97 mmol) in dichloromethane (200 mL) at −78° C. was added dimethyl sulfoxide (9.2 mL, 130 mmol). The reaction mixture was stirred at −78° C. for 20 min before addition of 3-(benzyloxy)propan-1-ol (11 g, 65 mmol) in dichloromethane (25 mL). After an hour at −78° C., reaction was quenched with triethylamine (19 mL, 260 mmol) and warmed to room temperature. Work-up and column chromatography by elution with dichloromethane resulted in 8 g (75%) of 3-(benzyloxy)propan-1-al.

Step B:

To a solution of 3-(benzyloxy)propan-1-al (1 g, 6.1 mmol) in THF at 0° C. was added a 1 M solution of 4-fluorophenylmagnesium bromide in THF (6.7 mL, 6.7 mmol). The reaction was warmed to room temperature and stirred for 1 h. Work-up and column chromatography by elution with dichloromethane resulted in 0.7 g (44%) of alcohol.

Step C:

To a solution of benzyl ether (500 mg) in ethyl acetate (10 mL) was added 10% Pd(OH)$_2$C (100 mg). The reaction was stirred under hydrogen gas for 16 h. The reaction mixture was filtered through celite and concentrated. Chromatography of the residue by elution with ethyl acetate-dichloromethane (1:1) resulted in 340 mg (79%) of product.

Example 4

General Procedure for Preparation of 1-Aryl Substituted Propane-1,3-Diol From Aryl Aldehyde Step A: (*J. Org. Chem.* 55:4744 (1990))

To a −78° C. solution of diisopropylamine (2 mmol) in THF (0.7 ml/mmol diisopropylamine) was slowly added n-butyllithium (2 mmol, 2.5 M solution in hexanes). The reaction was then stirred for 15 min at −78° C. before a solution of ethyl acetate (2 mmol) in THF (0.14 ml/mmol ethyl acetate) was slowly introduced. After stirring an additional 30 min at −78° C., a THF solution containing the aryl aldehyde (1.0 mmol in 0.28 ml THF) was added. The reaction was then stirred at −78° C. for 30 min, warmed to room temperature and stirred an additional 2 h. After aqueous work up (0.5 M HCl), the organic layer was concentrated to a crude oil (beta-hydroxyester).

Step B:

The crude hydroxyester was dissolved in ether (2.8 ml/mmol), cooled to ice bath temperature, and lithium aluminum hydride (3 mmol) was added batch wise. The reaction was stirred allowing the cooling bath to melt and the reaction to reach room temperature. After stirring overnight at room temperature, the reaction was cooled back to ice bath temperature and quenched with ethyl acetate. Aqueous work up (0.5 M HCl) afforded the crude diol, which was purified either by chromatography or distillation.

Example 4a

Synthesis of 1-(3-methoxycarbonylphenyl)-1,3-propane diol 1-(3-bromophenyl)-1,3-propane diol was prepared as Example 4 and further derivatized as follows:

A pressure vessel was charged with 1-(3-bromophenyl)-1,3-propane diol (2 g, 8.6 mmol), methanol (30 mL), triethylamine (5 mL) and bis(triphenylphosphine)palladium dichloride (0.36 g, 05 mmol). The sealed vessel was pressurize with carbon monoxide at 55 psi and heated at 85° C. for 24 h. The cooled vessel was opened and the reaction mixture was filtered through Celite® and rinsed with methanol. The combined filtrates were concentrated under reduced pressure and the residue was purified by column chromatography (silica gel, hexanes/ethyl acetate 1/1) to afford the title compound (1.2 g, 66%)

TLC: hexanes/ethyl acetate 2/8; Rf=0.5

$^1$H NMR (CDCl$_3$, Varian Gemini 200 MHz): 5.05–4.95 (m, 1H), 3.9 (s, 3H), 2–1.8 (m, 2H).

Example 4b

Synthesis of 1-(4-methoxycarbonylphenyl)-1,3-propane diol 1-(4-bromophenyl)-1,3-propane diol was prepared as Example 4 and further derivatized as Example 4a.

TLC: hexanes/ethyl acetate 3/7; Rf=0.35

$^1$H NMR (CDCl$_3$, Varian Gemini 200 MHz): 5.1–5 (m, 1H), 3.91 (s, 3H), 2.05–1.9 (m, 2H).

SYNTHESIS OF ENANTIOENRICHED 1-(ARYL)-PROPANE-1,3-DIOLS

Example 5

General Procedure for Resolution of Racemic 1,3-diols

Racemic diols synthesized as in Examples 1–4 may be resolved to yield both entaniomers as described in the following procedure.

Step A:

To a solution of diol (1.0 mmole) in THF (1.0 ml) was added hexamethyldisilazide (2.1 mmole) followed by a catalytic amount of trimethylsilyltriflate (2–3 drops). After stirring at room temperature for 1 h, the reaction was diluted with hexane (4 ml) and subjected to work up with ice-cold water. The resulting disilylether was either purified by chromatography or, if sufficiently pure, used crude in the next reaction.

Step B:

To a solution of disilylether (1.0 mmole) and (−)-menthone (1.1 mmole) in dichloromethane (2.0 ml) at −40° C., was slowly added trimethylsilyltriflate (0.11 mmole). The reaction was then kept at −50° to −60° C. for 48 h, at which time pyridine was added to quench the reaction. After warming to room temperature, the crude mixture was diluted with hexane (4.0 ml) and subjected to aqueous work up. The two ketals were separated by chromatography.

Step C:

The separated ketals were hydrolyzed by adding a catalytic amount of concentrated hydrochloric acid to a methanol (4.0 ml/mmole) solution of each. After stirring overnight at room temperature, the methanol was removed under vacuum and the residue was subjected to aqueous work up. The resolved diols were further purified by either chromatography or distillation.

Example 6

Synthesis of Enantioenriched 1-(3'-Chlorophenyl)-1,3-Dihydoxypropane via Sharpless Asymmetric Epoxidation Step A:

To a dispersion of m-chloro-cinnamicacid (25 g, 137 mmol) in ethanol (275 mL) was added conc. sulfuric acid (8 mL) at room temperature. The reaction was refluxed overnight and concentrated. Ice-cold water was added to the crude and precipitated white solid was filtered and washed with cold water. The precipitate was dried under vacuum overnight to give 25 g (87%) of ester. (Rf=0.5 in dichloromethane on silica)

Step B:

To a solution of m-ethylchlorocinnamate (23 g, 109.5 mmol) in dichloromethane at −78° C. was added 1 M DIBAL-H in dichloromethane (229 mL, 229 mmol) dropwise over 1 h. The reaction was stirred at −78° C. for an additional 3 h. Ethylacetate was added to quench excess DIBAL-H and saturated aq. Potassium sodium tartrate was added and the reaction was stirred at room temperature for 3 h. The organic layer was separated and salts were washed with ethyl acetate. The combined organic extracts were concentrated and distilled at 120° C./0.1 mm to give 14 g (76%) of pure allylic alcohol. (Rf=0.38 in 1:1 ethylacetate: hexane on silica)

Step C:

To a solution of m-chlorocinnamyl alcohol (5 g, 29.76 mmol) in dichloromethane (220 mL) was added activated 4 Å molecular sieves powder (2.5 g) and the mixture was cooled to −20° C. (+)-Diethyl tartrate (0.61 mL, 3.57 mmol) was added at −20° C. and stirred for 15 min before adding titanium tetraisopropoxide (0.87 g, 2.97 mmol). The reaction was stirred for additional 30 min and 5–6 M solution of t-butylhydroperoxide in heptane (10 mL, 60 mmol) was added dropwise while maintaining the internal temperature at −20 to −25° C. The mixture was stirred for an additional 3 h at −20° C. and a 10% sodium hydroxide in saturated aq.

sodium chloride (7.5 mL) followed by ether (25 mL) were added. The reaction was warmed to 10° C. and stirred for 15 min before adding anhydrous magnesium sulfate (10 g) and celite® (1.5 g). The mixture was further stirred for additional 15 min, filtered and concentrated at 25° C. to give crude epoxy alcohol. (Rf=0.40 in 1:1 ethylacetate:hexane on silica)

Step D:

To a solution of crude m-chloroepoxycinnamyl alcohol obtained from earlier reaction in dimethoxyethane (300 mL) was added a 65% Red-Al solution in toluene (18.63 mL, 60 mmol) dropwise under nitrogen at 0° C. After stirring at room temperature for three hours, the solution was diluted with ethyl acetate (400 mL) and quenched with aq. saturated sodium sulfate solution (50 mL). After stirring at room temperature for 30 min, the resulting white precipitate formed was filtered and washed with ethylacetate. The filtrate was dried and concentrated. The crude product was distilled at 125–130° C./0.1 mm to give 3.75 g (67%) of enantioenriched (R)-1-(3'-chlorophenyl)-1,3-dihydoxypropane. (Rf=0.40 in 1:1 ethylacetate:dichloromethane)

Enantiomeric excesses were defined as diacetates (prepared by treatment of diols with acetic anhydride, triethylamine, cat.DMAP in dichloromethane) by HPLC ((S,S) Whelko-0, 250 cm×4.0 mm ID purchased from Regis).

(R)-1-(3'-chlorophenyl)-1,3-dihydoxypropane: 91% ee (+)Diisopropyltartrate provided >96% ee in (R)-1-(3'-chlorophenyl)-1,3-dihydoxypropane.

(S)-1-(3'-Chlorophenyl)-1,3-dihydoxypropane was also prepared under identical conditions via asymmetric epoxidation and reduction protocol utilizing (−)-tartrate in similar yields. (S)-3-(3'-Chlorophenyl)-1,3-dihydoxypropane was obtained with 79% ee.

Example 7

Synthesis of Enantioenriched 1-(3'-Chlorophenyl)-1,3-Dihydoxypropane via Hydrogen Transfer Reaction Step A: Preparation of Methyl 3-(3'-Chlorophenyl)-3-Oxo-Propanoate:

A 22 L, 3-neck round bottom flask was equipped with a mechanical stirrer, thermowell/thermometer and nitrogen inlet (bubbler in-line). The flask was flushed with nitrogen and charged sequentially with THF (6 L), potassium t-butoxide (1451 g), and THF (0.5 L). The resulting mixture was stirred at ambient temperature for 15 minutes and a 20° C. water bath was applied. A 3 L round bottom flask was charged with 3'-chloroacetophenone (1000 g) and diethylcarbonate (1165 g), and the resulting yellow solution was added slowly to the stirred potassium t-butoxide solution, maintaining the temperature between 16 and 31° C. After the addition was complete (1 h, 10 min.), the cooling bath was removed and the solution was stirred for 1 h, 30 min. TLC indicated that the reaction was complete. A 5 gallon stationary separatory funnel was charged with ice water (4 L) and concentrated hydrochloric acid (1.3 L of 12 M solution). The dark red reaction solution was quenched into the aqueous acid and the mixture was stirred for 15 minutes. The layers were separated and the aqueous phase (lower) was extracted again with toluene (4 L). The combined organic extracts were washed with saturated brine (2×3 L, 10 minute stirring time each), dried (MgSO₄), filtered and concentrated under reduced pressure to provide 1480 g of a brown oil. The oil was placed under high vacuum (10 torr) overnight to give 1427 g. The material was vacuum distilled (short path column, fraction cutter receiver) and the fraction at 108–128° C./1–0.5 torr was collected to provide 1273.9 g of a yellow oil (92.6%). (Rf=0.36 in 20% ethyl acetate/hexanes).

Step B: Preparation of Methyl (S)-3-(3'-Chlorophenyl)-3-Hydroxypropionate:

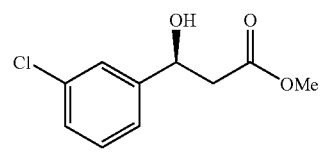

A 12 L, 3-neck round bottom flask was equipped with a mechanical stirrer, thermometer, addition funnel (500 mL) and nitrogen inlet (bubbler in-line). The flask was flushed with nitrogen and charged with formic acid (292 mL, 350 g). Triethylamine (422 mL, 306 g) was charged to the addition funnel, then added slowly with stirring, maintaining the temperature <45° C. After the addition was complete (1 h, 30 min.), the solution was stirred with the ice bath applied for 20 min., then at ambient temperature for an additional 1 h. The flask was charged sequentially with methyl 3-(3-chlorophenyl)-3-oxo-propanoate (1260 g), DMF (2.77 L including rinsing volume) and (S,S)-Ts-DPEN-Ru-Cl-(p-cymene) (3.77 g). The flask was equipped with a heating mantle and the addition funnel was replaced with a condenser (5 C circulating coolant for condenser). The stirred reaction solution was slowly heated to 60° C. (90 min. to attain 60 C) and the contents were maintained at 60° C. for 4.25 h. HPLC indicated 3% starting material remained. The solution was stirred at 60 C for an additional 8 h, then gradually cooled to ambient temperature overnight. HPLC indicated 0.5% starting material. A 5 gallon stationary separatory funnel was charged with water (10 L) and MTBE (1 L). The reaction solution was poured into the aqueous mixture and the reaction flask was rinsed into the separatory funnel with an additional 1 L of MTBE. The contents were stirred for several minutes and the layers were separated. The aqueous phase was extracted with additional MTBE (2×1 L), and the combined organic extracts were washed with brine (1 L), and concentrated under reduced pressure to provide 1334 g of a red oil (105%). The oil was used without further purification for the next step.

The crude hydroxyester (10 mg, 0.046 mmol) was dissolved in dichloromethane (1 mL). Acetic anhydride (22 μL, 0.23 mmol) and 4-(dimethylamino)pyridine (22 mg, 0.18 mmol) were added and the solution was stirred at ambient temperature for 15 min. The solution was diluted with dichloromethane (10 mL) and washed with 1 M hydrochloric acid (3×3 mL). The organic phase was dried (MgSO₄), filtered and concentrated under reduced pressure. The residual oil was dissolved in methanol and analyzed by chiral HPLC (Zorbax Rx-C18, 250×4.6 mm; mobile phase: 65/35 (v/v) water/acetonitrile, isocratic; flow rate=1.5 mL/min; inj. volume=15 μL; UV detection at 220 nm. Retention times: Product=9.3 min, starting material=17.2 min.). The hydroxyester was derivatized to the acetate for analysis by chiral HPLC and shown to give 91% ee. (HPLC conditions: Column: Pirkle covalent (S,S) Whelk-O 10/100 krom FEC, 250×4.6 mm; mobile phase: 70/30 (v/v) methanol/water, isocratic; flow rate: 1.5 mL/min; inj. volume=10

μL; UV detection at 220 nm. Retention times: S-hydroxyester (acetate)=9.6 min, R-hydroxyester (acetate)=7.3 min.)

Step C: Preparation of (S)-3-(3'-Chlorophenyl)-3-hydroxypropanoic acid:

To the crude hydroxyester in a 10 L rotary evaporator flask was added sodium hydroxide solution (2.5 L of 2 M solution). The resulting solution was stirred on the rotary evaporator at ambient pressure and temperature for 2 h. HPLC indicated 5% starting material still remained (HPLC conditions: Column: Zorbax Rx-C18, 250×4.6 mm; mobile phase: 65/35 (v/v) water/acetonitrile, isocratic; flow rate=1.5 mL/min; inj. volume=15 μL; UV detection at 220 nm. Retention times: Product=3.8 min, starting material=18.9 min.). The pH of the solution was 11 (wide range pH paper). Additional 2 M NaOH solution was added to adjust the pH to 14 (approx. 100 mL), and the solution was stirred for an additional 30 min. HPLC indicated the reaction was complete. The solution was transferred to a 5 gallon stationary separatory funnel and extracted with MTBE (2 L). The layers were separated and the organic extract was discarded. The aqueous phase was transferred back to the separatory funnel and acidified with 12 M HCl solution (600 mL). The mixture was extracted with MTBE (1×2 L, 2×1 L). The combined acidic organic extracts were dried (MgSO₄), filtered and concentrated under reduced pressure to give 1262 g of a brown, oily semi-solid. The residue was slurried with ethyl acetate (1 L) and transferred to a 12 L, 3-neck round bottom flask equipped with a mechanical stirrer, heating mantle, condenser and thermometer. The stirred mixture was heated to dissolve all solids (28° C.) and the dark solution was cooled to 10° C. (a precipitate formed at 11° C.). The mixture was slowly diluted with hexanes (4 L over 1 h) and the resulting mixture was stirred at <10° C. for 2 h. The mixture was filtered and the collected solid was washed with cold 4/1 hexanes/ethyl acetate (1 L), and dried to constant weight (−30 in. Hg, 50° C., 4 h). Recovery=837 g of a beige solid (70.4%). mp=94.5–95.5° C.

A 50 mg sample of hydroxyacid was reduced to the diol with borane-THF (see Step D). The resulting crude diol was diacetylated (as described in Step B)) and analyzed by chiral HPLC. Retention times: S-diol (diacetate)=12.4 min, R-diol (diacetate)=8.8 min.) ee=98%

A second crop of hydroxyacid was isolated. The filtrate from above was concentrated under reduced pressure to give 260 g of a brown sludge. The material was dissolved in ethyl acetate (250 mL) and the stirred dark solution was slowly diluted with hexanes (1000 mL) and the resulting mixture was stirred at ambient temperature overnight. The mixture was filtered and the collected solid was washed with 5/1 hexanes/ethyl acetate (200 mL), and dried to constant weight (−30 in. Hg, 50° C., 16 h). Recovery=134 g of a beige solid (11.2%). ee=97%

Step D: Preparation of (S)-(−)-1-(3-Chlorophenyl)-1,3-Propanediol:

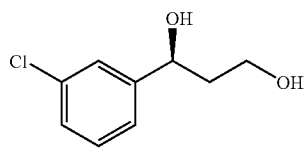

A 22 L, 3-neck round bottom flask was equipped with a mechanical stirrer, thermowell/thermometer and nitrogen inlet (outlet to bubbler). The flask was charged with 2 M borane-THF (3697 g, 4.2 L) and the stirred solution was cooled to 5° C. A solution of (S)-3-(3-chlorophenyl)-3-hydroxypropanoic acid (830 g) in THF (1245 mL) was prepared with stirring (slightly endothermic). The reaction flask was equipped with an addition funnel (1 L) and the hydroxyacid solution was slowly added to the stirred borane solution, maintaining the temperature ≦16° C. After the addition was complete (3 h), the mixture was stirred at ice bath temperature for 1.5 h. The reaction was quenched by careful addition of water (2.5 L). After the addition was complete (30 min), 3 M NaOH solution (3.3 L) was added (temperature increased to 35° C.) and the resulting mixture was stirred for an additional 20 minutes (temperature=30° C.). The reaction mixture was transferred to a 5 gallon stationary separatory funnel and the layers were separated. The aqueous phase was extracted with MTBE (2.5 L) and the combined organic extracts (THF and MTBE) were washed with 20 wt % NaCl solution (2 L) and stirred with MgSO₄ (830 g) for 30 minutes. The mixture was filtered through Celite® and concentrated under reduced pressure to provide 735 g of a thick, brown oil.

The oil was purified by vacuum distillation and the fraction at 135–140° C./0.2 mm Hg was collected to provide 712.2 g of a colorless oil (92.2%).

The diol was diacetylated and analyzed by chiral HPLC (e.e.=98%) (see Step B). Retention times: S-diol (diacetate) =12.4 min, R-diol (diacetate)=8.9 min. [α]_D=−51.374 (5 mg/mL in CHCl₃)

Example 8

Synthesis of Enantioenriched 1-(4'-pyridyl)-1,3-Dihydoxypropane via Hydrogen Transfer Reaction Step A: Synthesis of methyl 3-oxo-3-(pyridin-4-yl)-propanoate A 50 L, 3-neck flask was equipped with an overhead stirrer, heating mantle, and nitrogen inlet. The flask was charged with THF (8 L), potassium t-butoxide (5 kg, 44.6 mol), and THF (18 L). 4-Acetylpyridine (2.5 kg, 20.6 mol) was added, followed by dimethylcarbonate (3.75 L, 44.5 mol). The reaction mixture was stirred without heating for 2.5 h then with heating to 57–60° C. for 3 h. The heat was turned off and the mixture cooled slowly overnight (15 h). The mixture was filtered through a 45 cm Buchner funnel. The solid was returned to the 50 L flask and diluted with aqueous acetic acid (3 L acetic acid in 15 L of water). The mixture was extracted with MTBE (1×16 L, 1×12 L). The combined organic layers were washed with aqueous Na₂CO₃ (1750 g in 12.5 L water), saturated aqueous NaHCO₃ (8 L), and brine (8 L) then dried over MgSO₄ (500 g) overnight (15 h). The solution was filtered and the solvent removed by rotary evaporation to a mass of 6.4 kg. The resulting suspension was cooled in an ice bath with stirring for 2 h. The solid was collected by filtration, washed with MTBE (500 mL), and dried in a vacuum oven at 20° C. for 15 h, giving 2425 g (66% yield) of the keto ester as a pale yellow solid.

The MTBE mother liquor was concentrated to approximately 1 L. The resulting suspension was cooled in an ice bath for 1 h. The solid was collected by filtration, washed with MTBE (2×150 mL), and dried in a vacuum oven to give 240 g (6%) of a second crop.

TLC. Merck silica gel plates, 1:2 THF/hexane, UV lamp, Rf of SM=0.25, Rf of product=0.3.

Melting Point: 74–76° C.

Step B: Synthesis of S-Methyl-3-Hydroxy-3-(pyridin-4-yl)-propanoate

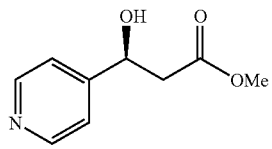

A 22 L, 3-neck round bottom flask was equipped with an overhead stirrer, thermowell/thermometer, addition funnel (1 L), and cooling vessel (empty). The flask was flushed with nitrogen, charged with formic acid (877 g) and cooled with an ice bath. Triethylamine (755 g) was charged to the addition funnel and added slowly over 50 minutes to the stirred formic acid. After the addition was complete, the cooling bath was removed and the reaction solution was diluted with DMF (5.0 L). The ketoester (2648 g) was added in one portion, followed by an additional 0.5 L of DMF. The flask was equipped with a heating mantle and the stirred mixture was heated gradually to 16° C. to dissolve all solids. The catalyst (S,S)-Ts-DPEN-Ru-Cl-(p-cymene) (18.8 g) was added in one portion and the stirred mixture was heated to 55° C. over 1 h. The resulting dark solution was stirred at 55° C. for 16 h. TLC indicated the reaction was complete. The solvent was evaporated under reduced pressure (Buchi R152 rotary evaporator under high vacuum, bath temp=60° C.) to give 3574 g of a brown oil. The oil was dissolved in dichloromethane (10 L) and transferred to a 5 gal. stationary separatory funnel. The dark solution was washed with saturated sodium bicarbonate solution (3.0 L) and the aqueous phase was back extracted with dichloromethane (3.0 L). The combined dichloromethane extracts were dried over MgSO$_4$ (300 g), filtered, and concentrated under reduced pressure to provide 3362 g of a brown oil (125% of theoretical, contains DMF by $^1$HNMR).

Column: Chiralpak AD, 0.46×25 cm; mobile phase=10:90, ethanol:hexane, isocratic; flow rate=1.5 mL/min; injection volume=10 µL UV detection at 254 nm.

Retention times: R hydroxy ester=19.9 min.
S hydroxy ester=21.7 min.
Retention times: R diol=14.2 min.
S diol=15.5 min
Hydroxy Ester:
$^1$H NMR (CDCl$_3$): δ 2.73 (d, 2H, J=1.5 Hz), 3.73 (s, 3H), 4.35 (s, 1H), 5.11–5.19 (m, 1H), 7.31 (d, 2H, J=6.6 Hz), 8.53 (d, 2H, J=6.0 Hz)

Merck silica gel 60 plates, 2.5×7.5 cm, 250 micron; UV lamp: 5% MeOH in CH$_2$Cl$_2$; Rf of S.M.=0.44, Rf of product=0.15.

e.e.=87% S isomer of hydroxy ester.

Step C: Synthesis of S-(−)-1-(Pyrid-4-yl)-1,3-propanediol

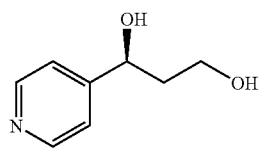

A 22 L, 4-neck round bottom flask was equipped with an overhead stirrer, thermowell/thermometer, addition funnel (2 L), condenser and cooling vessel (empty). The flask was flushed with nitrogen and charged sequentially with sodium borohydride (467 g, 12.3 mol), 1-butanol (9.0 L), and water (148 mL, 8.23 mol) The crude hydroxyester was dissolved in 1-butanol (1.0 L) and the solution was charged to the addition funnel. The solution was added over 3.25 h, using cooling as necessary to keep the temperature below 62 C. After addition was complete, the mixture was stirred for 0.5 h then the flask was equipped with a heating mantle and the stirred mixture was heated to 90 C over 0.75 h. The mixture was stirred at 90–93 C for 2.25 h, then cooled over 1.5 h to 28 C. The reaction mixture was quenched with aqueous potassium carbonate solution (10 wt/vol %, 6 L) and the mixture was stirred for 10 minutes. The layers were separated and the butanol phase was washed with aqueous potassium carbonate solution (10 wt/vol %, 2 L) and sodium chloride solution (15 wt/vol %, 2 L). The solvent was removed under reduced pressure (Buchi R152 rotary evaporator, high vacuum, bath temperature=60 C) until a concentrated solution resulted and 10.5 L of distillate had been collected. Acetonitrile (3 L) was fed into the evaporator flask and the solvent was evaporated under reduced pressure. Acetonitrile (9 L) was again fed into the evaporator flask and the slurry was stirred (rotation on the rotary evaporator) at ~60 C (bath temperature=70 C, atmospheric pressure) for 15 minutes. The hot slurry was filtered through Celite® 521 (250 g as a slurry in 1 L of acetonitrile was prepacked on a 24 cm Buchner funnel). The filtrate was partially concentrated under reduced pressure (5 L of distillate were collected) and the resulting slurry was heated at atmospheric pressure on the rotary evaporator to dissolve all solids (bath temp=65 C). The heat source was turned off and the resulting solution was stirred on the rotary evaporator for 10 h, with gradual cooling to ambient temperature. The resulting mixture was filtered and the collected solid was washed with acetonitrile (2×200 mL) and dried to constant weight (−30 in. Hg, 55° C., 4 h), giving S-(−)-1-(4-pyridyl)-1,3-propanediol as a yellow solid weighing 496 g (39% yield).

Melting point=98–100° C.
HPLC conditions:
Column: Chiralpak AD, 0.46×25 cm; mobile phase=10:90, ethanol:hexane, isocratic; flow rate=1.5 mL/min; injection volume=10 µL UV detection at 254 nm.

Retention times: R diol=14.2 min.
S diol=15.5 min.

Merck silica gel 60 plates, 2.5×7.5 cm, 250 micron; UV lamp; 15% MeOH in CH$_2$Cl$_2$; Rf of starting material=0.38, Rf of product=0.17, Rf of boron complex=0.26.

Example 9

Synthesis of (S)-3-(3'-chlorophenyl)-1,3-dihydroxypropane via (−)-β-chlorodiisopinocampheylborane (DIPCl) Reduction Step A: Preparation of 3-(3-chlorophenyl)-3-oxo-propanoic acid:

A 12 L, 3-neck round bottom flask was equipped with a mechanical stirrer and addition funnel (2 L). The flask was flushed with nitrogen and charged with diisopropylamine (636 mL) and THF (1.80 L). A thermocouple probe was immersed in the reaction solution and the stirred contents were cooled to −20° C. n-Butyllithium (1.81 L of a 2.5 M solution in hexanes) was charged to the addition funnel and added slowly with stirring, maintaining the temperature between −20 and −28° C. After the addition was complete (30 min), the addition funnel was rinsed with hexanes (30 mL) and the stirred solution was cooled to −62° C. Trimethylsilyl acetate (300 g) was added slowly with stirring, maintaining the temperature <−60° C. After the addition was complete (30 min), the solution was stirred at −60° C. for 15 min. 3-Chlorobenzoyl chloride (295 mL) was added slowly with stirring, maintaining the temperature <−60° C. After the addition was complete (65 min), the cooling bath was removed and the reaction solution was stirred for 1.25 h, with gradual warming to 0° C. The reaction flask was cooled with an ice bath, then water (1.8 L) was added to the stirred solution. The reaction mixture was stirred for 10 minutes, then diluted with t-butyl methyl ether (1.0 L). The lower aqueous phase was separated and transferred to a 12 L, 3-neck round bottom flask equipped with a mechanical stirrer. t-Butyl methyl ether was added (1.8 L) and the stirred mixture was cooled to <10° C. (ice bath). Concentrated HCl solution (300 mL of 12 M solution) was added and the mixture was vigorously stirred. The layers were separated and aqueous phase was further acidified with con. HCl (30 mL) and extracted again with t-butyl methyl ether (1.0 L). The combined MTBE extracts were washed with brine (1 L), dried (MgSO$_4$, 70 g), filtered and concentrated under reduced pressure to give 827 g of a yellow solid. The crude solid was slurried in hexanes (2.2 L) and transferred to a 5 L, 3-neck round bottom flask equipped with a mechanical stirrer. The mixture was stirred at <10° C. (ice bath) for 1 h, then filtered, washed with hexanes (4×100 mL) and dried to constant weight (−30 in. Hg, ambient temperature, 14 h). Recovery=309 g of a pale yellow powder (68.6%).

Step B: Preparation of (S)-3-(3-Chlorophenyl)-3-Hydroxypropanoic Acid:

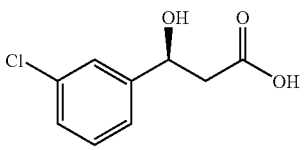

A 12 L, 3-neck round bottom flask was equipped with a mechanical stirrer and addition funnel (1 L). The flask was flushed with nitrogen and charged with 3-(3-chlorophenyl)-3-oxo-propanic acid (275.5 g) and dichloromethane (2.2 L). A thermocouple probe was immersed in the reaction slurry and the stirred contents were cooled to −20° C. Triethylamine (211 mL) was added over 5 minutes to the stirred slurry and all solids dissolved. A dichloromethane solution of (−)-β-chlorodiisopinocampheylborane (1.60 M, 1.04 L) was charged to the addition funnel, then added slowly with stirring, maintaining the temperature between −20 and −25° C. After the addition was complete (35 min), the solution was warmed to ice bath temperature (2–3° C.) and stirred for 4 h. An in-process NMR analysis indicated the starting material was <4%. Water (1.2 L) was added to the cloudy orange reaction mixture, followed by 3 M NaOH solution (1.44 L). The mixture was vigorously stirred for 5 min, then transferred to a separatory funnel. The layers were separated and the basic aqueous phase was washed with ethyl acetate (1.0 L). The aqueous phase was acidified with conc. HCl (300 mL) and extracted with ethyl acetate (2×1.3 L). The two acidic ethyl acetate extracts were combined, washed with brine (600 mL), dried (MgSO$_4$, 130 g), filtered and concentrated under reduced pressure to provide 328 g of a yellow oil (the oil crystallized on standing). The solid was slurried in ethyl acetate (180 mL) and transferred to a 2 L, 3-neck round bottom flask, equipped with a mechanical stirrer. The stirred mixture was cooled to <10° C. (ice bath), then diluted with hexanes (800 mL). The resulting mixture was stirred at ice bath temperature for 4 h, then filtered. The collected solid was washed with 4:1 hexanes:ethyl acetate (3×50 mL) and dried to constant weight (−30 in. Hg, ambient temperature, 12 h). Recovery=207.5 g of a white powder (74.5%).

Step C: Preparation of (S)-(−)-1-(3-Chlorophenyl)-1,3-Propanediol:

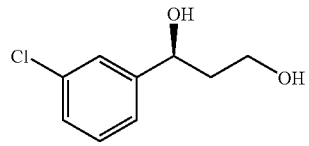

The compound was prepared as described in Example 7, Step D.

The residue was dissolved in methanol (1 mL) and analyzed by chiral HPLC (see, Example 7; Step B). ee>98%.

Example 10

The Preparation of 1,3-Diols via Catalytic Asymmetric Hydrogenation

Step A:
Beta-ketoester starting material was synthesized as described in Example 7, step A.

Step B:
A solution containing beta-ketoester (1 mmole) in either methanol or ethanol (5–10 ml/mmole ketoester) was degassed through several pump/vent (N$_2$) cycles at room temperature. The degassed solution was moved into a glove bag and under an atmosphere of N$_2$ was poured into a stainless steel bomb containing a stir bar and 1.0 mole % Ru-BINAP catalyst. The bomb was sealed, removed from the glove bag and purged with H$_2$ prior to stirring 18–24 h at room temperature and 150 psi H$_2$. After venting the hydrogen pressure, the bomb was opened and the reaction mixture was removed and concentrated. The crude beta-hydroxyester was used for hydrolysis.

Step C:
Crude beta-hydroxy ester was hydrolyzed as described in Example 7, step C.

Step D:
Optically active beta-hydroxy acid was reduced as described in Example 7, step D.

Synthesis of Racemic Phosphorylating Agents of Formula I

Example 11

General procedure for the synthesis of trans-4-(aryl)-2-(4-nitrophenoxy)-2-oxo-1,3,2-dioxaphosphorinanes of Formula I Formula I

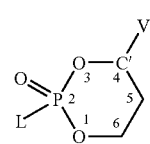

Example 11a

Synthesis of trans-4-(3-chlorophenyl)-2-(4-nitrophenoxy)-2-oxo-1,3,2-dioxaphosphorinane A solution of 1-(3-chlorophenyl)-1,3-propane diol (25 g, 134 mmol) and triethylamine (62.5 mL, 442 mmol) in THF was added to a solution of 4-nitrophenyl-phosphorodichloridate (37.7 g, 147 mmol) in THF at room temperature and the resulting solution was heated at reflux. After 2 hours, TLC indicated complete consumption of the starting diol and formation of the cis and trans isomers in a 60/40 ratio (HPLC). The clear yellow solution was cooled to 30° C., sodium 4-nitrophenoxide (56 g, 402 mmol)) was added and the reaction mixture was heated at reflux. After 90 minutes the reddish reaction mixture was cooled to room temperature and stirred at room temperature for 2 hours then placed in the refrigerator overnight. The final ratio was determined by HPLC to be 96/4 trans/cis. The reaction mixture was quenched with a saturated solution of ammonium chloride and diluted with ethyl acetate. The layers were separated and the organics were washed 4 times with 0.3 N sodium hydroxide to remove the nitrophenol, then saturated sodium chloride and dried over sodium sulfate. The filtered solution was concentrated under reduced pressure and the resulting solid was recrystallized from ethyl acetate to give large off white needles (45 g, 91%, mp=115–116° C., purity 98 A %).

$^1$H NMR (CDCl$_3$, Varian Gemini 200 MHz): C'-proton: cis-isomer 5.6–5.8 (m, 1H), trans-isomer 5.5–5.6 9 (m, 1H).

TLC conditions: Merck silica gel 60 F254 plates, 250 µm thickness; mobile phase=60/40 hexanes/ethyl acetate; rf: diol=0.1, cis-phosphate=0.2, trans-phosphate=0.35.

HPLC conditions: Column=Waters µ Bondapack C18 3.9×300 mm; mobile phase=40/60 acetonitrile/phosphate buffer pH 6.2; flow rate=1.4 mL/min; detection=UV @ 270 nm; retention times in min: cis-isomer=14.46, trans-isomer=16.66, 4-nitrophenol=4.14.

Example 11b

Synthesis of trans-4-(3-pyrid-3-yl)-2-(4-nitrophenoxy)-2-oxo-1,3,2-dioxaphosphorinanes Same as Example 11a
$^1$H NMR (CDCl$_3$, Varian Gemini 200 MHz): C'-proton: trans-isomer 5.6–5.8 (m, 1H)

Example 11c

Synthesis of trans-4-(3,-5-difluorophenyl)-2-(4-nitrophenoxy)-2-oxo-1,3,2-dioxaphosphorinanes Same as Example 11a
TLC conditions: Merck silica gel 60 F254 plates, 250 µm thickness; mobile phase=50/50 hexanes/ethyl acetate; rf: diol=0.1, cis-phosphate=0.25, trans-phosphate=0.4.
$^1$H NMR (CDCl$_3$, Varian Gemini 200 MHz): C'-proton: trans-isomer 5.7–5.5 (m, 1H)

Example 11d

Synthesis of trans-4-(4-methylphenyl)-2-(4-nitrophenoxy)-2-oxo-1,3,2-dioxaphosphorinane Same as Example 11a starting with 1-(4-methylphenyl)-1,3-propane diol
TLC: 50/50 hexanes/ethyl acetate; Rf: cis-phosphate=0.25; trans-phosphate=0.35.
$^1$H NMR (CDCl$_3$, Varian Gemini 200 MHz): C'-proton: trans-isomer 5.65–5.5 (m, 1H)

Example 11e

Synthesis of trans-4-(3,5-dimethylphenyl)-2-(4-nitrophenoxy)-2-oxo-1,3,2-dioxaphosphorinane Same as Example 11a starting with 1-(3,5-dimethylphenyl)-1,3-propane diol
TLC: 50/50 hexanes/ethyl acetate; Rf: cis-phosphate=0.2; trans-phosphate=0.3.
$^1$H NMR (CDCl$_3$, Varian Gemini 200 MHz): C'-proton: trans-isomer 5.6–5.45 (m, 1H)

Example 11f

Synthesis of trans-4-(3,5-dichlorophenyl)-2-(4-nitrophenoxy)-2-oxo-1,3,2-dioxaphosphorinane Same as Example 11a starting with 1-(3,5-dichlorophenyl)-1,3-propane diol
TLC: 70/30 hexanes/ethyl acetate; Rf: cis-phosphate=0.3; trans-phosphate=0.5.
$^1$H NMR (CDCl$_3$, Varian Gemini 200 MHz): C'-proton:. trans-isomer 5.85–5.7 (m, 1H)

Example 11g

Synthesis of trans-4-(pyrid-4-yl)-2-(4-nitrophenoxy)-2-oxo-1,3,2-dioxaphosphorinane Same as Example 11a starting with 1-(pyrid-4-yl)-1,3-propane diol
TLC: 95/5 dichloromethane/ethanol; Rf: trans-phosphate=0.35.
$^1$H NMR (CDCl$_3$, Varian Gemini 200 MHz): C'-proton: trans-isomer 5.7–5.55 (m, 1H)

Example 11h

Synthesis of trans-4-(3-methoxycarbonylphenyl)-2-(4-nitrophenoxy)-2-oxo-1,3,2-dioxaphosphorinane Same as Example 11a starting with 1-(3-methoxycarbonylphenyl)-1,3-propane diol
TLC: 30/70 hexanes/ethyl acetate; Rf: cis-phosphate=0.5; trans-phosphate=0.6.
$^1$H NMR (CDCl$_3$, Varian Gemini 200 MHz): C'-proton: trans-isomer 5.7–5.6 (m, 1H)

Example 11i

Synthesis of trans-4-(4-methoxycarbonylphenyl)-2-(4-nitrophenoxy)-2-oxo-1,3,2-dioxaphosphorinane Same as Example 11a starting with 1-(4-methoxycarbonylphenyl)-1,3-propane diol
TLC: 30/70 hexanes/ethyl acetate; Rf: cis-phosphate=0.35; trans-phosphate=0.5.
$^1$H NMR (CDCl$_3$, Varian Gemini 200 MHz): C'-proton: trans-isomer 5.7–5.6 (m, 1H)

Example 11j

Synthesis of trans-4-(5-bromopyrid-3-yl)-2-(4-nitrophenoxy)-2-oxo-1,3,2-dioxaphosphorinane Same as Example 11a starting with 1-(5-bromopyrid-3-yl)-1,3-propane diol
$^1$H NMR (CDCl$_3$, Varian Gemini 200 MHz): C'-proton: trans-isomer 5.8–5.65 (m, 1H)

Example 11k

Synthesis of trans-4-(2,3-dichlorophenyl)-2-(4-nitrophenoxy)-2-oxo-1,3,2-dioxaphosphorinane Same as Example 11a starting with 1-(2,3-dichlorophenyl)-1,3-propane diol except that the isomerization was conducted with 4-nitrophenol and lithium hydride as in Example 13a.
$^1$H NMR (CDCl$_3$, Varian Gemini 200 MHz): C'-proton: trans-isomer 6–5.9 (m, 1H)

Example 11l

Synthesis of trans-4-(2,3,5-trichlorophenyl)-2-(4-nitrophenoxy)-2-oxo-1,3,2-dioxaphosphorinane Same as Example 11a starting with 1-(2,3,5-trichlorophenyl)-1,3-propane diol except that the isomerization was conducted with 4-nitrophenol and triethylamine as in example 13b.
$^1$H NMR (CDCl$_3$, Varian Gemini 200 MHz): C'-proton: trans-isomer 5.9–5.7 (m, 1H)

Example 11m

Synthesis of trans-4-(2-chlorophenyl)-2-(4-nitrophenoxy)-2-oxo-1,3,2-dioxaphosphorinane Same as Example 11a starting with 1-(2-chlorophenyl)-1,3-propane diol except that the isomerization was conducted with 4-nitrophenol and lithium hydride as in example 13a.
$^1$H NMR (CDCl$_3$, Varian Gemini 200 MHz): C'-proton: trans-isomer 6–5.9 (m, 1H)

Example 11n

Synthesis of trans-4-(3,5-dimethoxyphenyl)-2-(4-nitrophenoxy)-2-oxo-1,3,2-dioxaphosphorinane Same as Example 11a starting with 1-(3,5-dimethoxyphenyl)-1,3-propane diol except that the isomerization was conducted with 4-nitrophenol and triethylamine as in example 13b.
$^1$H NMR (CDCl$_3$, Varian Gemini 200 MHz): C'-proton: trans-isomer 5.55–5.45 (m, 1H), 3.3 (s, 6H)

Example 11o

Synthesis of trans-4-(2-bromophenyl)-2-(4-nitrophenoxy)-2-oxo-1,3,2-dioxaphosphorinane Same as Example 11a starting with 1-(2-bromophenyl)-1,3-propane diol except that the isomerization was conducted with 4-nitrophenol and triethylamine as in Example 13a.
$^1$H NMR (CDCl$_3$, Varian Gemini 200 MHz): C'-proton: trans-isomer 5.95–5.85 (m, 1H)

Example 11p

Synthesis of trans-4-(3-bromo-5-ethoxyphenyl)-2-(4-nitrophenoxy)-2-oxo-1,3,2-dioxaphosphorinane Same as Example 11a starting with 1-(3-bromo-5-ethoxyphenyl)-1,3-propane diol except that the isomerization was conducted with 4-nitrophenol and triethylamine as in Example 13b.
$^1$H NMR (CDCl$_3$, Varian Gemini 200 MHz): C'-proton: trans-isomer 5.9–5.75 (m, 1H), 4.04 (q, 2H), 1.39 (t, 3H).

Example 11q

Synthesis of trans-4-(2-trifluoromethylphenyl)-2-(4-nitrophenoxy)-2-oxo-1,3,2-dioxaphosphorinane Same as Example 11a starting with 1-(2-trifluoromethylphenyl)-1,3-propane diol except that the isomerization was conducted with 4-nitrophenol and triethylamine as in Example 13b.
$^1$H NMR (CDCl$_3$, Varian Gemini 200 MHz): C'-proton: trans-isomer 6–5.75 (m, 1H).

Example 11r

Synthesis of trans-4-(4-chlorophenyl)-2-(4-nitrophenoxy)-2-oxo-1,3,2-dioxaphosphorinane Same as Example 11a starting with 1-(4-chlorophenyl)-1,3-propane diol except that the trans-isomer was isolated from the cis/trans mixture without isomerization.
TLC: hexanes/ethyl acetate 1/1; Rf: cis-phosphate=0.2; trans-phosphate=0.6.
$^1$H NMR (CDCl$_3$, Varian Gemini 200 MHz): C'-proton: trans-isomer 5.6–5.5 (m, 1H).

Example 11s

Synthesis of trans-4-(3-methylphenyl)-2-(4-nitrophenoxy)-2-oxo-1,3,2-dioxaphosphorinane Same as Example 11a starting with 1-(3-methylphenyl)-1,3-propane diol except that the trans-isomer was isolated from the cis/trans mixture without isomerization.
TLC: hexanes/ethyl acetate 6/4; Rf: cis-phosphate=0.2; trans-phosphate=0.5.
$^1$H NMR (CDCl$_3$, Varian Gemini 200 MHz): C'-proton: trans-isomer 5.65–5.5 (m, 1H).

Example 11t

Synthesis of trans-4-(4-fluorophenyl)-2-(4-nitrophenoxy)-2-oxo-1,3,2-dioxaphosphorinanes Same as Example 11a starting with 1-(4-fluorophenyl)-1,3-propane diol except that the trans-isomer was isolated from the cis/trans mixture without isomerization.
$^1$H NMR (DMSO-d$_6$, Varian Gemini 200 MHz): C'-proton: trans-isomer 5.78–5.85 (m, 1H).

Example 11u

Synthesis of trans-4-(2-fluorophenyl)-2-(4-nitrophenoxy)-2-oxo-1,3,2-dioxaphosphorinane Same as Example 11a starting with 1-(2-fluorophenyl)-1,3-propane diol except that the trans-isomer was isolated from the cis/trans mixture without isomerization.
$^1$H NMR (DMSO-$d_6$, Varian Gemini 200 MHz): C'-proton: trans-isomer 5.9–6.1 (m, 1H).

Example 11u

Synthesis of trans-4-(3-fluorophenyl)-2-(4-nitrophenoxy)-2-oxo-1,3,2-dioxaphosphorinane Same as Example 11a starting with 1-(3-fluorophenyl)-1,3-propane diol except that the trans-isomer was isolated from the cis/trans mixture without isomerization.
$^1$H NMR (DMSO-$d_6$, Varian Gemini 200 MHz): C'-proton. trans-isomer 5.8–5.9 (m, 1H).

Example 11v

Synthesis of trans-4-[4-(4-chlorophenoxy)phenyl]-2-(4-nitrophenoxy)-2-oxo-1,3,2-dioxaphosphorinane Same as Example 11a starting with 1-[4-(4-chlorophenoxy)phenyl]-1,3-propane diol except that the trans-isomer was isolated from the cis/trans mixture without isomerization.
$^1$H NMR (DMSO-$d_6$, Varian Gemini 200 MHz): C'-proton: trans-isomer 5.75–5.9 (m, 1H).

Example 11w

Synthesis of trans-4-(3-bromophenyl)-2-(4-nitrophenoxy)-2-oxo-1,3,2-dioxaphosphorinane Same as Example 11a starting with 1-(3-bromophenyl)-1,3-propane diol except that the trans-isomer was isolated from the cis/trans mixture without isomerization.
TLC: hexanes/ethyl acetate 1/1; Rf: cis-phosphate=0.25; trans-phosphate=0.5.
$^1$H NMR (DMSO-$d_6$, Varian Gemini 200 MHz): C'-proton: trans-isomer 5.8–5.95 (m, 1H).

Example 11x

Synthesis of trans-4-(3,4-ethylenedioxyphenyl)-2-(4-nitrophenoxy)-2-oxo-1,3,2-dioxaphosphorinane Same as Example 11a starting with 1-(3,4-ethylenedioxyphenyl)-1,3-propane diol except that the trans-isomer was isolated from the cis/trans mixture without isomerization.
TLC: hexanes/ethyl acetate 1/1; Rf: trans-phosphate=0.6.
$^1$H NMR (DMSO-$d_6$, Varian Gemini 200 MHz): C'-proton: trans-isomer 5.8–5.9 (m, 1H).

Example 11y

Synthesis of trans-4-(2-fluoro-4-chlorophenyl)-2-(4-nitrophenoxy)-2-oxo-1,3,2-dioxaphosphorinane Same as Example 11a starting with 1-(2-fluoro-4-chlorophenyl)-1,3-propane diol except that the trans-isomer was isolated from the cis/trans mixture without isomerization.
TLC: hexanes/ethyl acetate 1/1; Rf: trans-phosphate=0.7.
$^1$H NMR (DMSO-$d_6$, Varian Gemini 200 MHz): C'-proton: trans-isomer 5.9–6 (m, 1H).

Example 11z

Synthesis of trans-4-(2,6-dichlorophenyl)-2-(4-nitrophenoxy)-2-oxo-1,3,2-dioxaphosphorinane Same as Example 11a starting with 1-(2,6-dichlorophenyl)-1,3-propane diol except that the trans-isomer was isolated from the cis/trans mixture without isomerization.
TLC: hexanes/ethyl acetate 1/1; Rf: trans-phosphate=0.65.
$^1$H NMR (DMSO-$d_6$, Varian Gemini 200 MHz): C'-proton: trans-isomer 6.2–6.4 (m, 1H).

Example 11aa

Synthesis of trans-4-(2-fluoro-5-methoxyphenyl)-2-(4-nitrophenoxy)-2-oxo-1,3,2-dioxaphosphorinane Same as Example 11a starting with 1-(2-fluoro-5-methoxyphenyl)-1,3-propane diol except that the trans-isomer was isolated from the cis/trans mixture without isomerization.
$^1$H NMR (CDCl$_3$, Varian Gemini 200 MHz): C'-proton: trans-isomer 5.8–5.95 (m, 1H), 3.8 (s, 3H).

Example 11bb

Synthesis of trans-4-(3-fluoro-4-chlorophenyl)-2-(4-nitrophenoxy)-2-oxo-1,3,2-dioxaphosphorinane Same as Example 11a starting with 1-(3-fluoro-4-chlorophenyl)-1,3-propane diol except that the isomerization was conducted with 4-nitrophenol and triethylamine as in Example 13b.
$^1$H NMR (CDCl$_3$, Varian Gemini 200 MHz): C'-proton: trans-isomer 5.4–5.6 (m, 1H).

Example 11cc

Synthesis of trans-4-(3-chloro-4-fluorophenyl)-2-(4-nitrophenoxy)-2-oxo-1,3,2-dioxaphosphorinane Same as Example 11a starting with 1-(3-chloro-4-fluorophenyl)-1,3-propane diol except that the isomerization was conducted with 4-nitrophenol and triethylamine as in Example 13b.
$^1$H NMR (CDCl$_3$, Varian Gemini 200 MHz): C'-proton: trans-isomer 5.5–5.6 (m, 1H).

Example 11dd

Synthesis of trans-4-(2-fluoro-5-bromophenyl)-2-(4-nitrophenoxy)-2-oxo-1,3,2-dioxaphosphorinane Same as Example 11a starting with 1-(2-fluoro-5-bromophenyl)-1,3-propane diol except that the isomerization was conducted with 4-nitrophenol and triethylamine as in Example 13b.
$^1$H NMR (CDCl$_3$, Varian Gemini 200 MHz): C'-proton: trans-isomer 5.8–5.9 (m, 1H).

Example 11ee

Synthesis of trans-4-(2,3,5,6-tetrafluorophenyl)-2-(4-nitrophenoxy)-2-oxo-1,3,2-dioxaphosphorinane Same as Example 11a starting with 1-(2,3,5,6-tetrafluorophenyl)-1,3-propane diol except that the isomerization was conducted with 4-nitrophenol and triethylamine as in Example 13b.

$^1$H NMR (CDCl$_3$, Varian Gemini 200 MHz): C'-proton: trans-isomer 5.9–6 (m, 1H).

Example 11ff

Synthesis of trans-4-(2,3,6-trifluorophenyl)-2-(4-nitrophenoxy)-2-oxo-1,3,2-dioxaphosphorinane Same as Example 11a starting with 1-(2,3,6-trifluorophenyl)-1,3-propane diol except that the isomerization was conducted with 4-nitrophenol and triethylamine as in Example 13b.

$^1$H NMR (CDCl$_3$, Varian Gemini 200 MHz): C'-proton: trans-isomer 5.9–6 (m, 1H).

Example 12

General procedure for the synthesis of trans-4-(aryl)-2-(4-nitrophenoxy)-2-oxo-1,3,2-dioxaphosphorinanes using phosphorus oxychloride Phosphorus oxychloride (3.4 mL, 36.3 mmol) was added to a solution of 1-(3-chlorophenyl)-1,3-propane diol in dichloromethane at 0° C. followed by triethylamine (10.2 mL, 73 mmol). After 2 hours, sodium 4-nitrophenoxide (10.63 g, 66 mmol) was added to the solution of cis/trans phosphorochloridate reagent and the orange reaction mixture was heated at reflux for 1 hour. The cooled solution was partitioned with ethyl acetate and a saturated solution of ammonium chloride. The organics were separated and dried over sodium sulfate, filtered and concentrated under reduced pressure. The residue was taken up in THF, sodium 4-nitrophenoxide (10.63 g, 66 mmol) was added and the orange reaction mixture was heated to reflux for 3 hours (HPLC, 95/5 trans/cis). The cooled solution was partitioned with ethyl acetate and a saturated solution of ammonium chloride. The organics were separated and washed with 0.3 N solution of sodium hydroxide and brine, dried over sodium sulfate and concentrated under reduced pressure. Recrystallization from ethyl acetate as in Example 10 gave the phosphate reagent.

Example 13

Procedures for the enrichment in trans-isomer of a cis/trans mixture of 4-(aryl)-2-(4-nitrophenoxy)-2-oxo-1,3,2-dioxaphosphorinane A cis/trans mixture of 4-(3-chlorophenyl)-2-(4-nitrophenoxy)-2-oxo-1,3,2-dioxaphosphorinanes was prepared as in Example 11, except that the cis and trans isomers were separated by column chromatography prior to the addition of 4-nitrophenol.

Cis-4-(3-chlorophenyl)-2-(4-nitrophenoxy)-2-oxo-1,3,2-dioxaphosphorinane was isomerized to the trans isomer by adding a solution of the cis-isomer to a solution of 4-nitrophenoxide prepared with the following bases.

Example 13a

Lithium hydride (19.4 mg, 2.44 mmol) was added to a solution of 4-nitrophenol in THF at room temperature. The yellow solution was stirred at room temperature for 30 minutes. A solution of cis-4-(3-chlorophenyl)-2-(4-nitrophenoxy)-2-oxo-1,3,2-dioxaphosphorinane (300 mg, 0.813 mmol) in THF was added to the solution of lithium 4-nitrophenoxide. The orange reaction mixture was stirred a room temperature. After 5 hours the ratio was 92.9/5.4 trans/cis (HPLC determination).

Example 13b

Same as above using triethylamine instead of lithium hydride. After 20 hours the trans/cis ratio was 90.8/5.3.

Example 13c

Same as above using DBU instead of lithium hydride. After 3 hours the trans/cis ratio was 90.8/5.3.

Example 14

General procedure for the synthesis of trans-4-(aryl)-2-chloro-2-oxo-1,3,2-dioxaphosphorinane

Example 14a

Synthesis of trans-4-(3-chlorophenyl)-2-chloro-2-oxo-1,3,2-dioxaphosphorinane

Phosphorus oxychloride (16.76 g, 109.3 mmol) was added slowly to a solution of 1-(3-chlorophenyl)-1,3-dihydroxypropane (17 g, 91.1 mmol) in dichloromethane (250 mL) under nitrogen at 0° C. After stirring at 0° C. for 10 minutes, a solution of triethylamine in dichloromethane (50 mL) was added over 5 minutes. Upon completion of the addition, the reaction mixture was heated at reflux for 2 hours. The brownish reaction mixture was cooled to room temperature and concentrated under reduced pressure. The residue was diluted with ethyl acetate and washed with saturated sodium bicarbonate (4×100 mL), water, saturated sodium chloride and dried over magnesium sulfate. The filtered solution was concentrated under reduced pressure to give a tan solid. Recrystallization with ether gave a first crop of 13.62 g (56%) of desired product as a white powder. The mother liquor was subjected to a second recrystallization, which yielded a second crop of 1.53 g, bringing the total yield to 15.15 g (62%, mp=71–73° C.).

$^1$H NMR (CDCl$_3$, Varian Gemini 200 MHz): C'-proton: cis-isomer 5.6–5.8 (m, 1H); trans-isomer 5.55–5.6 9 (m, 1H).

TLC conditions: mobile phase=1:1, ethyl acetate:hexanes. Rf: product=0.53; diol=0.36. Visualized with phosphomolybdic acid/ethanol stain.

Example 14b

Synthesis of trans-4-(S)-(−)-(4-pyridyl)-2-chloro-2-oxo-1,3,2-dioxaphosphorinane

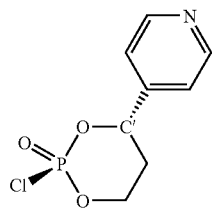

An oven-dried 250 mL round bottom flask equipped with a magnetic stir-bar was charged with 3.49 g of the S-(−)1-(4-Pyridyl)-1,3-propanediol followed by 60 mL of acetonitrile. The heterogeneous mixture was allowed to stir at room temperature for 15 minutes and then slowly treated with 5.7 mL of 4 M HCl in dioxane solution over 5 minutes. After stirring for 1 hour at room temp the reaction mixture was treated with 2.16 mL of $POCl_3$ in one portion via a syringe. In a separate 25 mL flask 2.68 g of DABCO was dissolved in 15 mL of acetonitrile under nitrogen and transferred via a syringe or an addition funnel to the reaction mixture over 5 minutes. A slight exotherm was observed at the end of the addition of the DABCO solution (+10° C.). The reaction mixture was allowed to stir for 1 hour at ambient temperature during which it remained heterogeneous. A small sample of the reaction mixture was pulled out and quickly evaporated with a jet of dry $N_2$ and the residue was dissolved in DMSO-$d_6$ to run a $^1$H-NMR spectrum.

$^1$H NMR (DMSO-$d_6$, Varian Gemini 200 MHz): C'-proton: trans-isomer 5.85–5.75 (d, 1H).

Synthesis of Enantioenriched Phosphorylating Agenst of Formula I

Example 15

General procedure for the synthesis of chiral trans-4-(aryl)-2-(4-nitrophenoxy)-2-oxo-1,3,2-dioxaphosphorinanes

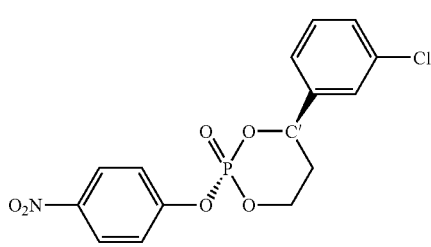

Example 15a

Synthesis of (+)-(4R)-trans-4-(3-chlorophenyl)-2-(4-nitrophenoxy)-2-oxo-1,3,2-dioxaphosphorinane A solution of (+)-(R)-1-(3-chlorophenyl)-1,3-propane diol (3 g, 16.1 mmol) and triethylamine (6.03 ml, 59.6 mmol) in THF (80 mL) was added dropwise to a solution of 4-nitrophenoxyphosphorodichloridate (7.63 g, 29.8 mmol) in 150 mL of THF at 0° C. After about 2 h, the starting diol was consumed, with the formation of two isomeric 4-nitophenylphosphates, and additional triethylamine (8.31 mL) followed by of 4-nitrophenol (8.29 g, 59.6 mmol) were added. The reaction mixture was stirred overnight. The solvent was evaporated under reduced pressure and the residue was partitioned between ethyl acetate and water. The organic phase was washed (0.4 M NaOH, water and sat'd NaCl solution) and dried over $MgSO_4$. Concentration and chromatography of the residue using 30% ethyl acetate in hexanes yielded 4.213 g (71%) of the desired product.

HNMR (200 MHz, $CDCl_3$): 8.26 (2H, d, J=9.7 Hz), 7.2–7.5 (6H, m), 5.56 (1H, apparent d, J=11.7 Hz), 4.4–4.7 (2H, m), 2.2–2.6 (1H, m), 2.0–2.2 (1H, m).

m.p.: 114–115° C. $[\alpha]_D$=+91.71. Elemental Analysis: Calculated for $C_{15}H_{13}NO_6ClP$: C: 48.73, H: 3.54, N: 3.79. Found: C: 48.44, H: 3.20, N: 3.65.

Example 15b

Synthesis of (−)-(4S)-trans-4-(3-chlorophenyl)-2-(4-nitrophenoxy)-2-oxo-1,3,2-dioxaphosphorinane

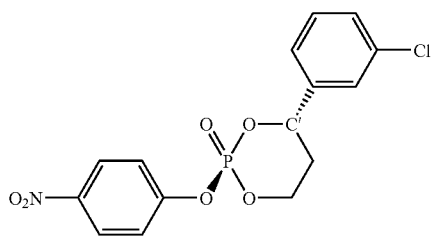

In a similar manner, from 3.116 g of (−)-(S)-1-(3-chlorophenyl)-1,3-propane diol was obtained 4.492 g (72%) of the desired phosphate.

HNMR (200 MHz, $CDCl_3$): 8.26 (2H, d, J=9.7 Hz), 7.2–7.5 (6H, m), 5.56 (1H, apparent d, J=11.7 Hz), 4.4–4.7 (2H, m), 2.2–2.6 (1H, m), 2.0–2.2 (1H, m).

m.p.: 114–115° C. $[\alpha]_D$=−91.71. Elemental Analysis: Calculated for $C_{15}H_{13}NO_6ClP$: C: 48.73, H: 3.54, N: 3.79. Found: C: 48.61, H: 3.36, N: 3.66.

Example 15c

Synthesis of (−)-(4S)-trans-phenyl-2-(4-nitrophenoxy)-2-oxo-1,3,2-dioxaphosphorinane Same as Example 11a starting with S-(−)-1-phenyl-1,3-propane diol except that the isomerization was conducted with 4-nitrophenol and triethylamine as in Example 13b.

TLC: hexanes/ethyl acetate 4/1); Rf=0.4

$^1$H NMR (DMSO-$d_6$, Varian Gemini 300 MHz): C'-proton: trans-isomer 5.85–5.75 (m, 1H).

Example 16

General Procedures for Maintaining Enantiomeric Excess During Synthesis of Enantioenriched Phosphorylating Reagent

Example 16a

Synthesis of (−)-(4S)-trans-(Pyrid-4-yl)-2-(4-nitrophenoxy)-2-oxo-1,3,2-dioxaphosphorinane

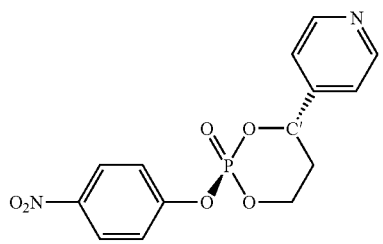

A 12 L round bottom flask equipped with an overhead stirrer and nitrogen inlet was charged with (S)-(−)-1-(pyrid-4-yl)-1,3-propanediol (1.2 kg, 7.83 mol) and pyridine (6 L) The mixture was vigorously stirred at room temperature for 0.5 h until all the solids had dissolved. Meanwhile, a 22 L, 3-neck flask was equipped with an overhead stirrer, thermocouple, cooling bath, and nitrogen inlet. This vessel was charged with 4-nitrophenyl phosphorodichloridate (2.01 kg, 7.83 mol) and pyridine (6 L). The resulting mixture was cooled to 3.3° C. After the diol was completely dissolved (0.5 h), triethylamine (190 mL, 1.36 mol) was added and the slightly cloudy, yellow-brown solution was transferred in portions to a 2 L addition funnel on the 22 L flask. The solution was added to the cold phosphorodichloridate solution over 3.25 h. After the addition was complete, the cooling bath was drained and stirring was continued for 3 h. During this time, a 50 L, 3-neck flask was equipped with an overhead stirrer, thermocouple, addition funnel, cooling bath (ice water) and nitrogen inlet. This flask was then charged with sodium hydride (180 g, 4.5 mol) and THF (1 L) and the addition funnel was charged with a solution of 4-nitrophenol (817 g, 5.87 mol) in THF (1 L). The nitrophenol solution was slowly added to the cold suspension of sodium hydride. After the addition was complete, the resulting bright orange suspension was stirred at room temperature for 1 h. After the diol-dichloridate reaction was judged complete the dark suspension was subjected to vacuum filtration. The glassware and filter cake (triethylamine-HCl) were rinsed with THF (1 L) and the combined filtrate and rinse were poured into the orange, sodium 4-nitrophenoxide suspension. The resulting mixture was then heated at 40° C. for 3.5 h at which time the heating mantle was turned off and the reaction was stirred an additional 11 h at room temperature. The crude reaction mixture was concentrated on a rotary evaporator at 45–50° C. at reduced pressure (oil pump). The resulting thick, black, foamy tar was dissolved in 1.5 M aq HCl (12 L) and ethyl acetate (8 L). The mixture was transferred to a 12.5-gallon separatory funnel, stirred 10 min, and the phases separated. The ethyl acetate layer was washed with an additional 1.3 L of 1.5 M aq HCl. To the combined aqueous layers was added dichloromethane (8 L) and the vigorously stirred mixture was carefully neutralized with solid sodium bicarbonate. The layers were separated and the aqueous layer was extracted with dichloromethane (8 L). The combined organic layers were dried over magnesium sulfate (600 g) and filtered. The solution was concentrated on a rotary evaporator until most of the solvent was removed and a thick suspension resulted. 2-Propanol (5 L) was added and evaporation continued until 4 L of distillate were collected. 2-Propanol (3 L) was added and evaporation continued until 3 L of distillate were collected. The thick slurry was diluted with 2-propanol (2 L) and the mixture stirred with cooling (ice bath) for 1 h. The solid was collected by filtration, washed with 2-propanol (2 L), and dried in a vacuum oven (−30 in. Hg, 55° C., 18 h) to a constant weight of 1.86 kg (70% yield).

mp 140–142° C.

Specific Rotation=−80.350 (c=1.0, MeOH); ee=99+% trans

HPLC conditions:

Column: Chiralpak AD, 0.46×25 cm; mobile phase=50:50, 2-propanol:hexane, isocratic; flow rate=1.0 mL/min; injection volume=10 μL UV detection at 254 nm.

The cis/trans equilibration was monitored by HPLC. Stopped at 92% trans, 6.6% cis, r.t.=trans isomer 6.9 min. and cis isomer 10.9 min $^1$HNMR (DMSO-$d_6$): δ=2.23–2.29 (m, 2H), 4.56–4.71 (m, 2H), 5.88–5.95 (m, 1H), 7.44 (d, 2 Hh, J=5.8 Hz), 7.59 (d, 2H, J=9.2 Hz), 8.34 (d, 2H, J=9.4 Hz), 8.63 (d, 2H J=5.8 Hz)

Example 16b

Synthesis of (−)-(4S)-(−)-(Pyrid-4-yl)-2-(4-nitrophenoxy)-2-oxo-1,3,2-dioxaphosphorinane A 1 liter 3-neck round bottom flask was equipped with a mechanical stirrer, addition funnel, a thermometer and a $N_2$ inlet. The flask is charged with S-(−)-1-(pyrid-4-yl)-propane-1,3-diol (25 g, 163.4 mmol) and ethyl acetate (250 mL) and the resulting suspension was treated slowly with a 4N HCl solution in dioxane (43 mL, 176 mmol) over a period of 15 min. After stirring for 30 min at room temperature, 4-nitrophenylphosphorodichloridate (41.81 g, 163.4 mmol) was added as a solid as quickly as possible under a positive flow of $N_2$. The internal temperature of the reaction mixture was adjusted to −10° C. with the help of a dry ice-acetone cooling bath. A solution of triethylamine (79 mL, 572 mmol) in ethyl acetate (100 mL) was added maintaining the reaction temperature at <−5° C. Thirty minutes after the complete addition of the triethylamine solution, the cooling bath was removed and the reaction mixture was stirred at room temperature for 1 h. The reaction mixture was filtered to remove triethylamine-hydrochloride salt, which is washed with ethyl acetate (3×30 mL) until the filtrate shows only faint absorption. The filtrate was evaporated down to a volume of 150–175 mL under reduced pressure. 4-nitrophenol (7.5 g, 54.3 mmol) and triethylamine (9 mL) were added to the concentrated solution and the resulting orange reaction mixture was stirred at room temperature for 24 h. The solid formed in the reaction mixture was collected by filtration, washed with ethyl acetate (2×25 mL) and methyl t-butyl ether (25 mL) and dried under vacuum at 55° C. to give 31.96 g (58.4%) of the desired product. Same analytical data as Example 15a.

Synthesis of Nucleoside Prodrugs of Formula II

Example 18

General Procedure for the Protection of Nucleosides

Example 18a

Synthesis of 2'-deoxy-2'-difluoro-3'-O-TBS-4-N-(N, N-dimethylformamidine)-cytidine Step A: Persilylation: synthesis of 3',5'-di-O-TBS-2'-deoxy-2'-difluoro-cytidine t-Butyldimethylsilyl chloride (21.4 g, 142 mmol) was added to a solution of 2'-deoxy-2'-difluoro-cytidine (6.08 g, 20.3 mmol) and imidazole (13.8 g, 203 mmol) in DMF (300 mL) at room temperature. After stirring at room temperature overnight the volatiles were removed under reduced pressure. The residue was partitioned between ethyl acetate and a saturated solution of ammonium chloride. The layers were separated and the organics were washed with brine, dried over sodium sulfate and concentrated under reduced pressure. The residue was purified by column chromatography (silica gel, dichloromethane/methanol) to give 8.3 g (70%) of the title compound.

TLC: dichloromethane/methanol 9/1; Rf=0.35
$^1$H NMR (Gemini 300 MHz, CD$_3$OD): 0.93 (s, 9H), 0.89 (s, 9H)

Step B: Selective 5'-desilylation: synthesis of 3'-O-TBS-2'-deoxy-2'-difluoro-cytidine To a solution of 3',5'-di-O-TBS-2'-deoxy-2'-difluoro-cytidine (8.3 g) in THF (15 mL) was added a 1:1 solution of trifluoroacetic acid in water (15 mL) and the resulting solution was placed in the refrigerator at −10° C. After 18 hours, the cold solution was neutralized with solid sodium bicarbonate (pH 8) and the aqueous layer was extracted with ethyl acetate (3×100 mL). The combined organic extracts were dried and concentrated under reduced pressure. The residue was purified by column chromatography (silica gel, dichloromethane/methanol) to give 5.3 g (83%) of the title compound.

TLC: dichloromethane/methanol 9/1; Rf=0.3
$^1$H NMR (Gemini 200 MHz, CD$_3$OD): 0.9 (s, 9H), 0.12 (s, 3H), 0.11 (s, 3H).

Step C: Nitrogen protection: synthesis of 2'-deoxy-2'-difluoro-3'-O-TBS-4-N-(N,N-dimethylformamidine)-cytidine DMF-dimethyl acetal was added to a solution of 3'-O-TBS-2'-deoxy-2'-difluoro-cytidine in pyridine at room temperature. After stirring at room temperature overnight, the volatiles were removed under reduced pressure and the residue was purified by column chromatography (silica gel, acetone/hexanes then acetone/methanol) to give 6 g (99%) of the title compound.

TLC: acetone; Rf=0.35
$^1$H NMR (Gemini 200 MHz, CD$_3$OD): 3.21 (s, 3H), 3.12 (s, 3H), 0.9 (s, 9H), 0.13 (s, 3H), 0.11 (s, 3H).

Example 18b

Synthesis of 2',3'-di-O-TBS-uracil-β-D-arabinofuranoside

Step A:
Same as Example 18a, Step A
TLC: hexanes/ethyl acetate 5/5); Rf=0.75
$^1$H NMR (Gemini 200 MHz, CD$_3$OD): 0.9 (s, 9H), 0.87 (s, 9H), 0.82 (s, 9H), 0.13 (s, 3H), 0.12 (s, 3H), 0.08 (s, 3H), 0.07 (s, 6H).

Step B:
Same as Example 18a,
TLC: hexanes/ethyl acetate 2/8); Rf=0.5
$^1$HNMR (Gemini 200 MHz, CD$_3$OD): 0.89 (s, 9H), 0.81 (s, 9H), 0.12 (s, 3H), 011 (s, 3H), 0.06 (s, 3H), −0.09 (s, 3H).

Example 18c

Synthesis of 2',3'-di-O-TBS-adenine-β-D-arabinofuranoside

Step A:
Same as Example 18a, Step A
TLC: dichloromethane/ethyl acetate 2/8); Rf=0.5
$^1$H NMR (Gemini 300 MHz, DMSO-d$_6$): 1.34 (s, 9H), 1.31 (s, 9H), 1.06 (s, 9H), 0.58 (s, 6H), 0.48 (s, 3H), 0.46 (s, 3H), 0.35 (s, 3H), 0.00 (s, 3H).

Step B:
Same as Example 18a,
TLC: dichloromethane/methanol 9/1); Rf=0.5
$^1$H NMR (Gemini 300 MHz, DMSO-d$_6$): 1.33 (s, 9H), 1.02 (s, 9H), 0.57 (s, 3H), 0.56 (s, 3H), 0.34 (s, 3H), 0.00 (s, 3H).

Example 18d

Synthesis of 2',3'-di-O-TBS-4-N-(N,N-dimethylformamidine)-cytidine-β-D-arabinofuranoside Step A: Synthesis of 5'-O-benzoylcytarabine

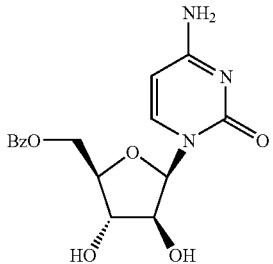

A 22 L, 4-neck flask was equipped with an overhead stirrer, thermocouple, nitrogen inlet, and empty cooling bath. The flask was charged with cytarabine (2.0 kg, 8.22 mol) and DMPU (4 L), giving a thick but stirrable solution. A 4 N solution of HCl in dioxane (2.5 L, 9.87 mol) was added in one portion. The mixture was stirred for 1.75 hours. Benzoyl chloride (2.3 kg, 16.45 mol) was added and the mixture was stirred at ambient temperature for 12 h. The thick suspension was poured onto a mixture of water (7 L) and ice (3 kg) in a 12.5 gallon extractor and the mixture was stirred for 30 minutes. The aqueous layer was extracted with dichloromethane (2×4 L). The combined organic layers were extracted with 10% (vol/vol) aqueous HCl (2×2 L). The combined aqueous layers were charged to a 50 L flask, equipped with an ice/water bath and overhead stirrer. The solution was diluted with water (5 L) and the pH was adjusted to 10 by adding 30% (wt/wt) aqueous NaOH (4 kg). The resulting thick suspension was stirred cold for 1.25 h. The solid was collected by filtration in two 24 cm Buchner funnels. The cake in each funnel was washed with water (2 L). The solid was dried in a vacuum oven at 70° C. for 48 h, giving 2.38 kg (84% yield) of 5'-O-benzoylcytarabine.

HPLC conditions:
Column: Zorbax Eclipse XDB-C8; Solvent A=5% acetonitrile in 20 mM sodium phosphate buffer; solvent B=80% acetonitrile in water; gradient; flow rate=1.0 mL/min; injection volume=10 μL UV detection at 270 nm.
r.t.=4.3 min.
Water content by KF=4.95%

Step B: Synthesis of 5'-O-benzoyl-2',3'-di-O-TBS-cytarabine

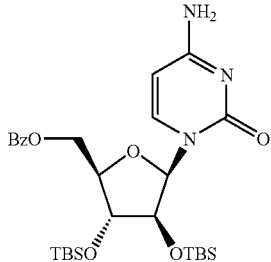

A 22 L, 4-neck flask was equipped with an overhead stirrer, thermocouple, condenser, and nitrogen inlet. The flask was charged with pyridine (1.5 L, 19.0 mol), DMF (3.3 L), and 5'-O-benzoylcytarabine in that order. The mixture was stirred for 5 minutes. tert-Butyldimethylsilyl chloride (2.4 kg, 15.8 mol) was added. The mixture was heated at 95° C.±1° C. for 36 h with occasional monitoring by HPLC. The mixture was cooled to 25° C. and methanol (550 mL) was added. The mixture was stirred for 30 minutes then water (4.4 L) was added. After stirring for 20 minutes, the mixture was extracted with ethyl acetate (4.4 L). The upper organic layer was washed with 10% (vol/vol) aqueous HCl (2×4.4 L), 7% (wt/vol) aqueous NaHCO$_3$ (2×4.4 L), and 10% (wt/vol) aqueous NaCl (4 L). The organic layer was dried over MgSO$_4$ (300 g) and filtered. The solvent was removed on a rotary evaporator, giving a thick, black oil weighing 2.73 kg. The residue was dissolved in DMF (6.5 L) and the solvent evaporated under reduced pressure (rotary evaporator, bath temp=60° C., vacuum pump). DMF (6 L) addition and evaporation was repeated twice more, giving 1.99 kg (109% of theoretical) of 5'-O-benzoyl-2',3'-di-O-TBS-cytarabine as a dark tar which is used in the subsequent reaction without further purification.

HPLC conditions:
Column: Zorbax Eclipse XDB-C8; Solvent A=5% acetonitrile in 20 mM sodium phosphate buffer; solvent B=80% acetonitrile in water; gradient; flow rate=1.0 mL/min; injection volume=10 μL UV detection at 270 nm.
r.t. di-silyl=10.1 min
r.t. monosilyl=6.9 min Step C: Synthesis of 2',3'-di-O-TBS-cytarabine hydrochloride

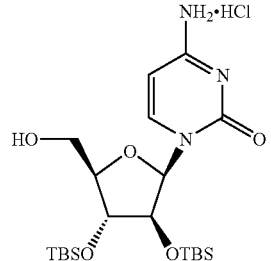

A 22 L, 3-neck flask was equipped with an overhead stirrer, condenser with nitrogen bubbler on top, a thermocouple, and a heating mantle. The flask was charged with a solution of the crude 5'-O-benzoyl-2',3'-di-O-TBS cytarabine in ethanol (5 L) and hydrazine (400 g, 12.5 mol). The mixture was heated at 80° C. for 15 h. The heating mantle was removed and the mixture cooled to 30° C. over 2 h. The dark colored solution was poured into 15% (wt/vol) aqueous NH$_4$Cl (9 L) and extracted with ethyl acetate (8 L). The organic phase was washed with 15% (wt/vol) aqueous NH$_4$Cl (4 L) then evaporated to a thick oil on a rotary evaporator. The residue was dissolved in acetonitrile (6.5 L) and transferred to a 22 L flask equipped with an overhead stirrer and addition funnel. Water (6 L) was added. Concentrated HCl (330 mL) was added dropwise over 15 minutes until the pH of the mixture was 2.0 (pH meter). The resulting cloudy solution was extracted with hexanes (4 L). The lower aqueous/acetonitrile layer was concentrated on a rotary evaporator until 6 L of distillate were collected. Water (3 L) was added and the resulting suspension was stirred on the rotary evaporator for 15 minutes. The solid was collected by filtration in two 24 cm Buchner funnel and the cake in each funnel was washed with water (1.5 L). The solid was dried in a vacuum oven at 65° C. for 24 h, giving 1.25 kg (77% yield) of 2',3'-di-O-TBS-cytarabine hydrochloride as a yellow-orange solid.

HCl Salt
HPLC conditions:
Column: Zorbax Eclipse XDB-C8; Solvent A=5% acetonitrile in 20 mM sodium phosphate buffer; solvent B=80% acetonitrile in water; gradient; flow rate=1.0 mL/min; injection volume=10 μL UV detection at 270 nm.
r.t.=7.4 min Step D: Synthesis of 2',3'-di-O-TBS-4-N-(N,N-dimethylformamidine)-cytidine-β-D-arabinofuranoside:

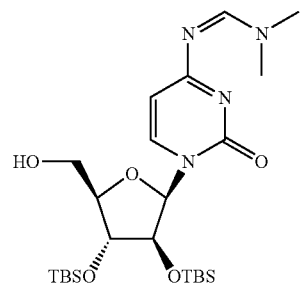

A 12.5 gallon extractor equipped with an overhead stirrer was charged with a solution of NaHCO$_3$ (412 g) in water (7.5 L), ethyl acetate (6.5 L), and 2',3'-di-O-TBS cytarabine hydrochloride (1.25 kg, 2.46 mol). The mixture stirred vigorously for 15 minutes then the layers were separated. The organic layer was washed with 10% (wt/vol) aqueous NaCl solution (5.5 L), dried over MgSO$_4$ (450 g), and filtered. The solvent was removed on a rotary evaporator, giving the free base as an orange foam weighing 1.35 kg (116% of theoretical). Toluene (2 L) was added and evaporation continued until 1.5 L of distillate were collected. Toluene (6 L) was added and the solution was transferred to a 22 L flask equipped with an overhead stirrer and nitrogen inlet. DMF dimethyl acetal (405 g, 3.19 mol) was added and the mixture was stirred at 20° C. for 18 h. The solvent was removed on a rotary evaporator, giving the title compound as a thick oil weighing 1.46 kg (113%). The material was used in the subsequent reaction without further purification.

TLC Conditions:
The reaction mixture was monitored using Merck silica gel 60 plates, 2.5×7.5 cm, 250 micron; UV lamp: 10% MeOH in CH$_2$Cl$_2$.
Rf of starting material=0.4
Rf of product=0.7.

¹HNMR (DMSO-d₆): δ −0.27 (s, 3H), −0.02 (s, 3H). 0.11 (s, 6H), 0.74 (s, 9H), 0.88 (s, 9H), 3.02 (s, 3H), 3.16 (s,3H), 3.51–3.69 (m, 2H), 3.80–3.85 (m, 1H), 4.05–4.08 (m, 2H), 4.95–5.03 (m, 1H), 5.93–6.01 (m, 2H), 7.67 (d, 1H, J=7.2 Hz), 8.62 (s, 1H).

Synthesis of Nucleoside Prodrugs of Formula II

Example 19

General Procedure for the Synthesis of Nucleoside Prodrugs of Formula II

Example 19a

Synthesis of 5'-O-cis-[4-(3-chlorophenyl)-1,3,2-dioxaphosphorin-2-oxo-2-yl]-cytosine-β-D-arabino-furanoside Step A: Phosphorylation Reaction A solution of t-BuMgCl (15.5 mL, 15.5 mmol) in THF was added to a solution of the 2',3'-di-O-TBS-cytosine-β-D-arabinofuranoside (5 g, 10.3 mmol) in THF (300 mL) at room temperature. The tan solution was stirred at room temperature for 30 minutes and the trans-2-(4-nitrophenoxy)-4-(3-chlorophenyl)-2-oxo-1,3,2-dioxaphosphorinane was added in one portion. After stirring at room temperature for 18 hours the tan reaction mixture was quenched with a saturated solution of ammonium chloride (200 mL) and extracted twice with ethyl acetate. The combined organic extracts were washed 3 times with 1 N sodium hydroxide, twice with saturated sodium chloride and dried over sodium sulfate. The filtered solution was concentrated under reduced pressure and the residue was purified by flash column chromatography (silica gel, gradient dichloromethane/ethanol 95/5 to 85/15) to give a light yellow foam (4.48 g, 62%).

TLC conditions: Merck silica gel 60 F254 plates, 250 µm thickness; mobile phase=90/10 dichloromethane/methanol; rf: trans-phosphate=0.9, 4-nitrophenol=0.75, product=0.4, nucleoside=0.3.

¹H NMR (CDCl₃, Varian Gemini 200 MHz): 5.8–5.55 (m, 2H), 2.45–2 (m, 2H), 0.95 (s, 9H), 0.85 (s, 9H), 0.17 (s, 6H), 0.03 (s, 3H), −0.1 (s, 3H).

Step B: Deprotection of the Protected Prodrug

Tetraethylammonium fluoride (2.72 g, 18.3 mmol) was added to a solution of the protected prodrug (4.28 g, 6.1 mmol) in THF (60 mL) at room temperature. The heterogeneous mixture was stirred at room temperature for 18 hours. The thick heterogeneous mixture was concentrated under reduced pressure and partially purified by column chromatography (silica gel, gradient dichloromethane/methanol 85/15 to 60/40). The combined fractions were concentrated and the solid residue was dissolved in 100 mL of 1 N hydrochloric acid then washed twice with dichloromethane. The aqueous layer was filtered and the pH of the solution was raised to 7–8 with 50% sodium hydroxide (a white precipitate started to appear at pH 3 which thickened as the pH continued to rise. After stirring at room temperature overnight, the precipitate was collected by filtration, rinsed with water, air dried then dried under high vacuum at 25° C. to give a white solid (1.62 g, 56%, purity=96%).

TLC conditions: Merck silica gel 60 F254 plates, 250 µm thickness; mobile phase=80/20 dichloromethane/methanol; rf: product=0.15, intermediates=0.7, protected prodrug=0.8.

¹H NMR (DMSO-d₆, Varian Gemini 200 MHz): 6.15 (m, 1H), 5.8–5.65 (m, 1H), 2.3–2.1 (m, 2H).

HPLC conditions: Column=YMC-Pack ODS-AQ 250×46 mm I.D. S-5 µm 120 A; mobile phase gradient acetonitrile in 20 mM phosphate buffer pH 6.2 (T=0 min, 10% ACN), (T=15, 55%), (T=17, 5%), (T=25, 10%); flow rate=1.4 mL/min; detection=UV @ (270 nm; retention times in min: 5'-O-cis-[4-(3-chlorophenyl)-1,3,2-dioxaphosphorin-2-oxo-2-yl]-cytosine-β-D-arabinofuranoside=12.32.

Elemental analysis (Robertson Microlit Laboratories): Calculated for $C_{18}H_{21}ClN_3O_8P$+1 mol $H_2O$: C, 43.96; H, 4.71; N, 8.54. Found: C, 4.79; H, 4.55; N, 8.39.

Example 19b

Synthesis of 5'-O-cis-[4-(4-bromophenyl)-1,3,2-dioxaphosphorin-2-oxo-2-yl]-cytosine-β-D-arabino-furanoside Step A:

Same as Example 19a, Step A

¹H NMR (CDCl₃, Varian Gemini 200 MHz): 6.25–6.15 (m, 1H), 6–5.8 (m, 1H), 2.45–2 (m, 2H), 0.89 (s, 9H), 0.78 (s, 9H), 0.11 (s, 6H), 0.09 (s, 3H), −0.2 (s, 3H).

Step B:

To a solution of protected prodrug (180 mg, 0.24 mmol) in THF (2 mL) was added a 1M solution of TBAF in THF (0.73 mL, 0.73 mmol). After 1 h at room temperature silica gel (3 g) was added to the reaction mixture and the slurry was dried under vacuum before being purified by column chromatography (silica gel, ethyl acetate/methanol) to give the title compound (105 mg, 87%)

mp: 196° C.

¹H NMR (DMSO-d₆, Varian Gemini 200 MHz): 6.15 (m, 1H), 5.75–5.45 (m, 4H), 2.3–2.05 (m, 2H).

Elemental analysis (Robertson Microlit Laboratories): Calculated for $C_{18}H_{21}BrN_3O_8P$+0.8 mol $H_2O$: C, 40.59; H, 4.28; N, 7.89. Found: C, 40.58; H, 3.94; N, 7.52.

Example 19c

Synthesis of 5'-O-cis-[4-(3-chloro-4-fluorophenyl)-1,3,2-dioxaphosphorin-2-oxo-2-yl]-cytosine-β-D-arabinofuranoside Step A:

Same as Example 19a, Step A

¹H NMR (CDCl₃, Varian Gemini 200 MHz): 6.25–6.15 (m, 1H), 6.1–5.85 (m, 1H), 2.4–2 (m, 2H), 0.89 (s, 9H), 0.81 (s, 9H), 0.02 (s, 6H), 0.09 (s, 3H), −0.07 (s, 3H).

Step B: same as Example 19b, Step B mp: 128–131° C.

¹H NMR (DMSO-d₆, Varian Gemini 200 MHz): 6.15–6.05 (m, 1H), 5.8–5.65 (m, 1H), 2.3–2.1 (m, 2H).

Elemental analysis (Robertson Microlit Laboratories): Calculated for $C_{18}H_{20}ClFN_3O_8P$+0.9 mol $H_2O$: C, 42.56; H, 4.33; N, 8.27. Found: C=42.83, H=4.13, N=7.91.

Example 19d

Synthesis of 5'-O-cis-[4-(pyrid-4-yl))-1,3,2-dioxaphosphorin-2-oxo-2-yl]-2'-deoxy-2',2'-difluoro-cytidine Step A:

Same as Example 19a, Step A using 2'-deoxy-2',2'-difluoro-3'-O-TBS-4-N-(N,N-dimethylformamidine)-cytidine TLC conditions: 90/10 dichloromethane/methanol; rf:=0.25.

¹H NMR (CDCl₃, Varian Gemini 200 MHz): 6.5–6.3 (m, 1H), 6.3–6.15 (m, 1H), 5.75–5.6 m, 1H), 3.27 (s, 3H), 3.25 (s, 3H), 2.4–1.6 (m, 2H).

Step B:

The protected prodrug (50 mg) was dissolved in 70% aqueous trifluoroacetic acid and was heated at 50° C. overnight. The cooled solution was concentrated under reduced pressure and purified by column chromatography (silica gel, dichloromethane/methanol) to give the title compound (40 mg)

mp: 150° C.

¹H NMR (CD₃OD, Varian Gemini 200 MHz): 6.35–6.15 (m, 1H), 5.9–5.7 (m, 2H), 2.4–2.2 (m, 2H).

Elemental analysis (Robertson Microlit Laboratories): Calculated for $C_{17}H_{19}CF2N_4O_7P$+0.8 mol $H_2O$: C, 43.01; H, 4.37; N, 11.80. Found: C, 43.34; H, 4.15; N, 11.45.

Example 19e

Synthesis of 5'-O-cis-[4-(3,5-dichlorophenyl))-1,3,2-dioxaphosphorin-2-oxo-2-yl]-2'-deoxy-2',2'-difluoro-cytidine Step A:

Same as Example 19a, Step A using 2'-deoxy-2',2'-difluoro-3'-O-TBS-4-N-(N,N-dimethylformamidine)-cytidine TLC conditions: 90/10 dichloromethane/methanol; rf: 0.45.

¹H NMR (CD₃OD, Varian Gemini 200 MHz): 6.4–6.15 (m, 1H), 6.05–5.9 (m, 1H), 5.8–5.6 (m, 1H), 3.3 (s, 3H), 3.2 (s, 3H), 2.4–2 (m, 2H).

Step B:

Same as Example 19d, Step B mp: >200° C. dec

¹H NMR (CD₃OD, Varian Gemini 200 MHz): 6.35–6.15 (m, 1H), 5.8–5.65 (m, 2H), 2.4–2.1 (m, 2H).

Elemental analysis (Robertson Microlit Laboratories): Calculated for $C_{17}H_{18}Cl_2N_3O_7P$+0.25 mol $H_2O$: C=40.58, H=3.50, N=7.89; Found: C=40.55, H=3.64, N=7.79.

Example 19f

Synthesis of 5'-O-cis-[4-(pyrid-3-yl))-1,3,2-dioxaphosphorin-2-oxo-2-yl]-2'-deoxy-2'-difluoro-cytidine Step A:

Same as Example 19a, Step A using 2'-deoxy-2'-difluoro-3'-O-TBS-4-N-(N,N-dimethylformamidine)-cytidine TLC conditions: 90/10 dichloromethane/methanol; rf:=0.35.

¹H NMR (CD₃OD, Varian Gemini 200 MHz): 6.35–6.1 (m, 1H), 6.1–5.95 (m, 1H), 5.9–5.75 (m, 1H), 3.27 (s, 3H), 3.15 (s, 3H), 2.5–2.1 (m, 2H).

Step B:

Same as Example 19d, Step B mp: >200° C. dec

¹H NMR (CD₃OD, Varian Gemini 200 MHz): 6.3–6.1 (m, 1H), 5.9–5.7 (m, 2H), 2.5–2.1 (m, 2H).

Elemental analysis (Robertson Microlit Laboratories): Calculated for $C_{17}H_{19}F_2N_4O_7P$+1.5 mol $H_2O$: C, 41.90; H, 4.55; N, 11.50. Found: C, 41.96; H, 4.52; N, 11.29.

Synthesis of Single Isomers of Nucleoside Prodrugs of Formula II

The following compounds were synthesized using the corresponding enantioenriched phosphorylating reagent.

Example 20

Synthesis of (4S)-5'-O-cis-[4-(pyrid-4-yl)-1,3,2-dioxaphosphorin-2-oxo-2-yl]-uracil-β-D-arabino-furanoside Step A:

Same as Example 19a, Step A

¹H NMR (CDCl₃, Varian Gemini 200 MHz): 6.25–6.15 (m, 1H), 5.75–5.6 (m, 2H), 2.4–2 (m, 2H).

Step B:

Same as Example 19b, Step B mp: 136–139° C.

¹H NMR (CD₃OD, Varian Gemini 200 MHz): 6.2–6.15 (d, 1H), 5.85–5.7 (m, 1H), 5.55–5.45 (m, 1H), 2.4–2.2 (m, 2H).

Elemental analysis (Robertson Microlit Laboratories): Calculated for $C_{17}H_{20}N_3O_9P$+1.8 mol $H_2O$: C, 43.10; H, 5.02; N, 8.8. Found: C, 43.18; H, 4.95; N, 8.52.

Example 20a

Synthesis of (4S)-5'-O-cis-[4-(3-chlorophenyl)-1,3,2-dioxaphosphorin-2-oxo-2-yl]-cytosine-β-D-arabinofuranoside

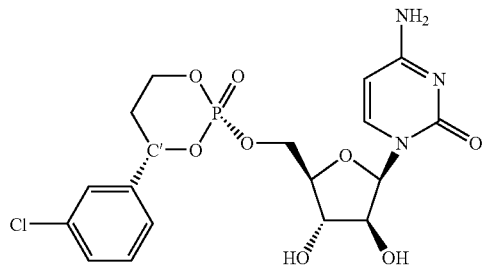

Step A:

Same as Example 19a, Step A

¹H NMR (200 MHz, CDCl₃): 7.81 (1H, d, J=7.7 Hz), 7.2–7.4 (4H, m), 6.27 (1H, broad s), 5.83 (1H, broad s), 5.64 (1H, d, J=8.8 Hz), 4.6–4.8 (1H, m), 4.3–4.6 (2H, m), 4.1–4.3 (3H, m), 2.0–2.4 (2H, m), 0.79 (9H, s), 0.78 (9H, s), 0.091 (3H, s), 0.03 (3H, s), 0.02 (3H, s), −0.15 (3H, s)

Step B:

Same as Example 19a, Step B

¹H NMR (200 MHz, DMSO-d₆): 7.52 (1H, d, J=7.32 Hz), 7.3–7.5 (4H, m), 7.07 (2H, broad s), 6.10 (1H, m), 5.5–5.8 (4H, m), 4.2–4.6 (4H, m), 3.8–4.0 (3H, m), 2.1–2.3 (2H, m).

m.p.: >200° C. $[\alpha]_D$=+55.16. Elemental Analysis: Calculated for $C_{18}H_{21}N_3O_8ClP$+0.8$H_2O$: C, 44.28; H, 4.67; N, 8.61. Found: C, 44.32; H, 4.47; N, 8.42.

Example 20b

Synthesis of (4R)-5'-O-cis-[4-(3-chlorophenyl)-1,3,2-dioxaphosphorin-2-oxo-2-yl]-cytosine-β-D-arabinofuranoside

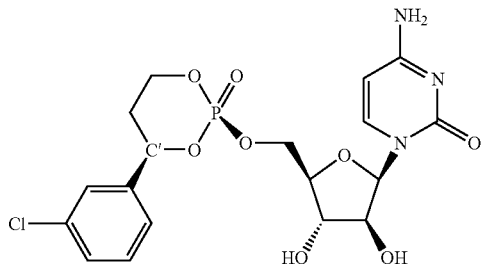

Step A:
Same as Example 19a, Step A

Step B:
Same as Example 19a, Step B $^1$H NMR (200 MHz, DMSO-d$_6$): 7.4–7.6 (5H, m), 7.07 (2H, broad s), 6.10 (1H, d, J=3.3 Hz), 5.71 (1H, m), 5.6–5.7 (3H, m), 4.2–4.6 (4H, m), 3.8–4.0 (3H, m), 2.1–2.3 (2H, m).

m.p.: >200° C. [α]$_D$=+91.40. Elemental Analysis: Calculated for C$_{18}$H$_{21}$N$_3$O$_8$ClP+0.7 H$_2$O: C: 44.45, H: 4.64, N: 8.64. Found: C: 44.53, H: 4.45, N: 8.43.

Example 20c

Synthesis of (4S)-5'-O-cis-[4-(S)-(pyrid-4-yl)-1,3,2-dioxaphosphorin-2-oxo-2-yl]-cytosine-β-D-arabinofuranoside (also known as 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl])

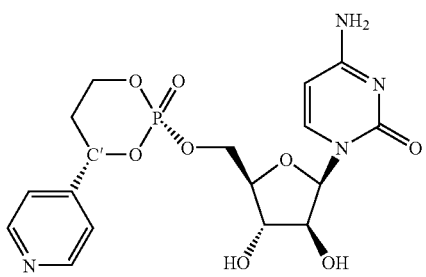

A 50 L, 3-neck round bottom flask was equipped with an overhead stirrer, thermowell/thermometer, addition funnel (2 L) and cooling bath. The flask was flushed with nitrogen and charged with a solution of 2',3'-di-O-TBS-4-N-(N,N-dimethylformamidine)-cytosine-β-D-arabinofuranoside (1.46 kg, 2.46 mol) in THF (12.5 L). The stirred solution was cooled to 5° C. (ice bath). A t-butylmagnesium chloride solution (2.85 L, 3.19 mol) was added over 1.2 h, maintaining the temperature ≦10° C. After the addition was complete, the solution was stirred at ice bath temperature for 1.25 h. The phosphate reagent (S)-(−)-trans-(4-pyridyl)-2-(4-nitrophenoxy)-2-oxo-1,3,2-dioxaphosphorinane (1.36 kg, 4.04 mol) was added in one portion then the cooling bath was drained. The resulting mixture was stirred at ambient temperature for 17.5 h. The reaction was quenched with ammonium chloride solution (20 wt %, 12 L) and diluted with ethyl acetate (12 L). The mixture was stirred for 30 minutes to dissolve all residues, and the layers were separated. The aqueous phase was back-extracted with ethyl acetate (4 L) and the combined organic phase was washed with sodium chloride solution (15 wt %, 8 L), dried over MgSO$_4$ (1.38 kg), filtered and concentrated under reduced pressure to provide 2.85 kg of a dark sludge.

A 22 L, 4-neck round bottom flask was equipped with an overhead stirrer, thermowell/thermometer, condenser with base trap/bubbler, and heating mantle. The flask was charged with the crude sludge as a solution in methanol (12 L). HCl-dioxane solution (4.1 L, 6.66 mol) was added and the stirred orange solution was heated at 50–55° C. for 16 h with monitoring by HPLC. The solvent was evaporated under reduced pressure to give a thick orange tar weighing 2.88 kg. The tar was partitioned between water (3.5 L) and ethyl acetate (3.5 L). Solid sodium bicarbonate was added portionwise until the pH of the aqueous phase was 7.0 (pH meter). The layers were separated and the aqueous phase was extracted again with ethyl acetate (3.5 L). The aqueous phase was filtered and the water was evaporated on a rotary evaporator (vacuum pump, bath temp=55° C.). When most of the water was removed, ethanol (3 L) was added to the residue (KF of mixture=10.59%) and evaporation continued (aspirator pump, bath temp=55° C.). Ethanol (3 L) was added (KF of mixture=4.49%) and evaporation continued. Ethanol (3 L) was added (KF of mixture=1.45%) and the slurry was stirred in an ice bath for 1.25 h (Temp.=3° C.). The resulting mixture was filtered and the collected solid was washed with ethanol (1 L). The solid was dried to a constant weight (−30 in. Hg, 55° C., 2 h) to provide 1005 g of a beige solid.

The crude product was further purified as follows:

A 22 L, 3-neck round bottom flask was equipped with an overhead stirrer and charged with the crude 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] (2.91 kg) and water (14.5 L). The slurry was stirred and concentrated hydrochloric acid was added portionwise until the solids were dissolved (355 mL required, pH=3.9 by pH meter). Celite 521® (175 g) was added and the mixture was filtered through a Celite pad (100 g) in a 24 cm Buchner funnel. The solution was charged to a 50 L flask equipped with an overhead stirrer and solid sodium bicarbonate (393 g) was added portionwise until the pH of the mixture was 6.3 (pH meter). The resulting mixture was stirred at ambient temperature for 2 h then filtered. The collected solid was washed with water (500 mL) and dried to constant weight (−30 in. Hg, 55° C., 16 h), giving 1.08 kg of 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] as a brown granular solid (35% yield).

KF=2.0%

Sodium content=0.07%

Elemental analysis calculated for C$_{17}$H$_{21}$N$_4$O$_8$P+0.5 H$_2$O (MW 449.36): C, 45.44; H, 4.93; N, 12.47. Found: C, 45.56; H, 4.70; N, 12.48.

HPLC conditions:

Columns: Two of following in serial connection; Agilent, Zorbax Eclipse XDB-C8, 4.6×250 mm, 5 µm; Solvent A=20 mM sodium phosphate buffer in 11% acetonitrile/water; solvent B=50% acetonitrile in de-ionized water; reversed phased; flow rate=1.0 mL/min; injection volume=10 µL UV detection at 210 nm, column temperature=30° C.

r.t.=13.4 min (S-isomer)

r.t.=14.1 min (R-isomer)

$^1$H NMR (DMSO-d$_6$): δ 2.15–2.27 (m, 2H), 3.90–3.97 (m, 3H), 4.24–4.58 (m, 4H), 5.58 (d, 1H, J 7.4 Hz), 5.62–5.65 (m, 2H), 5.71–5.79 (m, 1H), 6.10 (d, 1H, J 3.6 Hz), 7.08 (s, 1H), 7.13 (s, 1H), 7.42 (d, 2H, J 5.8 Hz), 7.48 (d, 1H, J 7.4 Hz), 8.59 (d, 2H, J 6.0 Hz)

Example 20d

Synthesis of (4S)-5'-O-cis-[4-phenyl-1,3,2-dioxaphosphorin-2-oxo-2-yl]-adenine-β-D-arabinofuranoside Step A:
Same as Example 19a, Step A
TLC: dichloromethane/methanol 95/5); Rf=0.35
$^1$H NMR (DMSO-$d_6$, Varian Gemini 300 MHz): 6.85–6.8 (d, 1H), 6.2–6.1 (m, 1H), 2.7–2.55 (m, 2H), 1.37 (s, 9H), 1.09 (s, 9H), 0.62 (s, 3H), 0.61 (s, 3H), 0.4 (s, 3H), 0.00 (s, 3H).

Step B:
same as Example 19a, Step B
mp: 130–134° C.
$^1$H NMR (DMSO-d6, Varian Gemini 300 MHz): 6.35–6.25 (d, 1H), 5.7–5.6 (m, 1H), 2.3–2 (m, 2H).
Elemental analysis (Robertson Microlit Laboratories): Calculated for $C_{19}H_{22}N_5O_7P+1$ mol $H_2O+0.2$ mol $CH_2Cl_2$: C, 46.27; H, 4.93; N, 14.05. Found: C, 46.09; H, 4.47; N, 13.94.

Example 20e

Synthesis of (4S)-5'-O-cis-[4-(pyrid-4-yl)-1,3,2-dioxaphosphorin-2-oxo-2-yl]-adenine-β-D-arabinofuranoside Step A:
Same as Example 19a, Step A
TLC: dichloromethane/methanol 9/1); Rf=0.3
$^1$H NMR (DMSO-$d_6$, Varian Gemini 300 MHz): 6.85–6.8 (d, 1H), 6.25–6.15 (m, 1H), 2.8–2.5 (m, 2H), 1.37 (s, 9H), 1.08 (s, 9H), 0.62 (s, 6H), 0.4 (s, 3H), 0.00 (s, 3H)

Step B:
same as Example 19a, Step B
mp: >210° C. dec
$^1$H NMR (DMSO-$d_6$, Varian Gemini 300 MHz): 6.35–6.25 (d, 1H), 5.8–5.65 (m, 1H), 2.3–2 (m, 2H).
Elemental analysis (Robertson Microlit Laboratories): Calculated for $C_{18}H_{21}N_6O_7P+0.5$ mol $H_2O$: C, 45.67; H, 4.68; N, 17.75. Found: C, 45.36; H, 4.74; N, 17.46.

One-step Synthesis of Nucleoside Prodrugs of Formula II

Example 21a

Synthesis of 5'-O-cis-[4-(3-chlorophenyl)-1,3,2-dioxaphosphorin-2-oxo-2-yl]-cytosine-β-D-arabinofuranoside A solution of 4 N HCl in dioxane was added to a suspension of 5 g of cytarabine in 10 mL of DMPU. After stirring at room temperature for 10 minutes, a clear solution was obtained. To this solution was added 5.5 grams of the phosphorochloridate trans-2-chloro-4-(3-chlorophenyl)-2-oxo-1,3,2-dioxaphosphorinane in one portion. The phosphorinane slowly dissolved and the solution became very thick rending stirring difficult. After 16 hours at room temperature. An additional 3.79 grams of phosphorochloridate was added. Stirring was continued at room temperature for 24 hours upon which 10% of starting of ara-C was still present in the reaction mixture. The reaction mixture was diluted with 50 mL of dichloromethane and 15 mL of water. The layers were separated and the organic layer was further extracted six times with 25 mL of water. The combined aqueous extracts (total volume of water=175 mL) were filtered and back extracted with 25 mL of dichloromethane to remove the last traces of DMPU. The aqueous phase was then neutralized with approximately 5.4 eq (9.35 g) of sodium bicarbonate and a white solid precipitated as the pH rose. The heterogeneous mixture was stirred at room temperature for 9 hours and the solid was filtered and rinsed with water. The white solid was further dried in an oven at 40° C. under reduced pressure overnight to give 6.4 g of crude product. This compound was determined to be a 91/9 mixture of cis and trans isomers by HPLC. Recrystallization from ethanol improved this ratio to 96.5/3.5. A second recrystallization further improved the ratio to 98.8/1.2.

$^1$H NMR (DMSO-$d_6$, Varian Gemini 200 MHz): See Example 19a, step B HPLC: YMC-Pack R-33-5 250×39 mm I.D. S-5 μm 120A; mobile phase=mobile phase gradient acetonitrile in 20 mM phosphate buffer pH 6.2 (T=0 min, 10% ACN), (T=15, 60%), (T=17, 10%), (T=20, 10%); flow rate=1.4 mL/min; detection=UV @ 270 nm; retention times in min: 5'-O-cis-[4-(3-chlorophenyl)-1,3,2-dioxaphosphorin-2-oxo-2-yl]-cytosine-β-D-arabinofuranoside=9.7, (R)-trans isomer=9.975, (S)-trans isomer=10.5.

TLC conditions: Merck silica gel 60 F254 plates, 250 μm thickness mobile phase=9/1 dichloromethane/methanol. Rf: cytarabine=0.03, product=0.17.

Example 21b

Synthesis of (4S)-5'-O-cis-[4-(3-chlorophenyl)-1,3,2-dioxaphosphorin-2-oxo-2-yl]-cytosine-β-D-arabinofuranoside

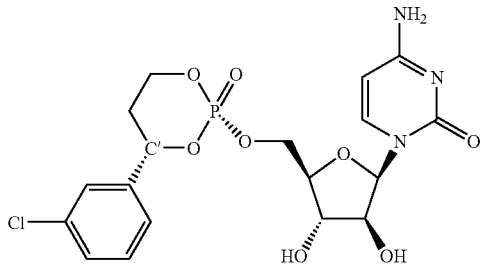

Same as Example 21a
$^1$H NMR (200 MHz, DMSO-$d_6$): 7.52 (1H, d, J=7.32 Hz), 7.3–7.5 (4H, m), 7.07 (2H, broad s), 6.10 (1H, m), 5.5–5.8 (4H, m), 4.2–4.6 (4H, m), 3.8–4.0 (3H, m), 2.1–2.3 (2H, m).
m.p.: >200° C. $[\alpha]_D$=+55.16. Elemental Analysis: Calculated for $C_{18}H_{21}N_3O_8ClP+0.8H_2O$: C, 44.28; H, 4.67; N, 8.61. Found: C, 44.32; H, 4.47; N, 8.42.

Example 21c

Synthesis of (4R)-5'-O-cis-[4-(3-chlorophenyl)-1,3,2-dioxaphosphorin-2-oxo-2-yl]-cytosine-β-D-arabinofuranoside

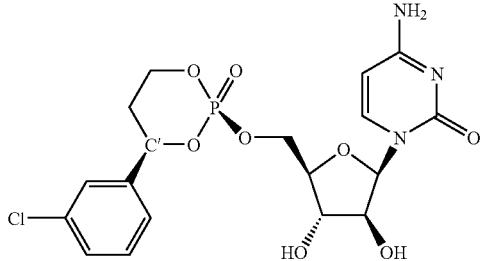

Same as Example 21a
$^1$H NMR (200 MHz, DMSO-$d_6$): 7.4–7.6 (5H, m), 7.07 (2H, broad s), 6.10 (1H, d, J=3.3 Hz), 5.71 (1H, m), 5.6–5.7 (3H, m), 4.2–4.6 (4H, m), 3.8–4.0 (3H, m), 2.1–2.3 (2H, m).

m.p.: >200° C. $[\alpha]_D$=+91.40. Elemental Analysis: Calculated for $C_{18}H_{21}N_3O_8ClP+0.7 H_2O$: C, 44.45; H, 4.64; N, 8.64. Found: C, 44.53; H, 4.45; N, 8.43.

Example 21d

Synthesis of 5'-O-cis-[4-(S)-(pyrid-4-yl)-1,3,2-dioxaphosphorin-2-oxo-2-yl]-cytosine-β-D-arabinofuranoside (also known as 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl])

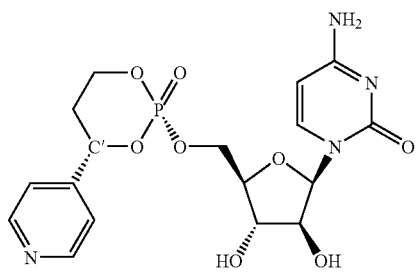

Method A:

In an oven-dried 250 mL RB flask equipped with a magnetic stir bar was charged with 3.35 g of cytarabine-HCl and 6.0 mL of DMPU. Into this flask, a solution of trans-4-(S)-(−)-(4-pyridyl)-2-chloro-1,3,2-dioxaphosphorin-2-one from Example 14b was filtered directly and the DABCO-HCl salt was washed quickly with acetonitrile (1×15 mL). Volatiles were removed on a roto-vap under aspirator vacuum (bath temp <35 C). The residual oil was briefly kept under high vac and stirred at room temperature for 48 h. A tiny sample was pulled out and dissolved in the mobile phase buffer for HPLC.

The reaction mixture was treated with 100 mL of MeOH and stirred for 2 hours at room temperature. The pH of the reaction mixture was adjusted to 7.0 using 25 wt % NaOMe solution in methanol (approximately 13 mL were required). At this stage the reaction mixture was turbid. HPLC was run to insure integrity of the reaction profile. The reaction mixture was evaporated to dryness and the residue was stirred with 50 mL of dichloromethane for 30 minutes at room temperature. The precipitate was collected by filtration, washed with methylene chloride (1×20 mL) and transferred back to the flask, stirred again with 50 mL of dichloromethane for 15 minutes and filtered. The solid was stirred with 200 mL of ethanol for 1–2 hours, filtered and washed with ethanol (2×10 mL). HPLC of the solid (1708-143-soild1) indicated mostly impurities with about 20–25% desired product, whereas HPLC of the filtrate (1708-143-ethanol) indicated mostly the desired product. The filtrate was evaporated to dryness to give 4.90 g of a white solid. This solid was dissolved in 10 mL of $H_2O$ and stirred at room temperature overnight to give a solid which was collected by filtration, washed with water (2×3 mL) and dried in a vacuum oven to give 2(1H)-Pyrimidinone, 4-amino-1-[5-O-[(2R,4S)-2-oxido-4-(4-pyridinyl)-1,3,2-dioxaphosphorinan-2-yl]-β-D-arabinofuranosyl] (1.38 g, 26%).

Method B:

Step A: Synthesis of Cytarabine Hydrochloride

A 5 L, 3-neck flask equipped with an overhead stirrer and thermocouple was charged with cytarabine (500 g, 2.06 mol) and methanol (2.0 L). The suspension was cooled to 2° C.

HCl gas was bubbled in, giving a very thick mixture and an exotherm to 25° C. The suspension was diluted with methanol (0.5 L) to facilitate stirring. A total of 108 g (2.96 mol) of HCl gas was added. The mixture was stirred for 4 hours at 20° C. then filtered to collect the solid. The solid was washed with MTBE (3×250 mL) and dried in a vacuum oven at 70° C. to give 555 g (96% yield) of cytarabine hydrochloride as a flocculent, white solid.

Step B: Synthesis of 5'-O-cis-[4-(S)-(pyrid-4-yl)-1,3,2-dioxaphosphorin-2-oxo-2-yl]-cytosine-β-D-arabinofuranoside A 1 L jacketed cylindrical reactor was equipped with an overhead stirrer, thermocouple, and two addition funnels (60 mL and 125 mL). The reactor was flushed with nitrogen and charged with DMPU (188 mL, 195.8 g). The stirred liquid was cooled to −16° C. (Julabo F32 chiller/circulator).

Diol solution: A 250 mL round bottom flask was equipped with a magnetic stir bar and thermometer. The flask was charged with S-(−)-1-(pyrid-4-yl)-1,3-propanediol (50.0 g), DMPU (62.5 mL, 64.5 g) and pyridine (25.8 g) then placed under a nitrogen atmosphere. The stirred contents were heated to 40° C. (water bath) and stirred at 40–42° C. until all solids were dissolved (10 minutes). The resulting pale orange solution was cooled to 22° C. then charged to the 125 mL addition funnel (volume=127 mL).

$POCl_3$ solution: A 125 mL Erlenmeyer flask was charged with acetonitrile (22.9 g) and phosphorus oxychloride (50.0 g). After mixing well, the colorless solution was transferred to the 60 mL addition funnel (volume=60 mL).

The two solutions were added simultaneously into the 1 L reactor over 2.6 h, maintaining the temperature below −11° C. After the additions were complete, the viscous pale orange solution was stirred, maintaining the temperature between −11 and −17° C. for 1 h. A sample of the reaction solution was pulled and checked for reaction completion by HPLC (aliquots were hydrolyzed to the cyclic phosphoric acid and then analyzed by HPLC). Cytarabine hydrochloride (60.9 g) was added. The resulting mixture was warmed to 5° C. over 1 h and stirred at 4–6° C. for 87 h. The resulting viscous reaction solution was sampled daily for HPLC analysis. The stirred reaction solution was slowly quenched with NaOH solution (13% wt/vol) at such a rate to maintain the temperature ≦20° C., until the pH of the solution reached 5.0 (290 mL of NaOH solution required). Dichloromethane (450 mL) was added and the biphasic mixture was stirred at 15–20° C. for 30 minutes. Stirring was stopped and the mixture was allowed to settle for 30 minutes. The lower organic layer was separated. The upper aqueous layer was extracted twice more with dichloromethane (450 mL, 30-minute stir, 30-minute settle) (Note 5). The reactor was fitted with a pH probe and NaOH solution (13% wt/vol) was added over 10 minutes to pH 7.0 (68 mL of NaOH solution required). Cooling (5° C.) was applied to the jacket to keep the temperature below 20° C. The resulting solution was stirred at ambient temperature for 20 h then cooled to 5° C. for 5 h (Note 6). The resulting mixture was filtered and the collected solid was washed with water (2×100 mL) and dried to constant weight (−30 in. Hg, 60° C., 18 h). Recovery=46.6 g of a pale yellow, fine granular solid (48% yield).

HPLC for phosphorochloridate synthesis:

Column: Zorbax Eclipse XDB-C8, 4.6×250 mm, 5 μm particle size; Solvent A=20 mM sodium phosphate buffer in 11% acetonitrile/water; solvent B=50% acetonitrile in deionized water (gradient 100% A to 100% B in 15 minutes); flow rate=1.0 mL/min; injection volume=10 μL UV detection at 250 nm, column temperature=30° C.

r.t.=4.3 min

HPLC for 5'-O-cis-[4-(S)-(pyrid-4-yl)-1,3,2-dioxaphosphorin-2-oxo-2-yl]-cytosine-β-D-arabinofuranoside:

Columns: Inertsil ODS-3, 4.6×150 mm, 3 μm particle size; Solvent A=20 mM ammonium phosphate buffer in 5% acetonitrile/water; solvent B=acetonitrile (gradient (time in minutes/% B in A %): 0/0, 30/10, 40/40, 40.1/0, 50/0); flow rate=1.0 mL/min; injection volume=50 μL UV detection at 210 nm, column temperature=30° C.±5° C.

r.t.=15.7 min

Step C: Purification of 5'-O-cis-[4-(S)-(pyrid-4-yl)-1,3,2-dioxaphosphorin-2-oxo-2-yl]-cytosine-β-D-arabinofuranoside Procedure 1: A 1 L, 3-neck flask equipped with an overhead stirrer, thermometer, addition funnel, and pH probe was charged with crude 5'-O-cis-[4-(S)-(pyrid-4-yl)-1,3,2-dioxaphosphorin-2-oxo-2-yl]-cytosine-β-D-arabinofuranoside (80 g, 0.18 mol) and deionized water (256 mL). The pH of the mixture was 5.16. Sulfuric acid, 3.0 M (60.6 mL, 0.18 mol) was added dropwise over 10 minutes. A 10° C. cooling bath was used to keep the temperature between 19–22° C. A slightly turbid, yellow solution resulted. The solution was filtered through a 0.45 μm nylon membrane filter (47 mm diameter). The flask and filter were rinsed with water (40 mL). The filtrate and washings were returned to the 1 L flask and the pH adjusted to 6.5 by adding 3 M NaOH (155 mL) and 3 M sulfuric acid. Precipitate formation was observed beginning at pH 5.1. The mixture was stirred 2.5 h then filtered to collect the solid. The flask and filter cake were washed with water (2×80 mL) and dried in a vacuum oven overnight (−30 in. Hg, 60° C., 18 h) to give 73.4 g of 5'-O-cis-[4-(S)-(pyrid-4-yl)-1,3,2-dioxaphosphorin-2-oxo-2-yl]-cytosine-β-D-arabinofuranoside as a coarse, pale yellow solid (92% yield).

Procedure 2: A 250 mL, 3-neck flask equipped with an overhead stirrer, thermocouple, addition funnel, and pH probe was charged with crude 5'-O-cis-[4-(S)-(pyrid-4-yl)-1,3,2-dioxaphosphorin-2-oxo-2-yl]-cytosine-β-D-arabinofuranoside (16 g, 36.3 mmol) and deionized water (50 mL). Aqueous sulfuric acid, 3.0 M was added dropwise to pH 2.5 (12 mL, 36.3 mmol), keeping the temperature below 22° C. Methanol (160 mL) was added over 20 minutes, giving a white precipitate. The suspension was stirred at 20° C. for 1.5 h then filtered to collect the solid. The solid was washed with methanol (2×25 mL) and dried in a vacuum oven (−30 in. Hg, 60° C., 1.5 h) to give 18.89 g of the sulfuric acid salt.

The solid was charged to a 250 mL, 3-neck flask equipped with an overhead stirrer and pH probe. Water (180 mL) was added and the mixture was stirred for 10 minutes to dissolve all the solids (pH=2.7). Sodium phosphate monobasic monohydrate (0.25 g, 1.81 mmol) was added and the mixture was stirred for 5 minutes. The solution was filtered through Celite. The filtrate was returned to the flask and 13% (wt/vol) aqueous NaOH was added to pH 7.1. The suspension was stirred at 20° C. for 3 hours. The solid was collected by filtration, washed with water (2×15 mL), and dried in a vacuum oven (−30 in. Hg, 60° C., 16 h) to a constant weight, giving 13.55 g (85% yield) of 5'-O-cis-[4-(S)-(pyrid-4-yl)-1,3,2-dioxaphosphorin-2-oxo-2-yl]-cytosine-β-D-arabinofuranoside as an off-white, granular solid.

Use of Magnesium Salts for Phosphorylation Step

Example 22

Synthesis of 5'-O-cis-[4-(3-chlorophenyl)-1,3,2-dioxaphosphorin-2-oxo-2-yl]-cytosine-β-D-arabinofuranoside Potassium t-butoxide (1.1 mmol) is added to a solution of 2',3'-di-O-TBS-cytosine-β-D-arabinofuranoside (1 mmol) in THF at room temperature. After stirring at room temperature for 1 hour, magnesium chloride (2 mmol) is added followed by a solution of the phosphorylating agent trans-2-(4-nitrophenoxy)-4-(3-chlorophenyl)-2-oxo-1,3,2-dioxaphosphorinane (1.5 mmol) in THF at room temperature. After stirring at room temperature for 16 hours, the reaction mixture is quenched with the addition of a saturated solution of ammonium chloride. The reaction mixture was extracted twice with ethyl acetate. The combined organic extracts were washed with 0.3 N sodium hydroxide, brine, dried over sodium sulfate and concentrated under reduced pressure. The residue was purified by column chromatography as in Example 19a step A.

Step B:
Same as Example 19a, step B.

We claim:

1. A method of making a compound of Formula II.A or Formula II.B or salt thereof

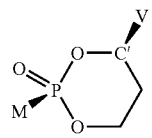

Formula II.A

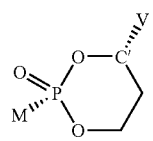

Formula II.B said method comprising:
(a) isomerizing a mixture of trans/cis isomers of the compound of Formula I to give a ratio of trans/cis of about 85/15 or greater;

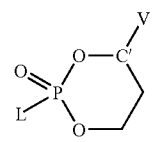

Formula I wherein:
V and L are trans relative to one another;
V is selected from the group consisting of heteroaryl, and phenyl, all optionally substituted with 1–4 substituents;
L is selected from the group consisting of halogen, and aryloxy optionally substituted with 1–2 substituents; and
(b) reacting the compound of Formula I having the ratio of trans/cis isomers of about 85/15 or greater, or salt thereof, with MH, wherein:
MH is selected from the group consisting of protected and unprotected oncolytic agents and antiviral agents and wherein:
H is attached to O, S, or N of said oncolytic and antiviral agents; and
M is attached to phosphorus via an oxygen, nitrogen or sulfur atom.

2. The method of claim 1, wherein said isomerizing comprises treating the mixture of trans/cis isomers of the compound of Formula I with L⁻ to give the ratio of trans/cis isomers of about 85/15 or greater.

3. The method of claim 1, wherein said isomerizing comprises heating the mixture of trans/cis isomers of the compound of Formula I to give the ratio of trans/cis isomers of about 85/15 or greater.

4. The method of claim 3, wherein said heating is from 40° C. to 70° C.

5. The method of claim 1, wherein said isomerizing comprises isolating the cis isomer from the mixture of trans/cis isomers of Formula I and treating the cis isomer with L⁻ to give the ratio of trans/cis isomers of about 85/15 or greater.

6. The method of claim 1, wherein M is attached to phosphorus via an oxygen present in a primary hydroxyl on MH.

7. The method of claim 1, wherein M is attached to phosphorus via an oxygen present in a hydroxyl group on an acyclic sugar in MH.

8. The method of claim 1, wherein MH is reacted with the compound of Formula I in the presence of a base.

9. The method of claim 1, wherein MH is a protected nucleoside and further comprising the steps of:
forming an anion of MH with a base; and
adding the compound of Formula I or salt thereof to said anion.

10. The method of claim 1, wherein MH is an unprotected nucleoside, and wherein the compound of Formula I or salt thereof is added to MH or salt thereof.

11. The method of claim 8, wherein said base is R'MgX' wherein:
R' is selected from the group consisting of C1–C5 alkyl, and aryl optionally substituted with 1–3 substituents; and
X' is halogen.

12. The method of claim 11, wherein said base is selected from the group consisting of tert-BuMgCl, and phenylMgCl.

13. The method of claim 11, wherein said base is tert-BuMgCl.

14. The method of claim 1, further comprising:
forming an anion of a protected nucleoside with a base;
adding a Lewis acid; and
adding the compound of Formula I.

15. The method of claim 1, wherein MH is a nucleoside, and further comprising:
forming an anion of MH with a base;
adding a Mg salt; and
generating the Mg salt of said anion.

16. The method of claim 15, wherein said base is selected from the group consisting of alkali hydride, organometallic base, trialkylamine, and N-containing heteroaryl base.

17. The method of claim 15, wherein:
said base is selected from the group consisting of sodium hydride (NaH), lithium hydride (LiH), lithium diethylamide (LDA), lithium hexamethyldisilazide (LHMDS), potassium t-butoxide (t-BuOK), butyl lithium (BuLi), triethylamine (Et₃N), diisopropylethylamine, 1,8-diazabicyclo[5.4.0]undec-7-ene (DBU), diazabicyclo[2.2.2]octane (DABCO), and pyridine.

18. The method of claim 15, wherein said salt is selected from the group consisting of MgCl₂, MgBr₂, and MgI₂.

19. The method of claim 15, wherein said base is NaH and said salt is MgCl₂.

20. The method of claim 15, wherein said base is t-BuOK and said salt is MgCl₂.

21. The method of claim 15, wherein said base is BuLi and said salt is MgCl₂.

22. The method of claim 15, wherein said base is 1,8-diazabicyclo[5.4.0]undec-7-ene (DBU) and said salt is MgCl₂.

23. The method of claim 15, wherein said base is Et₃N and said salt is MgCl₂.

24. The method of claim 1, wherein said oncolytic agent or antiviral agent is selected from the group consisting of araA (9-β-D-arabinofuranosyladenine); AZT (3'-azido-2',3'-dideoxythymidine); d4T (2',3'-didehydro-3'-deoxythymidine); ddI (2',3'-dideoxyinosine); ddA (2',3'-dideoxyadenosine); ddC (2',3'-dideoxycytidine); L-ddC (L-2',3'-dideoxycytidine); L-FddC (L-2',3'-dideoxy-5-fluorocytidine); L-d4C (β-L-2',3'-didehydro-2',3'-dideoxycytidine); L-Fd4C (β-L-2',3'-didehydro-2',3'-dideoxy-5-fluorocytidine); 3TC ((−)-2',3'-dideoxy-3'-thiacytidine); ribavirin (1-β-D-ribofuranosyl-1,2,4-triazole-3-carboxamide); 5-fluoro-2'-deoxyuridine; FIAU (1-(2'-deoxy-2'-fluoro-β-D-arabinofuranosyl)-5-iodouridine); FIAC (1-(2'-deoxy-2-fluoro-β-D-arabinofuranosyl)-5-iodocytosine); BHCG ((±)-(1α,2α,3α)-9-[2',3'-bis(hydroxymethyl)cyclobutyl]-guanine); L-FMAU (2'-Fluoro-5-methyl-β-L-arabinofuranosyluracil); BvaraU (1'-β-D-arabinofuranosyl-E-5-(2-bromovinyl)uracil); E-5-(2-bromovinyl)-2'-deoxyuridine); TFT (Trifluorothymidine); 5-propynyl-1'-arabinofuranosyluracil; CDG (carbocyclic 2'-deoxyguanosine); DAPD ((−)-β-D-2,6-diaminopurine dioxolane); FDOC ((−)-β-D-5-fluoro-1-[2'-(hydroxymethyl)-1',3'-dioxolane]cytosine); d4C (-2',3'-didehydro-2',3'-dideoxy-cytidine); DXG (dioxolane guanosine); FEAU (2'-deoxy-2'-fluoro-1'-β-D-arabinofuranosyl-5-ethyluracil); FLG (2',3'-dideoxy-3'-fluoroguanosine); FTC ((−)-cis-5-fluoro-1-[2'-(hydroxymethyl)-1',3'-oxathiolan-5'-yl]-cytosine); L-dC (β-L-2'-deoxycytosine); L-dT (β-L-2'-deoxythymidine); 5-yl-carbocyclic-2'-deoxyguanosine; oxetanocin A (9-(2'-deoxy-2'-hydroxymethyl-β-D-erythro-oxetanosyl)adenine); oxetanocin G (9-(2'-deoxy-2'-hydroxymethyl-β-D-erythro-oxetanosyl)guanine); Cyclobut A ((+/−)-9-[(1'-β,2'-α,3'-β)-2',3'-bis(hydroxymethyl)-1'-cyclobutyl]adenine); Cyclobut G ((+/−)-9-[(1'-β,2'-α,3'-β)-2,3-bis(hydroxymethyl)-1-cyclobutyl]guanine); dFdC (2',2'-difluoro-2'-deoxycytidine); araC (arabinofuranosylcytosine); bromodeoxyuridine; IDU (5-iodo-2'-deoxyuridine); CdA (2-chloro-2'-deoxyadenosine); FaraA (2-fluoroarabinofuranosyladenosine); Coformycin; 2'-deoxycoformycin; araT (1-β-D-arabinofuranoside thymidine); tiazofurin; ddAPR (2,6-diaminopurine-2',3'-dideoxyriboside); 9-(arabinofuranosyl)-2,6-diaminopurine; 9-(2'-deoxyribofuranosyl)-2,6-diaminopurine; 9-(2'-deoxy-2'-fluororibofuranosyl)-2,6-diaminopurine; 9-(arabinofuranosyl)guanine; 9-(2'-deoxyribofuranosyl)guanine; 9-(2'-deoxy-2'-fluororibofuranosyl)guanine; FMDC ((E)-2'-deoxy-2'(fluoromethylene)cytidine); DMDC (2'-deoxy-2'-methyledene-cytidine); 4'-thio-araC (4'-thio-arabinofuranosyl-cytidine); 5,6 dihydro-5-azacytidine; 5-azacytidine; 5-aza-2'-deoxycytidine; AICAR (5-aminoimidazole-4-carboxamido-1-ribofuranosyl); NK-84-0218; AM365; MCC₄₇₈; ICN 2001; Fluor L and D nucleosides; Famoiclovir (2-[2-(2-amino-9H-purin-9-yl)ethyl]-1,3-propanediol diacetate); ACV (9-(2'-hydroxyethoxymethyl)guanine); GCV (9-(1',3'-dihydroxy-2'-propoxymethyl)guanine); penciclovir (9-(4'-hydroxy-3'-hydroxymethylbut-1'-yl)guanine); (R)-9-(3',4'-dihydroxybutyl)guanine, cytallene (1-(4'-hydroxy-1',2'- butadienyl)cytosine), and 2'-β-methyl-ribofuranosyl nucleosides of Formula III:

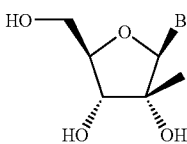

Formula III wherein:
B is selected from the group consisting of

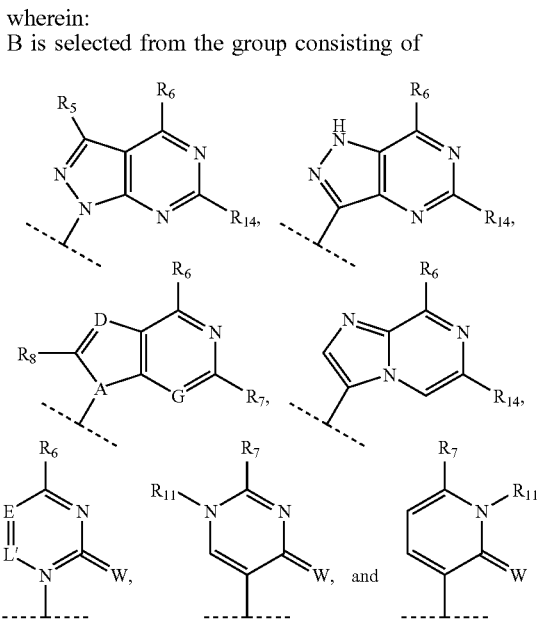

wherein:
A, G, and L' are each independently CH or N;
D is N, CH, C—CN, C—NO$_2$, C—C$_{1-3}$ alkyl, C—NH-CONH$_2$, C—CONR$^{11}$R$^{11}$, C—CSNR$^{11}$R$^{11}$, C—COOR$^{11}$, C—C(=NH)NH$_2$, C-hydroxy, C—C$_{1-3}$ alkoxy, C-amino, C—C$_{1-4}$ alkylamino, C-di(C$_{1-4}$ alkyl)amino, C-halogen, C-(1,3oxazol-2-yl), C-(1,3-thiazol-2-yl), or C-(imidazol-2-yl); wherein alkyl is unsubstituted or substituted with one to three groups independently selected from halogen, amino, hydroxy, carboxy, and C$_{1-3}$ alkoxy;
E is N or CR$^5$;
W is O or S;
R$^5$ is H, C$_{1-6}$ alkyl, C$_{2-6}$ alkenyl, C$_{2-6}$ alkynyl, C$_{1-4}$ alkylamino, CF$_3$, or halogen;
R$^6$ is H, OH, SH, NH$_2$, C$_{1-4}$ alkylamino, di(C$_{1-4}$ alkyl)amino, C$_{3-6}$ cycloalkylamino, halogen, C$_{1-4}$ alkyl, C$_{1-4}$ alkoxy, or CF$_3$;
R$^7$ is H, amino, C$_{1-4}$ alkylamino, C$_{3-6}$ cycloalkylamino, or di(C$_{1-4}$ alkyl)amino;
R$^8$ is H, halogen, CN, carboxy, C$_{1-4}$ alkyloxycarbonyl, N$_3$, amino, C$_{1-4}$ alkylamino, di(C$_{1-4}$ alkyl)amino, hydroxy, C$_{1-6}$ alkoxy, C$_{1-6}$ alkylthio, C$_{1-6}$ alkylsulfonyl, or (C$_{1-4}$ alkyl)$_{0-2}$ aminomethyl;
R$^{11}$ is H or C$_{1-6}$ alkyl; and
R$^{14}$ is H, CF$_3$, C$_{1-4}$ alkyl, amino, C$_{1-4}$ alkylamino, C$_{3-6}$ cycloalkylamino, or di(C$_{1-4}$ alkyl)amino.

25. A method of making a compound of Formula II.A or Formula II.B or salt thereof, said method comprising:

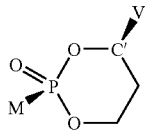

Formula II.A

-continued

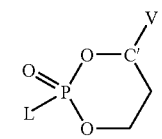

Formula II.B (a) isomerizing a mixture of trans/cis isomers of the compound of Formula I to give a ratio of trans/cis of about 85/15 or greater;

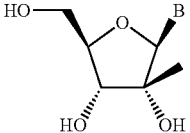

Formula I wherein:
V and L are trans relative to one another;
V is selected from the group consisting of heteroaryl, and phenyl, all optionally substituted with 1–4 substituents;
L is selected from the group consisting of halogen, and aryloxy optionally substituted with 1–2 substituents; and
(b) reacting the compound of Formula I having the ratio of trans/cis isomers of about 85/15 or greater, or salt thereof, with MH, wherein M is a nucleoside residue of Formula III;

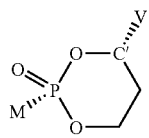

Formula III wherein:
B is selected from the group consisting of

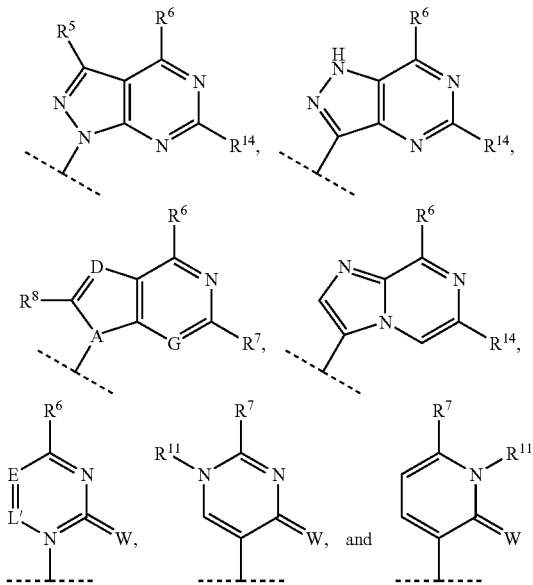

wherein:
A, G, and L' are each independently CH or N;
D is N, CH, C—CN, C—NO$_2$, C—C$_{1-3}$ alkyl, C—NH-CONH$_2$, C—CONR$^{11}$R$^{11}$, C—CSNR$^{11}$R$^{11}$, C—COOR$^{11}$, C—C(=NH)NH$_2$, C-hydroxy, C—C$_{1-3}$ alkoxy, C-amino, C—C$_{1-4}$ alkylamino, C-di(C$_{1-4}$ alkyl)

amino, C-halogen, C-(1,3oxazol-2-yl), C-(1,3-thiazol-2-yl), or C-(imidazol-2-yl); wherein alkyl is unsubstituted with one to three groups independently selected from halogen, amino, hydroxy, carboxy, and $C_{1-3}$ alkoxy;

E is N or $CR^5$;

W is O or S;

$R^5$ is H, $C_{1-6}$ alkyl, $C_{2-6}$ alkenyl, $C_{2-6}$ alkynyl, $C_{1-4}$ alkylamino, $CF_3$, or halogen;

$R^6$ is H, OH, SH, $NH_2$, $C_{1-4}$ alkylamino, di($C_{1-4}$ alkyl)amino, $C_{3-6}$ cycloalkylamino, halogen, $C_{1-4}$ alkyl, $C_{1-4}$ alkoxy, or $CF_3$;

$R^7$ is H, amino, $C_{1-4}$ alkylamino, $C_{3-6}$ cycloalkylamino, or di($C_{1-4}$ alkyl)amino;

$R^8$ is H, halogen, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;

$R^{11}$ is H or $C_{1-6}$ alkyl; and $R^{14}$ is H, $CF_3$, $C_{1-4}$ alkyl, amino, $C_{1-4}$ alkylamino, $C_{3-6}$ cycloalkylamino, or di($C_{1-4}$ alkyl)amino.

26. The method of claim 25, wherein said isomerizing comprises treating the compound of Formula I with L⁻ to give the ratio of trans/cis isomers of about 85/15 or greater.

27. The method of claim 25, wherein said isomerizing comprises heating the compound of Formula I to give the ratio of trans/cis isomers of about 85/15 or greater.

28. The method of claim 27, wherein said heating is from 40° C. to 70° C.

29. The method of claim 25, wherein said isomerizing comprises isolating the cis isomer from the mixture of trans/cis isomers of Formula I and treating the cis isomer with L⁻ to give the ratio of trans/cis isomers of about 85/15 or greater.

30. The method of claim 25, wherein B is selected from the group consisting of

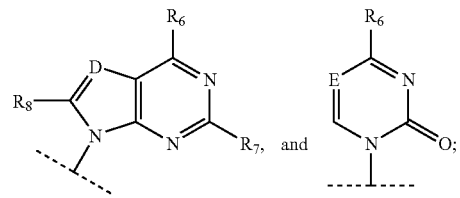

wherein:

D is N, CH, C—CN, C—$NO_2$, C—$C_{1-3}$ alkyl, C—NH-$CONH_2$, C—$CONR^{11}R^{11}$, C—$COOR^{11}$, C-hydroxy, C—$C_{1-3}$ alkoxy, C-amino, C—$C_{1-4}$ alkylamino, C-di($C_{1-4}$ alkyl)amino, or C-halogen;

E is N or $CR^5$;

$R^5$ is H, $C_{1-6}$ alkyl, $C_{2-6}$ alkenyl, $C_{2-6}$ alkynyl, $C_{1-4}$ alkylamino, $CF_3$, or halogen;

$R^6$ is H, OH, SH, $NH_2$, $C_{1-4}$ alkylamino, di($C_{1-4}$ alkyl)amino, $C_{3-6}$ cycloalkylamino, halogen, $C_{1-4}$ alkyl, $C_{1-4}$ alkoxy, or $CF_3$;

$R^7$ is H, amino, $C_{1-4}$ alkylamino, $C_{3-6}$ cycloalkylamino, or di($C_{1-4}$ alkyl)amino;

$R^8$ is H, halogen, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;

$R^{11}$ is H or $C_{1-6}$ alkyl.

31. The method of claim 25, wherein B is selected from the group consisting of

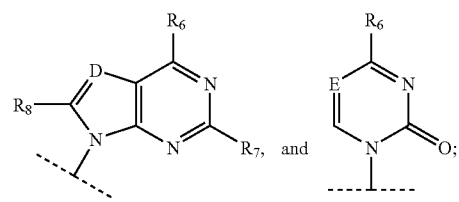

wherein:

D is N, CH, or C-halogen

E is N or C-Me;

$R^6$ is OH, or $NH_2$;

$R^7$ is H or amino;

$R^8$ is H or halogen.

32. The method of claim 25, wherein B is selected from the group consisting of

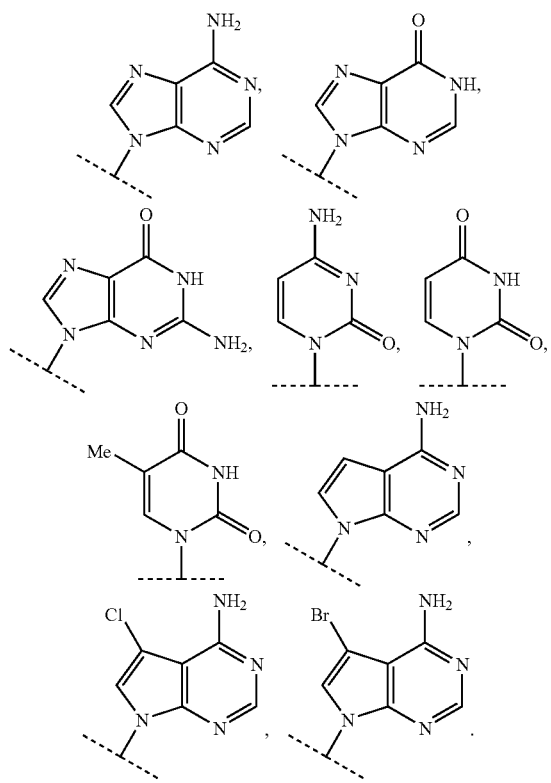

33. A method for the preparation of a compound of Formula V, said method comprising:

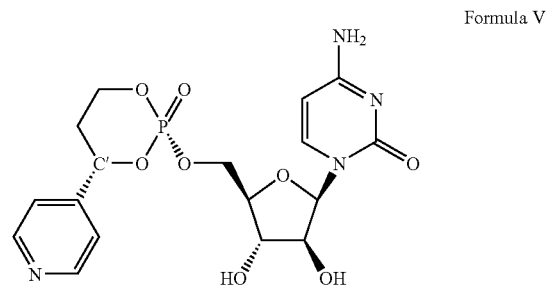

Formula V (a) isomerizing a mixture of trans/cis isomers of the compound of Formula IV to give the compound of Formula IV wherein the ratio of trans/cis isomers is about 85/15 or greater;

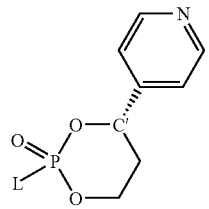

Formula IV wherein L is selected from the group consisting of chloro and 4-nitrophenoxy, and (b) coupling the compound of Formula IV having the ratio of trans/cis isomers of about 85/15 or greater, with optionally protected cytarabine.

34. The method of claim 33, wherein said isomerizing comprises treating the mixture of trans/cis isomers of the compound of Formula IV with L$^-$ to give the ratio of trans/cis isomers of about 85/15 or greater.

35. The method of claim 33, wherein said isomerizing comprises heating the mixture of trans/cis isomers of the compound of Formula IV to give the ratio of trans/cis isomers of about 85/15 or greater.

36. The method of claim 35, wherein said heating is from 40° C. to 70° C.

37. The method of claim 33, wherein said isomerizing comprises isolating the cis isomer from the mixture of trans/cis isomers of Formula IV and treating the cis isomer with L$^-$ to give the ratio of trans/cis isomers of about 85/15 or greater.

38. The method of claim 33, wherein a base is used in the coupling reaction in (b).

39. The method of claim 38, wherein said base is RMgX wherein:
R is C1–C5 alkyl; and
X is halogen.

40. The method of claim 39, wherein said base is t-BuMgCl.

41. The method of claim 33, wherein the hydroxyl groups and 4-amino group of cytarabine are protected.

42. The method of claim 41, wherein the 4-amino of cytarabine is protected as a dimethylformamidine.

43. The method of claim 33, wherein a protecting group for the 2' and 3' hydroxyl groups of cytarabine is selected from the group consisting of trialkylsilyl ether, optionally substituted methoxy methyl (MOM) ether, and optionally substituted 2-methoxyethoxy methyl (MEM) ether.

44. The method of claim 33, wherein said protecting group for 2' and 3' hydroxyl groups of cytarabine is t-butyldimethylsilyl ether.

45. The method of claim 33, wherein the hydroxyl groups and 4-amino group of cytarabine are not protected.

46. The method of claim 45, wherein L is chloro.

47. The method of claim 33, further comprising: forming an anion of said optionally protected cytarabine with a base; adding a Mg salt; and generating the Mg salt of the anion of said optionally protected cytarabine.

48. The method of claim 47, wherein said base is selected from the group consisting of alkali hydride, organometallic base, trialkylamine, and N-containing heteroaryl base.

49. The method of claim 47, wherein said salt is selected from the group consisting of $MgCl_2$, $MgBr_2$, and $MgI_2$.

50. The method of claim 47, wherein said base is NaH and said salt is $MgCl_2$.

51. The method of claim 47, wherein said base is t-BuOK and said salt is $MgCl_2$.

52. The method of claim 47, wherein said base is BuLi and said salt is $MgCl_2$.

53. The method of claim 47, wherein said base is 1,8-diazabicyclo[5.4.0]undec-7-ene (DBU) and said salt is $MgCl_2$.

54. The method of claim 47, wherein said base is $Et_3N$ and said salt is $MgCl_2$.

55. The method of claim 33, further comprising:
using t-BuMgCl as a base;
using the compound of Formula IV

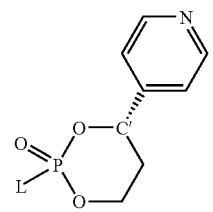

Formula IV wherein:
L is 4-nitrophenoxy; and
said optionally protected cytarabine has the 2' and 3' hydroxyl groups protected as t-butyldimethylsilyl ethers and the 4 amino group protected as dimethylformamidine.

56. A method of making a compound of Formula II.A or Formula II.B or salt thereof

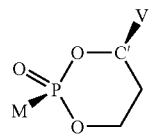

Formula II.A

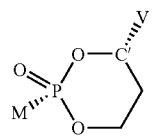

Formula II.B said method comprising:
(a) isomerizing a mixture of trans/cis isomers of the compound of Formula I to give a ratio of trans/cis of about 85/15 or greater;

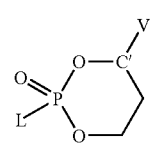

Formula I wherein:
V and L are trans relative to one another;

V is selected from the group consisting of heteroaryl, and phenyl, all optionally substituted with 1–4 substituents;

L is selected from the group consisting of halogen, and aryloxy optionally substituted with 1–2 substituents; and (b) reacting the compound of Formula I having the ratio of trans/cis isomers of about 85/15 or greater, or salt thereof, with MH, wherein:

MH is a nucleoside, and wherein:

H is attached to O, S, or N of said nucleoside; and

M is attached to phosphorus via an oxygen, nitrogen or sulfur atom.

57. The method of claim 56, wherein said isomerizing comprises treating the mixture of trans/cis isomers of the compound of Formula I with L⁻ to give the ratio of trans/cis isomers of about 85/15 or greater.

58. The method of claim 56, wherein said isomerizing comprises heating the mixture of trans/cis isomers of the compound of Formula I to give the ratio of trans/cis isomers of about 85/15 or greater.

59. The method of claim 58, wherein said heating is from 40° C. to 70° C.

60. The method of claim 56, wherein said isomerizing comprises isolating the cis isomer from the mixture of trans/cis isomers of Formula I and treating the cis isomer with L⁻ to give the ratio of trans/cis isomers of about 85/15 or greater.

61. The method of claim 56, wherein M is attached to phosphorus via an oxygen present in a primary hydroxyl on MH.

62. The method of claim 56, wherein M is a nucleoside in which the sugar is acyclic.

63. The method of claim 62, wherein M is attached to phosphorus via an oxygen present in a hydroxyl group on the acyclic sugar in MH.

64. The method of claim 56, wherein MH is reacted with the compound of Formula I in the presence of a base.

65. The method of claim 56, wherein MH is a protected nucleoside and further comprising the steps of:
forming an anion of MH with a base; and
adding the compound of Formula I or salt thereof to said anion.

66. The method of claim 56, wherein MH is an unprotected nucleoside, and wherein the compound of Formula I or salt thereof is added to MH or salt thereof.

67. The method of claim 64, wherein said base is R'MgX' wherein:

R' is selected from the group consisting of C1–C5 alkyl, and aryl optionally substituted with 1–3 substituents; and X' is halogen.

68. The method of claim 67, wherein said base is selected from the group consisting of tert-BuMgCl, and phenylMgCl.

69. The method of claim 67, wherein said base is tert-BuMgCl.

70. The method of claim 56, further comprising:
forming an anion of a protected nucleoside with a base;
adding a Lewis acid; and
adding the compound of Formula I.

71. The method of claim 56, wherein MH is a nucleoside, and further comprising:
forming an anion of MH with a base;
adding a Mg salt; and
generating the Mg salt of said anion.

72. The method of claim 71, wherein said base is selected from the group consisting of alkali hydride, organometallic base, trialkylamine, and N-containing heteroaryl base.

73. The method of claim 71, wherein:
said base is selected from the group consisting of sodium hydride (NaH), lithium hydride (LiH), lithium diethylamide (LDA), lithium hexamethyldisilazide (LHMDS), potassium t-butoxide (t-BuOK), butyl lithium (BuLi), triethylamine (Et₃N), diisopropylethylamine, 1,8-diazabicyclo[5.4.0]undec-7-ene (DBU), diazabicyclo[2.2.2]octane (DABCO), and pyridine.

74. The method of claim 71, wherein said salt is selected from the group consisting of MgCl₂, MgBr₂, and MgI₂.

75. The method of claim 71, wherein said base is NaH and said salt is MgCl₂.

76. The method of claim 71, wherein said base is t-BuOK and said salt is MgCl₂.

77. The method of claim 71, wherein said base is BuLi and said salt is MgCl₂.

78. The method of claim 71, wherein said base is 1,8-diazabicyclo[5.4.0]undec-7-ene (DBU) and said salt is MgCl₂.

79. The method of claim 71, wherein said base is Et₃N and said salt is MgCl₂.

80. The method of claim 56, wherein said nucleoside is selected from the group consisting of araA (9-β-D-arabinofuranosyladenine); AZT (3'-azido-2',3'-dideoxythymidine); d4T (2',3'-didehydro-3'-deoxythymidine); ddI (2',3'-dideoxyinosine); ddA (2',3'-dideoxyadenosine); ddC (2',3'-dideoxycytidine); L-ddC (L-2',3'-dideoxycytidine); L-FddC (L-2',3'-dideoxy-5-fluorocytidine); L-d4C (β-L-2',3'-didehydro-2',3'-dideoxy-cytidine); L-Fd4C (β-L-2',3'-didehydro-2',3'-dideoxy-5-fluorocytidine); 3TC ((−)-2',3'-dideoxy-3'-thiacytidine); ribavirin (1-β-D-ribofuranosyl-1,2,4-triazole-3-carboxamide); 5-fluoro-2'-deoxyuridine; FIAU (1-(2'-deoxy-2'-fluoro-β-D-arabinofuranosyl)-5-iodouridine); FIAC (1-(2'-deoxy-2-fluoro-β-D-arabinofuranosyl)-5-iodocytosine); BHCG ((±)-(1α,2α,3α)-9-[2',3'-bis(hydroxymethyl)cyclobutyl]-guanine); L-FMAU (2'-Fluoro-5-methyl-β-L-arabinofuranosyluracil); BvaraU (1'-β-D-arabinofuranosyl-E-5-(2-bromovinyl)uracil); E-5-(2-bromovinyl)-2'-deoxyuridine); TFT (Trifluorothymidine); 5-propynyl-1'-arabinofuranosyluracil; CDG (carbocyclic 2'-deoxyguanosine); DAPD ((−)-β-D-2,6-diaminopurine dioxolane); FDOC ((−)-β-D-5-fluoro-1-[2'-(hydroxymethyl)-1',3'-dioxolane]cytosine); d4C (-2',3'-didehydro-2',3'-dideoxy-cytidine); DXG (dioxolane guanosine); FEAU (2'-deoxy-2'-fluoro-1'-β-D-arabinofuranosyl-5-ethyluracil); FLG (2',3'-dideoxy-3'-fluoroguanosine); FTC ((−)-cis-5-fluoro-1-[2'-(hydroxymethyl)-1',3'-oxathiolan-5'-yl]-cytosine); L-dC (β-L-2'-deoxycytosine); L-dT (β-L-2'-deoxythymidine); 5-yl-carbocyclic-2'-deoxyguanosine; oxetanocin A (9-(2'-deoxy-2'-hydroxymethyl-β-D-erythro-oxetanosyl)adenine); oxetanocin G (9-(2'-deoxy-2'-hydroxymethyl-β-D-erythro-oxetanosyl)guanine); Cyclobut A ((+/−)-9-[(1'-β,2'-α,3'-β)-2',3'-bis(hydroxymethyl)-1'-cyclobutyl]adenine); Cyclobut G ((+/−)-9-[(1'-β,2'-α,3'-β)-2,3-bis(hydroxymethyl)-1-cyclobutyl]guanine); dFdC (2',2'-difluoro-2'-deoxycytidine); araC (arabinofuranosylcytosine); bromodeoxyuridine; IDU (5-iodo-2'-deoxyuridine); CdA (2-chloro-2'-deoxyadenosine); FaraA (2-fluoroarabinofuranosyladenosine); Coformycin; 2'-deoxycoformycin; araT (1-β-D-arabinofuranoside thymidine); tiazofurin; ddAPR (2,6-diaminopurine-2',3'-dideoxyriboside); 9-(arabinofuranosyl)-2,6-diaminopurine; 9-(2'-deoxyribofuranosyl)-2,6-diaminopurine; 9-(2'-deoxy-2'-fluororibofuranosyl)-2,6-diaminopurine; 9-(arabinofuranosyl)guanine; 9-(2'-deoxyribofuranosyl)guanine; 9-(2'-deoxy2'-fluororibofuranosyl)guanine; FMDC ((E)-2'-deoxy-2'(fluoromethylene)cytidine); DMDC (2'-deoxy-2'- methyledene-cytidine); 4'-thio-araC (4'-thio-arabinofuranosyl-cytidine); 5,6 dihydro-5-azacytidine; 5-azacytidine; 5-aza-2'-deoxycytidine; AICAR (5-aminoimidazole-4-carboxamido-1-ribofuranosyl); NK-84-0218; AM365; MCC$_{478}$; ICN 2001; Fluor L and D nucleosides; Famciclovir (2-[2-(2-amino-9H-purin-9-yl)ethyl]-1,3-propanediol diacetate); ACV (9-(2'-hydroxyethoxylmethyl)guanine); GCV (9-(1',3'-dihydroxy-2'-propoxymethyl)guanine); penciclovir (9-(4'-hydroxy-3'-hydroxymethylbut-1'-yl)guanine); (R)-9-(3',4'-dihydroxybutyl)guanine, cytallene (1-(4'-hydroxy-1',2'-butadienyl)cytosine), and 2'-β-methyl-ribofuranosyl nucleosides of Formula III:

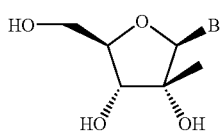

Formula III wherein:
B is selected from the group consisting of

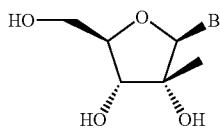

Formula III wherein:

A, G, and L' are each independently CH or N;

D is N, CH, C—CN, C—NO$_2$, C—C$_{1-3}$ alkyl, C—NHCONH$_2$, C—CONR$^{11}$R$^{11}$, C—CSNR$^{11}$R$^{11}$, C—COOR$^{11}$, C—C(=NH)NH$_2$, C-hydroxy, C—C$_{1-3}$ alkoxy, C-amino, C—C$_{1-4}$ alkylamino, C-di(C$_{1-4}$ alkyl) amino, C-halogen, C-(1,3oxazol-2-yl), C-(1,3-thiazol-2-yl), or C-(imidazol-2-yl); wherein alkyl is unsubstituted or substituted with one to three groups independently selected from halogen, amino, hydroxy, carboxy, and C$_{1-3}$ alkoxy;

E is N or CR$^5$;

W is O or S;

R$^5$ is H, C$_{1-6}$ alkyl, C$_{2-6}$ alkenyl, C$_{2-6}$ alkynyl, C$_{1-4}$ alkylamino, CF$_3$, or halogen;

R$^6$ is H, OH, SH, NH$_2$, C$_{1-4}$ alkylamino, di(C$_{1-4}$ alkyl) amino, C$_{3-6}$ cycloalkylamino, halogen, C$_{1-4}$ alkyl, C$_{1-4}$ alkoxy, or CF$_3$;

R$^7$ is H, amino, C$_{1-4}$ alkylamino, C$_{3-6}$ cycloalkylamino, or di(C$_{1-4}$ alkyl)amino;

R$^8$ is H, halogen, CN, carboxy, C$_{1-4}$ alkyloxycarbonyl, N$_3$, amino, C$_{1-4}$ alkylamino, di(C$_{1-4}$ alkyl)amino, hydroxy, C$_{1-6}$ alkoxy, C$_{1-6}$ alkylthio, C$_{1-6}$ alkylsulfonyl, or (C$_{1-4}$ alkyl)$_{0-2}$ aminomethyl;

R$^{11}$ is H or C$_{1-6}$ alkyl; and

R$^{14}$ is H, CF$_3$, C$_{1-4}$ alkyl, amino, C$_{1-4}$ alkylamino, C$_{3-6}$ cycloalkylamino, or di(Ci$_{1-4}$ alkyl)amino.

\* \* \* \* \*

UNITED STATES PATENT AND TRADEMARK OFFICE
CERTIFICATE OF CORRECTION

PATENT NO.        : 7,148,349 B2
APPLICATION NO.   : 10/698924
DATED             : December 12, 2006
INVENTOR(S)       : Reddy et al.

It is certified that error appears in the above-identified patent and that said Letters Patent is hereby corrected as shown below:

Page 2, column 2, lines 5 to 6, after Jacobsen, E.N., *et al.*, and before Li *et al.*, insert therein -- Kobayashi *et al.*, *Tetrahedron Lett.* 27:4745 (1986). --

Page 4, column 1, line 15, please delete "36:1145-11148, Consultants Bureau (1987)." and insert therein -- 36:1145-1148, Consultants Bureau (1987). --

Column 63, line 6, please delete "40° C." and insert therein -- 40° C --.

Column 64, line 61, please delete "$MCC_{478}$;" and insert therein -- MCC478; --.

Column 64, line 62, please delete "Famoiclovir" and insert therein -- Famciclovir --.

Column 65, lines 25 to 32, please delete

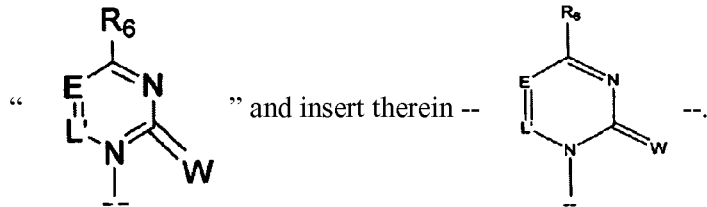

In column 66, lines 53 to 60, please delete

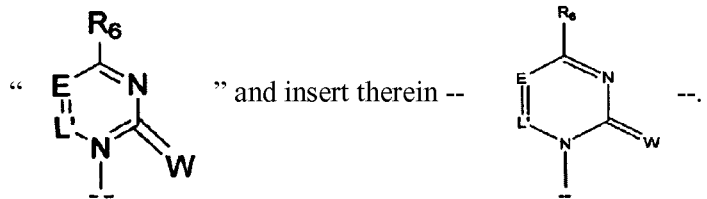

Column 67, line 30, please delete "40° C." and insert therein -- 40° C --.

Column 69, line 31, please delete "40° C." and insert therein -- 40° C --.

Column 71, line 22, please delete "40° C." and insert therein -- 40° C --.

Column 72, lines 65 to 66, please delete "9-(2'-deoxy2'-fluororibofuranosyl)guanine;" and insert therein -- 9-(2'-deoxy-2'-fluororibofuranosyl)guanine; --.

UNITED STATES PATENT AND TRADEMARK OFFICE
CERTIFICATE OF CORRECTION

PATENT NO.       : 7,148,349 B2
APPLICATION NO.  : 10/698924
DATED            : December 12, 2006
INVENTOR(S)      : Reddy et al.

It is certified that error appears in the above-identified patent and that said Letters Patent is hereby corrected as shown below:

Column 73, line 5, please delete "$MCC_{478}$;" and insert -- MCC478; --.

Column 73, lines 24 to 29, please delete

"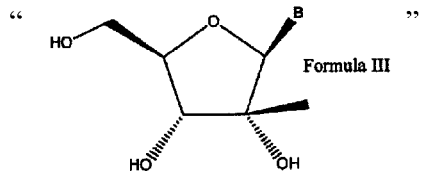"

and insert therein

-- 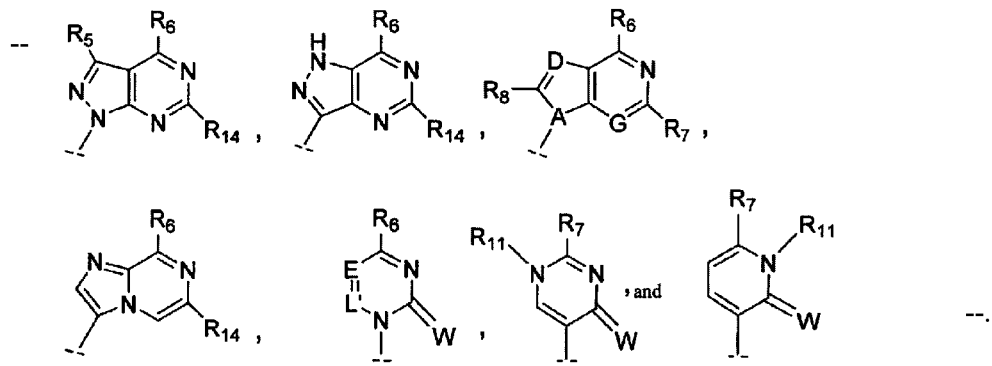 --.

Signed and Sealed this

Twenty-seventh Day of May, 2008

JON W. DUDAS
*Director of the United States Patent and Trademark Office*